(12) United States Patent
Meese et al.

(10) Patent No.: US 8,338,478 B2
(45) Date of Patent: *Dec. 25, 2012

(54) DERIVATIVES OF 3,3-DIPHENYLPROPYLAMINES

(75) Inventors: Claus Meese, Monheim (DE); Bengt Sparf, Trangsund (DE)

(73) Assignee: UCB Pharma GmbH, Monheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/161,049

(22) Filed: Jun. 15, 2011

(65) Prior Publication Data

US 2011/0294882 A1    Dec. 1, 2011

Related U.S. Application Data

(63) Continuation of application No. 12/814,982, filed on Jun. 14, 2010, now Pat. No. 7,985,772, which is a continuation of application No. 12/105,016, filed on Apr. 17, 2008, now Pat. No. 7,855,230, which is a continuation of application No. 11/201,756, filed on Aug. 10, 2005, now Pat. No. 7,384,980, which is a continuation of application No. 10/766,263, filed on Jan. 27, 2004, now Pat. No. 7,230,030, which is a continuation of application No. 09/700,094, filed as application No. PCT/EP99/03212 on May 11, 1999, now Pat. No. 6,713,464.

(30) Foreign Application Priority Data

May 12, 1998    (EP) .................................... 98108608

(51) Int. Cl.
*A61K 31/21* (2006.01)
*C07C 229/00* (2006.01)

(52) U.S. Cl. .......................................... 514/506; 560/39
(58) Field of Classification Search .................... None
See application file for complete search history.

(56) References Cited

U.S. PATENT DOCUMENTS

| | | | |
|---|---|---|---|
| 2,556,636 A | 6/1951 | Sperber et al. |
| 2,567,245 A | 9/1951 | Sperber et al. |
| 2,676,964 A | 4/1954 | Sperber et al. |
| 3,261,841 A | 7/1966 | Zenitz |
| 3,446,901 A | 5/1969 | Macclesfield |
| 4,988,730 A | 1/1991 | Korbonits et al. |
| 5,382,600 A | 1/1995 | Jonsson et al. |
| 5,559,269 A | 9/1996 | Johansson et al. |
| 5,686,464 A | 11/1997 | Johansson et al. |
| 5,922,914 A | 7/1999 | Gage et al. |
| 6,310,248 B2 | 10/2001 | Andersson et al. |
| 6,313,132 B1 | 11/2001 | Johansson et al. |
| 6,517,864 B1 | 2/2003 | Jacobsen et al. |
| 6,566,537 B2 | 5/2003 | Andersson et al. |
| 6,630,162 B1 | 10/2003 | Nilvebrant et al. |
| 6,689,916 B2 | 2/2004 | Andersson et al. |
| 6,713,464 B1 | 3/2004 | Meese et al. |
| 6,770,295 B1 | 8/2004 | Kreilgard et al. |
| 6,783,769 B1 | 8/2004 | Arth et al. |
| 6,809,214 B2 | 10/2004 | Meese |
| 6,809,225 B2 | 10/2004 | Donsbach et al. |
| 6,858,650 B1 | 2/2005 | Meese |
| 6,890,920 B2 | 5/2005 | Richards et al. |
| 6,911,217 B1 | 6/2005 | Gren et al. |
| 7,008,637 B2 | 3/2006 | Jacobsen et al. |
| 7,230,030 B2 | 6/2007 | Meese et al. |
| 7,384,980 B2 | 6/2008 | Meese et al. |
| 7,855,230 B2 * | 12/2010 | Meese et al. ................... 514/532 |
| 7,985,772 B2 * | 7/2011 | Meese et al. ................... 514/513 |
| 2003/0152624 A1 | 8/2003 | Aldrich et al. |
| 2004/0064821 A1 | 4/2004 | Rousselle |
| 2005/0004223 A1 | 1/2005 | Slatter et al. |

FOREIGN PATENT DOCUMENTS

| | | |
|---|---|---|
| DE | 830193 | 2/1952 |
| DE | 766207 | 12/1952 |
| DE | 925468 | 3/1955 |
| DE | 1216318 | 5/1966 |
| EP | 325571 | 7/1989 |
| EP | 667852 | 8/1995 |
| EP | 831799 | 6/1996 |
| EP | 872233 | 4/1997 |
| EP | 948321 | 12/1997 |
| EP | 957073 | 5/1998 |
| EP | 1019358 | 7/2000 |
| EP | 1077912 | 2/2001 |
| EP | 1128819 | 9/2001 |
| GB | 624117 | 5/1949 |
| GB | 627139 | 7/1949 |
| GB | 685696 | 1/1953 |
| GB | 689835 | 4/1953 |
| GB | 690274 | 4/1953 |
| GB | 692931 | 6/1953 |

(Continued)

OTHER PUBLICATIONS

Abrams et al., "Tolterodine, a new antimuscarinic agent: as effective but better tolerated than oxybutynin in patients with an overactive bladder," 1998, Br. J. Urol. 81:801-810.

Abstracts from the 26th Annual Meeting of the International Incontinence Society, Aug. 27-30, 1996, Gillberg et al., abstract 33, Neurology and Urodynamics 15:308-309.

Anderson et al., "Once daily controlled versus immediate release oxybutynin chloride for urge urinary incontinence," 1999, J. Urol. 161:1809-1812.

(Continued)

*Primary Examiner* — Noble Jarrell
(74) *Attorney, Agent, or Firm* — Kenyon & Kenyon, LLP

(57) ABSTRACT

The invention concerns novel derivatives of 3,3-diphenylpropylamines, methods for their preparation, pharmaceutical compositions containing the novel compounds, and the use of the compounds for preparing drugs. More particularly, the invention relates to novel prodrugs of antimuscarinic agents with superior pharmacokinetic properties compared to existing drugs such as oxybutynin and tolterodine, methods for their preparation, pharmaceutical compositions containing them, a method of using said compounds and compositions for the treatment of urinary incontinence, gastrointestinal hyperactivity (irritable bowel syndrome) and other smooth muscle contractile conditions.

12 Claims, 1 Drawing Sheet

FOREIGN PATENT DOCUMENTS

| | | |
|---|---|---|
| GB | 1025041 | 2/1964 |
| GB | 1169944 | 11/1969 |
| GB | 1169945 | 11/1969 |
| WO | 89/06644 | 7/1989 |
| WO | 93/23025 | 11/1993 |
| WO | 94/11337 | 5/1994 |
| WO | 96/12477 | 5/1996 |
| WO | 98/03067 | 1/1998 |
| WO | 98/43942 | 10/1998 |
| WO | 98/56359 | 12/1998 |
| WO | 99/58478 | 11/1999 |
| WO | 00/12069 | 3/2000 |
| WO | 00/27364 | 5/2000 |
| WO | 01/34139 | 5/2001 |
| WO | 02/11702 | 2/2002 |
| WO | 02/089773 | 11/2002 |
| WO | 03/002059 | 1/2003 |
| WO | 03/007918 | 1/2003 |
| WO | 03/020241 | 3/2003 |
| WO | 03/021271 | 3/2003 |
| WO | 03/026564 | 4/2003 |
| WO | 03/035599 | 5/2003 |
| WO | 03/039464 | 5/2003 |
| WO | 03/063834 | 8/2003 |
| WO | 03/099268 | 12/2003 |
| WO | 03/103637 | 12/2003 |
| WO | 03/106421 | 12/2003 |
| WO | 2004/019892 | 3/2004 |

OTHER PUBLICATIONS

Andersson et al., "Pharmacological treatment of urinary incontinence," in Abrams P., Khoury S., Wein A. (Eds), Incontinence, 2nd International Consultation on Incontinence, Plymouth, Plymbridge Distributors Ltd, UK, Plymouth, 2002, pp. 479-511.

Andersson, "Antimuscarinics for treatment of overactive bladder," 2004, Lancet Neurol. 3:46-53.

Andersson & Hedlund, "Pharmacological perspective on the physiology of the lower urinay tract," 2002, Urology 60 (Suppl. 5A):13-20.

Andersson & Wein, "Pharmacology of the lower urinary tract: basis for current and future treatments of urinary incontinence," 2004, Pharmacol. Rev. 56:581-631.

Andersson et al., "Biotransformation of Tolterodine, a New Muscarinic Receptor Antagonist, in Mice, Rats, and Dogs." Drug Metabolism and Disposition, vol. 26 (6), pp. 528-535, 1998.

Andersson, "Current Concepts in the Treatment of Discorders of Micturition." Drugs 35, pp. 477-494, 1988.

Appell et al., "Prospective randomized controlled trial of extended release oxybutynin chloride and tolterodine tartrate in the treatment of overactive bladder: results of the OBJECT study," 2001, Mayo Clinic Proceedings 76:358-363.

Breidenbach et al., "Pharmacodynamic profiling of the novel antimuscarinic drug fesoterodine on rat bladder," 2002, Proceedings of the International Continence Society, 32:449.

Brynne et al., Influence of CYP2D6 polymorphism on the pharmacokinetics and pharmacodynamics of tolterodine, 1998, Clin. Pharmacol. Thera. 63:529-539.

Brynne et al., "Tolterodine does not affect the human in vivo metabolism of the probe drugs caffeine, debrisoquine, and omeprazole," 1999, Br. J. Clin. Pharmacol. 47:145-150.

Brynne et al., "Fluoxetine inhibits the metabolism of tolterodine—pharmacokinetic implications and proposed clinical relevance," 1999, Br. J. Clin. Pharmacol. 48:553-563.

Brynne et al., "Ketoconazole inhibits the metabolism of tolterodine in subjects with deficient CYP2D6 activity," 1999, Br. J. Clin. Pharmacol. 48:564-572.

Brynne et al., "Pharmacokinetics and Pharmacodynamics of Tolterodine in Man: a New Drug for the Treatment of Urinary Bladder Overactivity." J. Clin. Pharm. Ther., vol. 35 (7), pp. 297-295, 1997.

Cawello et al., "Multiple dose pharmacokinetics of fesoterodine in human subjects," 2002, Nauyn-Schmiedeberg's Arch. Pharmacol. 365 (Suppl. 1):248, 2002.

Chancellor et al., "A comparison of the effects on saliva output of oxybutynin chloride and tolterodine tartrate," 2001, Clinical Therapeutics 23:753-760.

Chapple & Udo, "Delay to maximum effect in overactive bladder patients treated with oxybutynin or tolterodine," 2000, European Urology 37(Suppl. 2):84, abstract 335 from the XVth Congress of the European Association of Urology, Brussels, Belgium, Apr. 12-15, 2000.

Chapple et al., "Fesoterodine a new effective and well-tolerated antimuscarinic for the treatment of urgency-frequency syndrome: results of a Phase II controlled study," 2004, Proceedings of the International Continence Society, 34:142.

Clemett & Jarvis, "Tolterodine: a review of its use in the treatment of overactive bladder," 2001, Drugs & Aging 18:277-304.

Cole, "Fesoterodine, an advanced antimuscarinic for the treatment of overactive bladder: A safety update," 2004, Drugs of the Future 29:715-720.

Committee for Proprietary Medicinal Products, "The assessment of the potential for QT interval prolongation by non-cardiovascular medicinal products," CPMP/986/96, Dec. 17, 1997.

Detrol® package insert, Pharmacia & Upjohn Co., Apr. 2004.

Diokno et al., "Tolterodine (Detrol®) improves incontinence and nocturia in urological based study," Apr. 1999, J. Urol. 161 (4 Suppl):256, abstract 987.

Ekstrom et al., "Effects of tolterodine on bladder function in healthy volunteers," Journal of Urology 153(Suppl.):394A, abstract 662 from the 19th Annual Meeting of the American Urological Association, Las Vegas, Apr. 23-28, 1995.

Gardner & Altman, "Confidence intervals rather than P values: estimation rather than hypothesis testing," 1986, Br. Med. J. 292:746-750.

Gillberg et al., "Tolterodine, a new agent with tissue effect selectivity for urinary bladder," 1994, Neurourology and Urodynamics 13:435-436, abstract 60B from International Continence Society 24th Annual Meeting, Prague, Czech Republic, Aug. 1994.

Gillberg et al., "Comparison of the in vitro and in vivo profiles of tolterodine with those of subtype-selective muscarinic receptor antagonists," 1998, European Journal of Pharmacology 349: 285-292.

Hills et al., "Tolterodine," 1998, Drugs 55:813-820.

Jonas et al., "Efficacy and safety of two doses of tolterodine versus placebo in patients with detrusor overactivity and symptoms of frequency, urge incontinence, and urgency: urodynamic evaluation," 1997, World J. Urol. 15:144-151.

Kang et al., "Cardiac ion channel effects of Tolterodine," 2004, J. Pharmacol. Exper. Thera. 308:935-940.

Kawazoe et al., "Selective Desilylation of Phenolic and Alcoholic Trimethylsilyl Ethers." Tetrahedron Lett. 28: 4307-4310, 1987.

Kershen & Hsieh, "Preview of new drugs for overactive bladder and incontinence: darifenacin, solifenacin, trospium, and duloxetine," Curr. Urol. Rep. 5:359-367, 2004.

Klosa, "Eine Neue Synthesemethode der Darstellung von Diarylalkylaminen," 1966, Journal für Praktische Chemie 4:312-334 (in German) with English translation.

Klosa, "Eine Neue Synthese von Diphenylisopropylaminen," 1966, Journal für Praktische Chemie 4:335-340 (in German, with English translation).

Larsson et al., "Tolterodine in the treatment of overactive bladder: analysis of the pooled phase II safety and efficacy data," 1999, Urology 53: 990-998.

Lipinski, et al., "Experimental and computational approaches to estimate solubility and permeability in drug discovery and development settings" Elsevier Advanced Drug Delivery Reviews vol. 23, pp. 3-25, 1997.

Loubinoux et al., "Reactivity of new Precursors of Quinone Methides." Tetrahedron Lett. 30: 1939-1942, 1989.

Millard et al., "Clinical efficacy and safety of tolterodine compared to placebo in detrusor overactivity," 1999, J. Urol. 161:1551-1555.

Modiri et al., "Effect of muscarinic antagonists on micturition pressure measured by cystometry in normal, conscious rats," 2002, Urology 59:963-968.

Naerger et al., "Effect of tolterodine on electrically induced contractions of isolated human detrusor muscle from stable and unstable bladders," 1995, Neurourology and Urodynamics 14:524-526, abstract 76 from International Continence Society 25th Annual Meeting, Sydney, Australia, Oct. 1995.

Netzer, et al., "Screening lead compounds for QT interval prolongation" Drug Discovery Today vol. 6, No. 2, pp. 78-84, Jan. 2001.

Nilsson et al., "Comparison of a 10 mg controlled release oxybutynin tablet with a 5 mg oxybutynin tablet in urge incontinence patients," 1997, Neurourol. Urodyn. 16:533-542.

Nilvebrant & Spell, "Receptor binding profiles of some selective muscarinic antagonists," 1988, European Journal of Pharmacology 151:83-96.

Nilvebrant & Sparf, "Differences between Binding Affinities of some Antimuscarinic Drugs in the parotid Gland and those in the Urinary Bladder and Ileum" Acta Pharmacol. et toxicol. vol. 53, No. 4, pp. 304-313, Oct. 1983.

Nilvebrant et al., "The in vitro pharmacological profile of tolterodine—a new agent for the treatment of urinary urge incontinence," 1994, Neurourology and Urodynamics 13:433-435, abstract 60A from International Continence Society 24th Annual Meeting, Prague, Czech Republic, Aug. 1994.

Nilvebrant et al., "Tolterodine is not subtype (m1-m5) selective but exhibits functional bladder selectivity in vivo," 1996, Neurourology and Urodynamics 15:310-311, abstract 34 from the 26th Annual Meeting of the International Continence Society, Athens, Greece, Aug. 27-30, 1996.

Nilvebrant, "Tolterodine and terodiline—different pharmacological profiles," pp. 141-142, abstract 181a, from the 27th Annual meeting of the International Continence Society, Yokohama, Japan, Sep. 1997.

Nilvebrant et al "Tissue distribution of tolterodine and its metabolites: low penetration into the central nervous system," 2000, European Urology 37(Suppl. 2):84, abstract 333 from the XVth Congress of the European Association of Urology, Brussels, Belgium, Apr. 12-15, 2000.

Nilvebrant, "The mechanism of action of tolterodine," 2000, Reviews in Contemporary Pharmacotherapy 11:13-27.

Nilvebrant et al., European Journal of Pharmacology, 327 (1997) pp. 195-207.

Nilvebrant et al., "Anitmuscarinic Potency and Bladder Selectivity of PNU-200577, a Major Metabolite of Tolterodine." Pharmacology and Toxicology, vol. 81, pp. 169-172, 1997.

Nilvebrant et al., "Tolterodine—a New Bladder Selective Muscarinic Receptor Antagonist: Preclinical Pharmacological and Clinical Data." Life Sciences, vol. 60 (13/14), pp. 1129-1136, 1997.

Olsson et al., "Food increases the bioavailability of tolterodine but not effective exposure," 2001, J. Clin. Pharmacol. 41:298-304.

Olsson & Szamosi, "Food does not influence the pharmacokinetics of a new extended release formulation of tolterodine for once daily treatment of patients with overactive bladder," 2001, Clinical Pharmacokinetics 40:135-143.

Olsson & Szamosi, "Multiple dose pharmacokinetics of a new once daily extended release formulation versus immediate release tolterodine," 2001, Clinical Pharmacokinetics 40:227-235.

Paladino et al., "177. Enantioselective Synthesis of (2S)-2-Amino-3-(4-hydroxy-3-phosphonophenyl)propionic Acid (=3'-Phosphono-L-tyrosine) and its Incorporation into Peptides." Helv. Chim. Acta 76: 2465-2472, 1993.

Pharmacology/Toxicology Review from Application No. 21-518, Center for Drug Evaluation and Research, pp. 1-3, 2001.

Postlind et al., "Tolterodine, a New Muscarinic Receptor Antagonist, is Metabolized by Cytochromes P450 and 3A in Human Liver Microsomes." Drug Metabolism and Disposition, vol. 26 (4), p. 289-293, 1998.

Rentzhog et al., "Efficacy and safety of tolterodine in patents with detrusor instability: a dose ranging study," 1998, Br. J. Urol. 81:42-48.

Roy, et al., "HERG, a Primary Human Ventricular Target of the Nonsedating Antihistamine Terfenadine" Circulation vol. 94, No. 4, pp. 817-823, Aug. 15, 1996.

Saa et al., "Metalation of Phenols. Synthesis of Benzoquinones by the Oxidative Degradation Approach." J. Org. Chem. 53: 4263-4273, 1988.

Sachse et al., "Pharmacodynamics of multiple dose treatment with the novel antimuscarinic drug fesoterodine," 2002, Nauyn-Schmiedeberg's Arch. Pharmacol. 365 (Suppl. 1):413.

Sachse et al., "Safety and pharmacokinetics of the novel bladder-selective antimuscarinic drug fesoterodine in populations of different age or gender," 2002, Proceedings of the International Continence Society, 32:441.

Sachse et al., "Safety and pharmacokinetics of the novel bladder-selective antimuscarinic fesoterodine in populations of different ethnic origin," 2003, Proceedings of the International Continence Society, 33:377.

Sachse et al., "Dose-proportional pharmacokinetics of the new antimuscarinic fesoterodine," 2003, Nauyn-Schmiedeberg's Arch. Pharmacol. 367 (Suppl. 1):446.

Sachse et al., "Pharmacodynamics and pharmacokinetics of ascending multiple oral doses of the novel, bladder-selective antimuscarinic fesoterodine," 2003, Eur. Urol. Suppl 2:111.

Sachse et al., "Concomitant food intake does not significantly influence the pharmacokinetics of the novel, bladder-selective antimuscarinic fesoterodine," 2004, Proceedings of the International Continence Society, 34:580.

Sachse et al., "Safety, tolerability and pharmacokinetics of fesoterodine in patients with hepatic impairment," 2004, Proceedings of the International Continence Society, 34:585.

Sachse et al., "Safety, tolerability and pharmacokinetics of fesoterodine after co-treatment with the potent cytochrome P450 3A4 inhibitor ketoconazole," 2004, Proceedings of the International Continence Society, 34:586.

Sachse et al., "Clinical pharmacological aspects of the novel bladder-selective antimuscarinic fesoterodine," 2004, Progrès en Urologie, 14 (Suppl. 3):58.

Stahl et al., "Urodynamic and other effects of tolterodine: a novel antimuscarinic drug for the treatment of detrusor overactivity," 1995, Neurourol. Urodyn. 14:647-55.

Teuvo et al "Extended release tolterodine compared with immediate release tolterodine for the treatment of overactive bladder," 2000, European Urology 37(Suppl. 2):84, abstract 334 from the XVth Congress of the European Association of Urology, Brussels, Belgium, Apr. 12-15, 2000.

Tiemessen et al., "A Two-Chambered Diffusion Cell with Improved Flow-Through Characteristics for Studying the Drug Permeability of Biological Membranes." Acta Pharm. Technol. 34:99-101, 1998.

Van Kerrebroeck et al., "Tolterodine once daily: superior efficacy and tolerability in the treatment of the overactive bladder," 2001, Urology 57:414-421.

Van Kerrebroeck et al., "Clinical efficacy and safety of tolterodine compared to oxybutynin in patients with overactive bladder," 1997, Neurourol. Urodyn. 16:478-479, abstract No. 91 from the 27th Annual meeting of the International Continence Society, Yokohama, Japan, Sep. 1997.

Versi et al., "Dry mouth with conventional and controlled release oxybutynin in urinary incontinence," 2000, Obstet. Gynecol. 95:718-721.

Vries et al., "The Family Approach to the Resolution of Racemates." Angew Chem. Int. Ed. Engl. 1998, vol. 37, p. 2349.

Wefer et al., "Tolterodine: an overview," 2001, World Journal of Urology 19:312-318.

"Organic chemistry reaction mechanisms", http://www.wikipremed.com/03_organicmechansims.php?mch_code=030207_080, accessed Nov. 7, 2009.

Amendment filed in U.S. Appl. No. 11/201,756, Jan. 18, 2008.
Declaration filed in U.S. Appl. No. 11/201,756, Jan. 18, 2008.
Exhibit A filed in U.S. Appl. No. 11/201,756, Feb. 19, 2008.
Exhibit B filed in U.S. Appl. No. 11/201,756, Jan. 18, 2008.
Exhibit C filed in U.S. Appl. No. 11/201,756, Jan. 18, 2008.
Exhibit D filed in U.S. Appl. No. 11/201,756, Jan. 18, 2008.
Exhibit E filed in U.S. Appl. No. 11/201,756, Feb. 19, 2008.

* cited by examiner

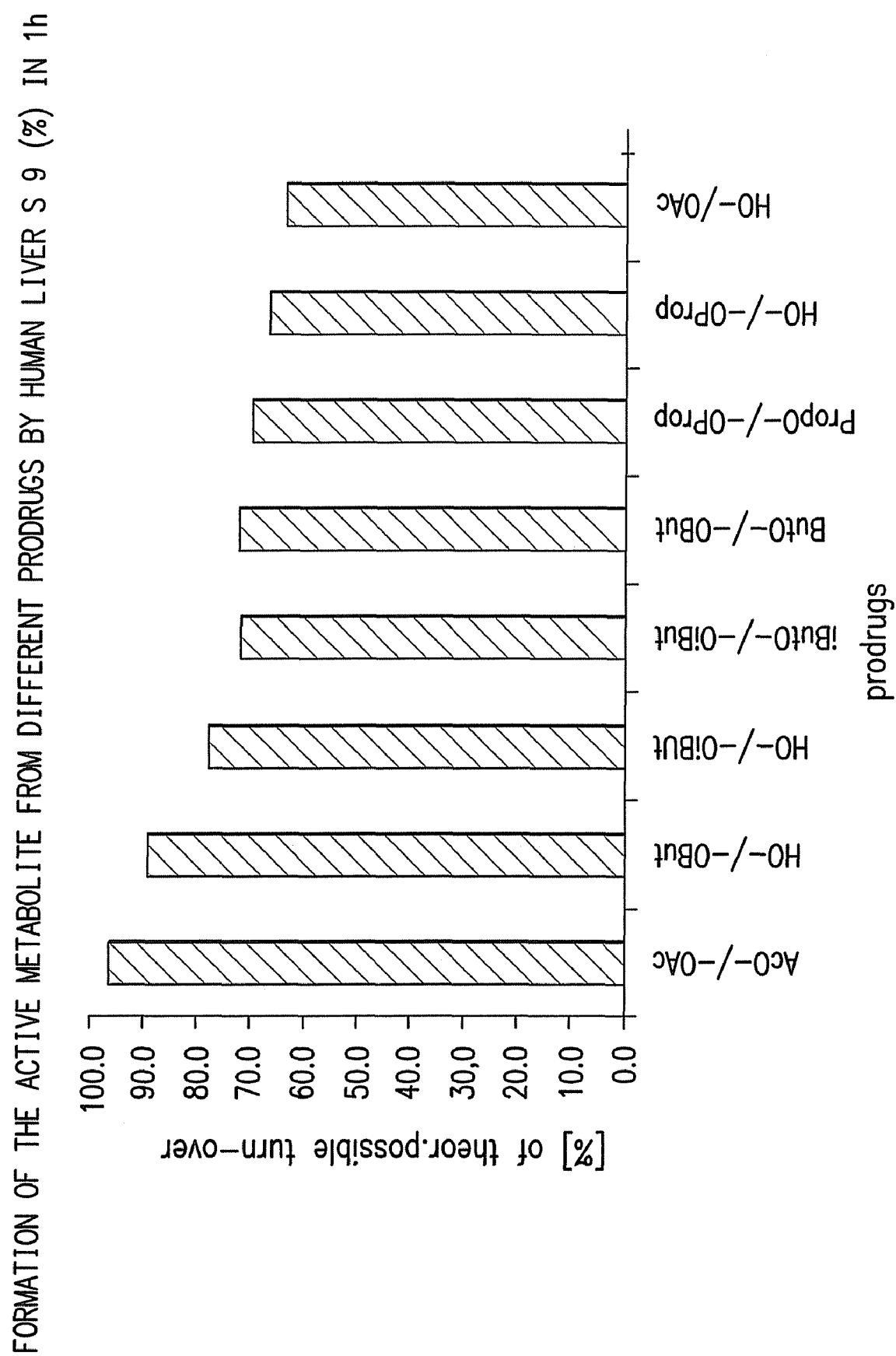

DERIVATIVES OF 3,3-DIPHENYLPROPYLAMINES

CROSS-REFERENCE TO RELATED APPLICATIONS

This application is a continuation of U.S. patent application Ser. No. 12/814,982, filed Jun. 14, 2010, now U.S. Pat. No. 7,985,772; which is a continuation of U.S. patent application Ser. No. 12/105,016, filed Apr. 17, 2008, now U.S. Pat. No. 7,855,230; which is a continuation of U.S. patent application Ser. No. 11/201,756, filed Aug. 10, 2005, now U.S. Pat. No. 7,384,980; which is a continuation of U.S. patent application Ser. No. 10/766,263, filed Jan. 27, 2004, now U.S. Pat. No. 7,230,030; which is a continuation of U.S. patent application Ser. No. 09/700,094, filed Jan. 2, 2001, now U.S. Pat. No. 6,713,464; which is a 371 of International Patent Application No. PCT/EP99/03212, filed May 11, 1999; which claims priority from European Patent Application No. 98108608.5, filed May 12, 1998. Each of these applications is hereby incorporated by reference herein in its entirety.

The present invention relates to novel derivatives of 3,3-diphenylpropylamines, methods for their preparation, pharmaceutical compositions containing the novel compounds, and the use of the compounds for preparing drugs.

In man, normal urinary bladder contractions are mediated mainly through cholinergic muscarinic receptor stimulation. There is reason to believe that muscarinic receptors mediate not only normal bladder contractions, but also the main part of the contractions in the overactive bladder resulting in symptoms such as urinary frequency, urgency and urge incontinence. For this reason, antimuscarinic drugs have been proposed for the treatment of bladder overactivity.

Among the antimuscarinic drugs available on the market, oxybutynin is currently regarded as the gold standard for pharmacological treatment of urge incontinence and other symptoms related to bladder overactivity. The effectiveness of oxybutynin has been demonstrated in several clinical studies, but the clinical usefulness of oxybutynin is limited due to antimuscarinic side effects. Dryness of the mouth is the most common experienced side effect which may be severe enough to result in poor compliance or discontinuation of treatment (Andersson, K.-E., 1988, Current concepts in the treatment of disorders of micturition, Drugs 35, 477-494; Kelleher et al. 1994).

Tolterodine is a new, potent and competitive, muscarinic receptor antagonist intended for the treatment of urinary urge incontinence and detrusor hyperactivity. Preclinical pharmacological data show that tolterodine exhibits a favourable tissue selectivity in vivo for the urinary bladder over the effect on the salivation (Nilvebrant et al., 1997, Tolterodine—a new bladder-selective antimuscarinic agent, Eur. J. Pharmacol. 327 (1997), 195-207), whereas oxybutynin exhibits the reversed selectivity. Tolterodine is equipotent to oxybutynin at urinary bladder muscarinic receptors and the favourable tissue selectivity of tolterodine demonstrated in the preclinical studies has been confirmed in clinical studies. Thus a good clinical efficacy has been combined with a very low number of incidences of dry mouth and antimuscarinic side effects.

A major metabolite of tolterodine, the 5-hydroxymethyl derivative is also a potent muscarinic receptor antagonist and the pharmacological in vitro and in vivo profiles of this metabolite are almost identical to those of tolterodine (Nilvebrant et al., 1997, Eur. J. Pharmacol. 327 (1997), 195-207). Combined pharmacological and pharmacokinetic data indicate that it is most likely that the metabolite gives a major contribution to the clinical effect in most patients.

WO 94/11337 proposes the active metabolite of tolterodine as a new drug for urge incontinence. Administration of the active metabolite directly to patients has the advantage compared to tolterodine that only one active principle (compound) has to be handled by the patient which normally should result in a lower variation in efficacy and side effects between patients and lower risk of interaction with other drugs.

However, the introduction of an additional hydroxy group in the tolterodine results in an increased hydrophilic property of the new compounds (3,3-diphenylpropylamines) compared to the parent compounds which normally results in a lower absorption/bioavailability, leading to pre-systemic side effects or interactions due to non-absorbed antimuscarinic drug. In a method to circumvent this disadvantage, different prodrugs of the metabolite have been synthesized and tested for their antimuscarinic activity, potential absorption through biological membranes and enzymatic cleavage.

It is an object of the present invention to provide novel derivatives of 3,3-diphenylpropylamines. It is a further object of the present invention to provide new derivatives of 3,3-diphenylpropylamines which will be more useful as prodrugs for treatment of urinary incontinence and other spasmogenic conditions that are caused by muscarinic mechanisms while avoiding the disadvantage of a too low absorption through biological membranes of the drugs or an unfavourable metabolism.

A further object of the invention is to provide novel prodrugs of antimuscarinic agents with superior pharmacokinetic properties compared to present drugs as oxybutynin and tolterodine, methods for preparing thereof, pharmaceutical compositions containing them, a method of using said compounds and compositions for the treatment of urinary incontinence, gastrointestinal hyperactivity (irritable bowel syndrome) and other smooth muscle contractile conditions.

According to the present invention, novel 3,3-diphenylpropyl-amines are provided, which are represented by the general formulae I and VII'

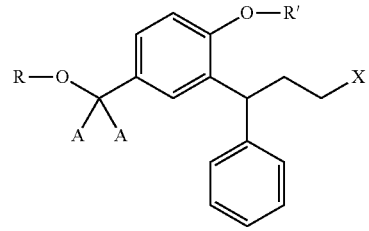

Formula I

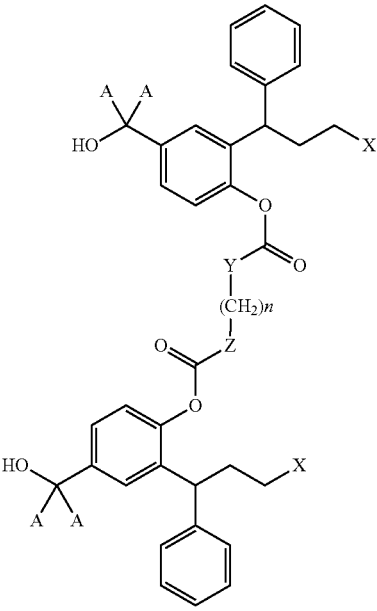

Formula VII' wherein R and R' are independently selected from
  a) hydrogen, $C_1$-$C_6$ alkyl, $C_3$-$C_{10}$ cycloalkyl, substituted or unsubstituted benzyl, allyl or carbohydrate; or
  b) formyl, $C_1$-$C_6$ alkylcarbonyl, cycloalkylcarbonyl, substituted or unsubstituted arylcarbonyl, preferably benzoyl; or
  c) $C_1$-$C_6$ alkoxycarbonyl, substituted or unsubstituted aryloxycarbonyl, benzoylacyl, benzoylglycyl, a substituted or unsubstituted amino acid residue; or
  d)

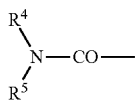

wherein $R^4$ and $R^5$ independently represent hydrogen, $C_1$-$C_6$ alkyl, substituted or unsubstituted aryl, preferably substituted or unsubstituted phenyl, benzyl or phenoxyalkyl wherein the alkyl residue has 1 to 4 carbon atoms and wherein $R^4$ and $R^5$ may form a ring together with the amine nitrogen; or
  e)

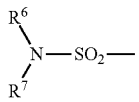

wherein $R^6$ and $R^7$ independently represent $C_1$-$C_6$ alkyl, substituted or unstubstituted aryl, preferably substituted or unsubstituted phenyl, benzyl or phenoxyalkyl wherein the alkyl residue has 1 to 6 carbon atoms; or
  f) an ester moiety of inorganic acids,
  g) —$SiR_aR_bR_c$, wherein $R_a$, $R_b$, $R_c$ are independently selected from $C_1$-$C_4$ alkyl or aryl, preferably phenyl,
  with the proviso that R' is not hydrogen, methyl or benzyl if R is hydrogen, R is not ethyl if R' is hydrogen,
  X represents a tertiary amino group of formula Ia Formula Ia

wherein $R^8$ and $R^9$ represent non-aromatic hydrocarbyl groups, which may be the same or different and which together contain at least three carbon atoms, and wherein $R^8$ and $R^9$ may form a ring together with the amine nitrogen,
  Y and Z independently represent a single bond between the $(CH_2)_n$ group and the carbonyl group, O, S or NH,
  A represents hydrogen ($^1H$) or deuterium ($^2H$),
  n is 0 to 12
and
  their salts with physiologically acceptable acids, their free bases and, when the compounds can be in the form of optical isomers, the racemic mixture and the individual enantiomers.

The aforementioned compounds can form salts with physiologically acceptable organic and inorganic acids. Furthermore, the aforementioned compounds comprise the free bases as well as the salts thereof. Examples of such acid addition salts include the hydrochloride and hydrobromide.

When the novel compounds are in the form of optical isomers, the invention comprises the racemic mixture as well as the individual isomers as such.

Preferably each of $R^8$ and $R^9$ independently signifies a saturated hydrocarbyl group, especially saturated aliphatic hydrocarbyl groups such as $C_{1-8}$-alkyl, especially $C_{1-6}$-alkyl, or adamantyl, $R^8$ and $R^9$ together comprising at least three, preferably at least four carbon atoms.

According to another embodiment of the invention, at least one of $R^8$ and $R^9$ comprises a branched carbon chain.

Presently preferred tertiary amino groups X in formula I include the following groups a) to h):

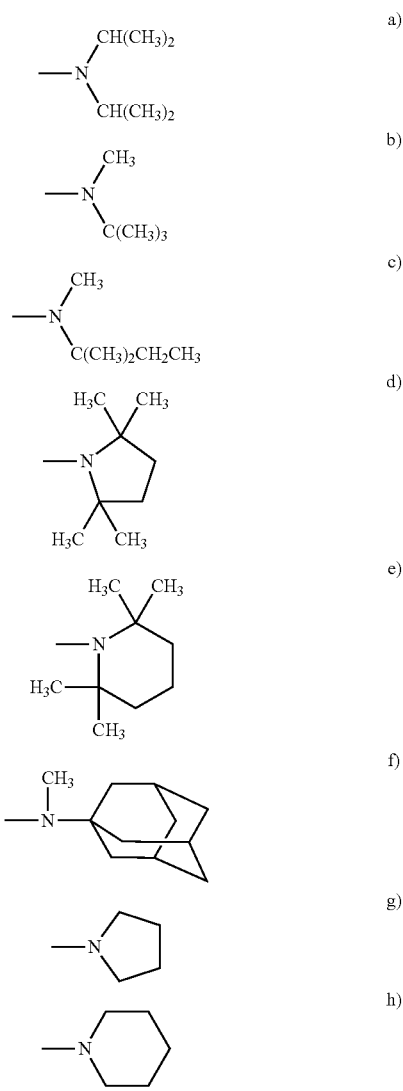

Group a) is particularly preferred.

The aforementioned tertiary amino groups X are described in WO 94/11337 and the compounds according to the present invention can be obtained by using the corresponding starting compounds.

BRIEF DESCRIPTION OF THE DRAWINGS

FIG. 1 shows the formation of the active metabolite from different prodrugs by human liver S 9(%) in 1 h.

In the compounds according to the present invention, the term "alkyl" preferably represents a straight-chain or branched-chain hydrocarbon group having 1 to 6 carbon atoms. Such hydrocarbon groups may be selected from methyl, ethyl, propyl, isopropyl, butyl, isobutyl, pentyl and hexyl. The term "cycloalkyl" denotes a cyclic hydrocarbon group having 3 to 10 carbon atoms which may be substituted conveniently.

The term "substituted or unsubstituted benzyl" denotes a benyl group —$CH_2$—$C_6H_5$ which is optionally substituted by one or more substituents on the phenyl ring. Suitable substituents are selected from alkyl, alkoxy, halogen and nitro. Suitable halogen atoms are fluorine, chlorine and iodine atoms. Preferred substituted benzyl groups are 4-methylbenzyl, 2-methylbenzyl, 4-methoxybenzyl, 2-methoxybenzyl, 4-nitrobenzyl, 2-nitrobenzyl, 4-chlorobenzyl and 2-chlorobenzyl.

In the compounds according to the present invention the term "$C_1$-$C_6$ alkylcarbonyl" denotes a group R—C(=O)— wherein R is an alkyl group as defined hereinbefore. Preferred $C_1$-$C_6$ alkylcarbonyl groups are selected from acetyl, propionyl, isobutyryl, butyryl, valeroyl and pivaloyl. The term "cyclo-alkylcarbonyl" denotes a group R—C(=O)— wherein R is a cyclic hydrocarbon group as defined hereinbefore. The same counts to the selected carbonyl groups.

The term "aryl" denotes an aromatic hydrocarbon group such as phenyl- ($C_6H_5$—), naphthyl- ($C_{10}H_7$—) and anthryl- ($C_{14}H_9$—). Preferred aryl groups according to the present invention are phenyl and naphthyl with phenyl being particularly preferred.

The term "benzoyl" denotes an acyl group of the formula —CO—$C_6H_5$ wherein the phenyl ring may have one or more substituents.

Preferred substituents of the aryl group and in particular of the phenyl group are selected from alkyl, alkoxy, halogen and nitro. As substituted benzoyl groups 4-methylbenzoyl, 2-methylbenzoyl, 4-methoxybenzoyl, 2-methoxybenzoyl, 4-chloro-benzoyl, 2-chlorobenzoyl, 4-nitrobenzoyl and 2-nitrobenzoyl may be mentioned.

The term "$C_1$-$C_6$ alkoxycarbonyl" refers to a group ROC(=O)— wherein R is an alkyl group as defined hereinbefore. Preferred $C_1$-$C_6$ alkoxycarbonyl groups are selected from $CH_3OC(=O)$—, $C_2H_5$—OC(=O)—, $C_3H_7OC(=O)$— and $(CH_3)_3COC(=O)$— and alicyclic alkyloxycarbonyl.

The term "amino acid residue" denotes the residue of a naturally occurring or synthetic amino acid. Particularly preferred amino acid residues are selected from the group consisting of glycyl, valyl, leucyl, isoleucyl, phenylalanyl, prolyl, seryl, threonyl, methionyl, hydroxyprolyl.

The amino acid residue may be substituted by a suitable group and as substituted amino acid residues, benzoylglycyl and N-acetylglycyl may be mentioned.

The term "carbohydrate" denotes the residue of a polyhydroxy aldehyde or polyhydroxy ketone of the formula $C_nH_{2n}O_n$ or $C_n(H_2O)_n$ and correponding carbohydrate groups are, for example, described in Aspinal, The Polysaccharides, New York: Academic Press 1982, 1983. A preferred carbohydrate group in the compounds according to the present invention is a glucuronosyl group, in particular a 1β-D-glucuronosyl group.

The term "LG" as used herein denotes a leaving group selected from halogenides, carboxylates and imidazolides.

The term "Bn" as used herein denotes a benzyl group.

Suitable ester moieties of inorganic acids may be derived from inorganic acids such as sulfuric acid and phosphoric acid.

Preferred compounds according to the present invention are:
A) Phenolic monoesters represented by the general formulae II and II'

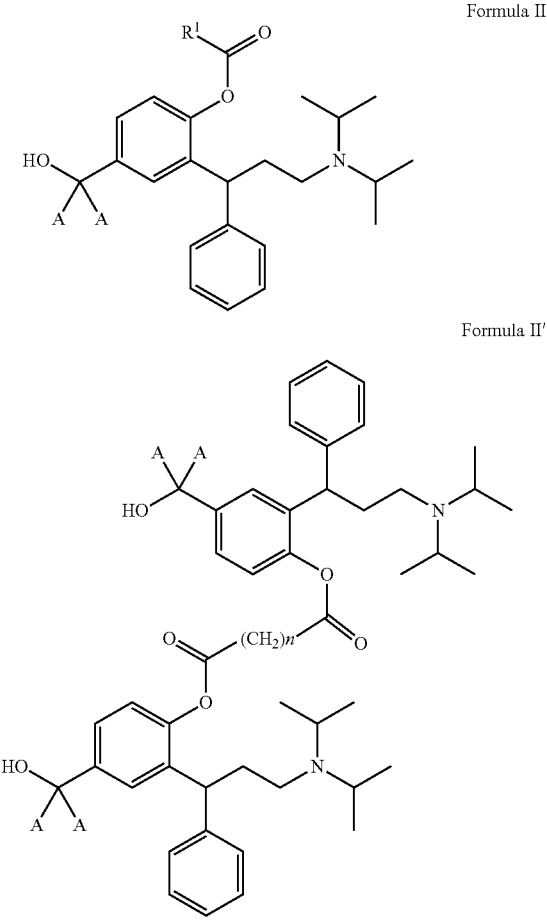

wherein $R^1$ represents hydrogen, $C_1$-$C_6$ alkyl or phenyl.
Particularly preferred phenolic monoesters are listed below:
(±)-formic acid 2-(3-diisopropylamino-1-phenylpropyl)-4-hydroxymethylphenyl ester,
(±)-acetic acid 2-(3-diisopropylamino-1-phenylpropyl)-4-hydroxymethylphenyl ester,
(±)-propionic acid 2-(3-diisopropylamino-1-phenylpropyl)-4-hydroxymethylphenyl ester,
(±)-n-butyric acid 2-(3-diisopropylamino-1-phenylpropyl)-4-hydroxymethylphenyl ester,
(±)-isobutyric acid 2-(3-diisopropylamino-1-phenylpropyl)-4-hydroxymethylphenyl ester,
R-(+)-isobutyric acid 2-(3-diisopropylamino-1-phenylpropyl)-4-hydroxymethylphenyl ester,
(±)-2,2-dimethylpropionic acid 2-(3-diisopropylamino-1-phenylpropyl)-4-hydroxymethylphenyl ester,
(±)-2-acetamidoacetic acid 2-(3-diisopropylamino-1-phenylpropyl)-4-hydroxymethylphenyl ester,
(±)-cyclopentanecarboxylic acid 2-(3-diisopropylamino-1-phenylpropyl)-4-hydroxymethylphenyl ester,
(±)-cyclohexanecarboxylic acid 2-(3-diisopropylamino-1-phenylpropyl)-4-hydroxymethylphenyl ester,
(±)-benzoic acid 2-(3-diisopropylamino-1-phenylpropyl)-4-hydroxymethylphenyl ester, R-(+)-benzoic acid 2-(3-diisopropylamino-1-phenyl-propyl)-4-hydroxymethylphenyl ester,
(±)-4-methylbenzoic acid 2-(3-diisopropylamino-1-phenyl-propyl)-4-hydroxymethylphenyl ester,
(±)-2-methylbenzoic acid 2-(3-diisopropylamino-1-phenyl-propyl)-4-hydroxymethylphenyl ester,
(±)-2-acetoxybenzoic acid 2-(3-diisopropylamino-1-phenyl-propyl)-4-hydroxymethylphenyl ester,
(±)-1-naphthoic acid 2-(3-diisopropylamino-1-phenylpropyl)-4-hydroxymethylphenyl ester,
(±)-2-naphthoic acid 2-(3-diisopropylamino-1-phenylpropyl)-4-hydroxymethylphenyl ester,
(±)-4-chlorobenzoic acid 2-(3-diisopropylamino-1-phenyl-propyl)-4-hydroxymethylphenyl ester,
(±)-4-methoxybenzoic acid 2-(3-diisopropylamino-1-phenylpropyl)-4-hydroxymethylphenyl ester,
(±)-2-methoxybenzoic acid 2-(3-diisopropylamino-1-phenylpropyl)-4-hydroxymethylphenyl ester,
(±)-4-nitrobenzoic acid 2-(3-diisopropylamino-1-phenylpropyl)-4-hydroxymethylphenyl ester,
(±)-2-nitrobenzoic acid 2-(3-diisopropylamino-1-phenylpropyl)-4-hydroxymethylphenyl ester,
(±)-malonic acid bis-[2-(3-diisopropylamino-1-phenylpropyl)-4-hydroxymethyl-phenyl]ester,
(±)-succinic acid bis-[2-(3-diisopropylamino-1-phenylpropyl)-4-hydroxymethyl-phenyl]ester,
(±)-pentanedioic acid bis-[2-(3-diisopropylamino-1-phenylpropyl)-4-hydroxymethyl-phenyl]ester,
(±)-hexanedioic acid bis-[2-(3-diisopropylamino-1-phenylpropyl)-4-hydroxymethyl-phenyl]ester.

B) Identical diesters represented by the general formula III

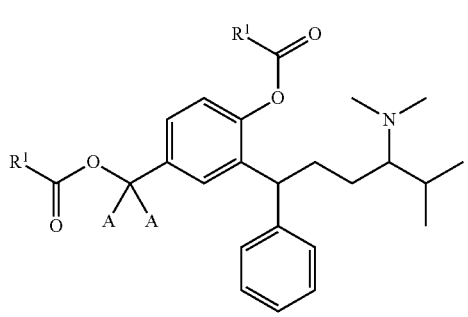

Formula III wherein $R^1$ is as defined above.

Particularly preferred identical diesters are listed below:
(±)-formic acid 2-(3-diisopropylamino-1-phenylpropyl)-4-formyloxymethylphenyl ester,
(±)-acetic acid 4-acetoxy-3-(3-diisopropylamino-1-phenyl-propyl)-benzyl ester,
(±)-propionic acid 2-(3-diisopropylamino-1-phenylpropyl)-4-propionyloxymethylphenyl ester,
(±)-n-butyric acid 4-n-butyryloxymethyl-2-(3-diisopropylamino-1-phenylpropyl)-phenyl ester,
(±)-isobutyric acid 2-(3-diisopropylamino-1-phenylpropyl)-4-isobutyryloxymethylphenyl ester,
(±)-2,2-dimethylpropionic acid 3-(3-diisopropylamino-1-phenylpropyl)-4-(2,2-dimethyl-propionyloxy)-benzyl ester,
(±)-benzoic acid 4-benzoyloxymethyl-2-(3-diisopropylamino-1-phenylpropyl)-phenyl ester,
R-(+)-benzoic acid 4-benzoyloxymethyl-2-(3-diisopropyl-amino-1-phenylpropyl)-phenyl ester,
(±)-pent-4-enoic acid 2-(3-diisopropylamino-1-phenylpropyl)-4-(pent-4-enoyloxymethyl)-phenyl ester,
cyclic oct-4-ene-1,8-dioate of Intermediate B,
cyclic octane-1,8-dioate of Intermediate B,
poly-co-DL-lactides of Intermediate B.

C) Mixed diesters represented by the general formula IV

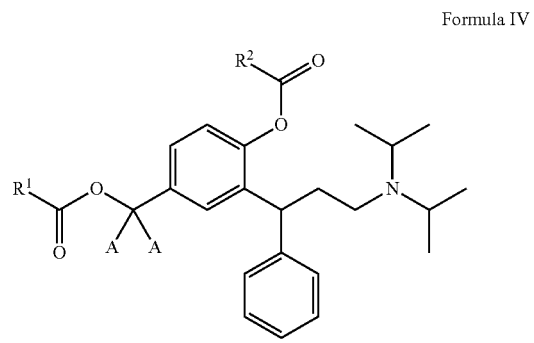

Formula IV wherein $R^1$ is as defined above
and
$R^2$ represents hydrogen, $C_1$-$C_6$ alkyl or phenyl
with the proviso that $R^1$ and $R^2$ are not identical.

Particularly preferred mixed diesters are listed below:
(±)-acetic acid 2-(3-diisopropylamino-1-phenylpropyl)-4-formyloxymethylphenyl ester,
(±)-benzoic acid 2-(3-diisopropylamino-1-phenylpropyl)-4-formyloxymethylphenyl ester,
(±)-benzoic acid 2-(3-diisopropylamino-1-phenylpropyl)-4-acetoxymethylphenyl ester,
R-(+)-benzoic acid 2-(3-diisopropylamino-1-phenylpropyl)-4-acetoxymethylphenyl ester,
(±)-isobutyric acid 4-acetoxymethyl-2-(3-diisopropylamino-1-phenylpropyl)-phenyl ester,
R-(+)-isobutyric acid 4-acetoxymethyl-2-(3-diisopropylamino-1-phenylpropyl)-phenyl ester,
(±)-2,2-dimethylpropionic acid 4-acetoxy-3-(3-diisopropylamino-1-phenylpropyl)-benzyl ester,
(±)-2,2-dimethylpropionic acid 4-acetoxymethyl-2-(3-diisopropylamino-1-phenylpropyl)-phenyl ester,
(±)-benzoic acid 4-benzyloxy-3-(3-diisopropylamino-1-phenylpropyl)-benzyl ester.

D) Benzylic monoesters represented by the general formula V

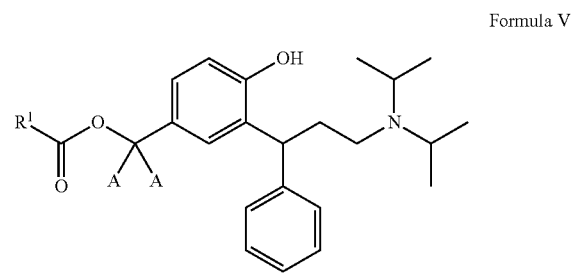

Formula V wherein $R^1$ is as defined above.

Particularly preferred benzylic monoesters are listed below:
(±)-formic acid 3-(3-diisopropylamino-1-phenylpropyl)-4-hydroxybenzyl ester,
(±)-acetic acid 3-(3-diisopropylamino-1-phenylpropyl)-4-hydroxybenzyl ester, (±)-propionic acid 3-(3-diisopropylamino-1-phenylpropyl)-4-hydroxybenzyl ester,
(±)-butyric acid 3-(3-diisopropylamino-1-phenylpropyl)-4-hydroxybenzyl ester,
(±)-isobutyric acid 3-(3-diisopropylamino-1-phenyl-propyl)-4-hydroxybenzyl ester,
(±)-2,2-dimethylpropionic acid 3-(3-diisopropylamino-1-phenylpropyl)-4-hydroxybenzyl ester,
(±)-benzoic acid 3-(3-diisopropylamino-1-phenylpropyl)-4-hydroxybenzyl ester.

E) Ethers and silyl ethers represented by the general formula VI

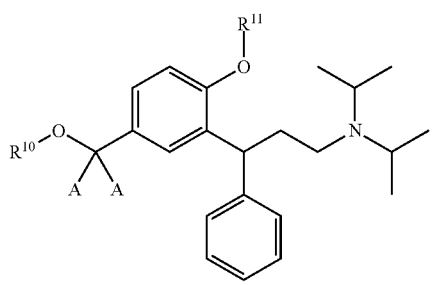

Formula VI wherein at least one of $R^{10}$ and is selected from $C_1$-$C_6$ alkyl, benzyl or —$SiR_aR_bR_c$ as defined above and the other one of $R^{10}$ and $R^{11}$ may additionally represent hydrogen, $C_1$-$C_6$ alkylcarbonyl or benzoyl.

Particularly preferred ethers and silyl ethers are listed below:
(±)-2-(3-diisopropylamino-1-phenylpropyl)-4-methoxy-methylphenol,
(±)-2-(3-diisopropylamino-1-phenylpropyl)-4-ethoxy-methylphenol,
(±)-2-(3-diisopropylamino-1-phenylpropyl)-4-propoxy-methylphenol,
(±)-2-(3-diisopropylamino-1-phenylpropyl)-4-isopropoxymethylphenol,
(±)-2-(3-diisopropylamino-1-phenylpropyl)-4-butoxy-methylphenol,
(±)-acetic acid 2-(3-diisopropylamino-1-phenylpropyl)-4-methoxymethylphenyl ester,
(±)-acetic acid 2-(3-diisopropylamino-1-phenylpropyl)-4-ethoxymethylphenyl ester,
(±)-2-(3-diisopropylamino-1-phenylpropyl)-4-trimethyl-silanyloxymethylphenol,
(±)-diisopropyl-[3-phenyl-3-(2-trimethylsilanyloxy-5-trimethylsilanyloxymethylphenyl)-propyl]-amine,
(±)-[3-(3-diisopropylamino-1-phenylpropyl)-4-trimethyl-silanyloxyphenyl]-methanol,
(±)-diisopropyl-[3-(5-methoxymethyl-2-trimethylsilanyloxyphenyl)-3-phenylpropylamine,
(±)-diisopropyl-[3-(5-ethoxymethyl-2-trimethylsilanyl-oxyphenyl)-3-phenylpropylamine,
(±)-[4-(tert.-butyl-dimethylsilanyloxy)-3-(3-diiso-propylamino-1-phenylpropyl)-phenyl]-methanol,
(±)-acetic acid 4-(tert.-butyl-dimethylsilanyloxy)-3-(3-diisopropylamino-1-phenylpropyl)-benzyl ester,
(±)-4-(tert.-butyl-dimethylsilanyloxy)-3-(3-diisopropylamino-1-phenylpropyl)-phenol,
(±)-acetic acid 4-(tert.-butyl-dimethylsilanyloxy)-2-(3-diisopropylamino-1-phenylpropyl)-phenyl ester,
(±)-{3-[2-(tert.-butyl-dimethylsilanyloxy)-5-(tert.-butyl-dimethylsilanyloxymethyl)-phenyl]-3-phenylpropyl}-diisopropylamine,
(±)-[4-(tert.-butyl-diphenylsilanyloxy)-3-(3-diisopropylamino-1-phenylpropyl)-phenyl]-methanol,
(±)-acetic acid 4-(tert.-butyl-diphenylsilanyloxymethyl)-2-(3-diisopropylamino-1-phenylpropyl)-phenyl ester,
(±)-4-(tert.-butyl-diphenylsilanyloxymethyl)-2-(3-diisopropylamino-1-phenylpropyl)-phenol,
(±)-{3-[2-(tert.-butyl-diphenylsilanyloxy)-5-(tert.-butyl-diphenylsilanyloxymethyl)-phenyl]-2-phenylpropyl}-diisopropylamine,
(±)-acetic acid 4-benzyloxy-3-(3-diisopropylamino-1-phenylpropyl)-benzyl ester,
(±)-benzoic acid 4-benzyloxy-3-(3-diisopropylamino-1-phenylpropyl)-benzyl ester,
(±)-isobutyric acid 4-benzyloxy-3-(3-diisopropylamino-1-phenylpropyl)-benzyl ester,
(±)-2-(3-diisopropylamino-1-phenylpropyl)-4-(1β-D-glucuronosyloxymethyl)-phenol.

F) Carbonates and carbamates represented by the general formulae VII and VIII

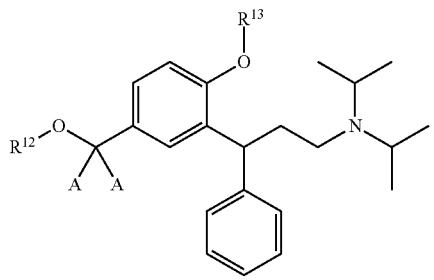

Formula VII

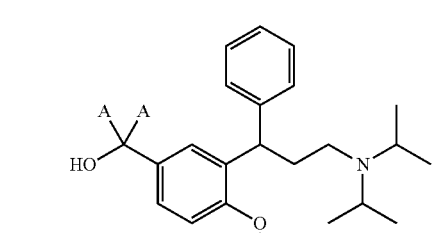

Formula VIII

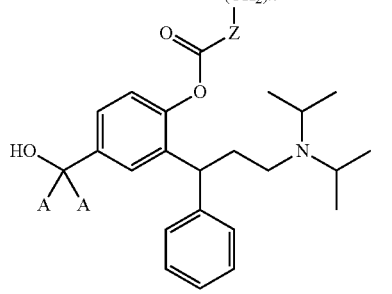

wherein Y, Z and n are as defined above and wherein $R^{12}$ and $R^{13}$ represent a $C_1$-$C_6$ alkoxycarbonyl group or

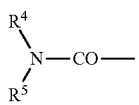

wherein $R^4$ and $R^5$ are as defined above.

Particularly preferred carbonates and carbamates are listed below:
- (±)-N-ethylcarbamic acid 2-(3-diisopropylamino-1-phenylpropyl)-4-hydroxymethylphenyl ester,
- (±)-N,N-dimethylcarbamic acid 2-(3-diisopropylamino-1-phenylpropyl)-4-hydroxymethylphenyl ester,
- (±)-N,N-diethylcarbamic acid 2-(3-diisopropylamino-1-phenylpropyl)-4-hydroxymethylphenyl ester,
- (±)-N-phenylcarbamic acid 2-(3-diisopropylamino-1-phenylpropyl)-4-hydroxymethylphenyl ester,
- (±)-[2-(3-Diisopropylamino-1-phenylpropyl)-4-hydroxymethyl-phenoxycarbonylamino]acetic acid ethyl ester hydrochloride,
- (±)-N-ethylcarbamic acid 3-(3-diisopropylamino-1-phenylpropyl)-4-N-ethylcarbamoyloxybenzyl ester,
- (±)-N,N-dimethylcarbamic acid 3-(3-diisopropylamino-1-phenylpropyl)-4-N,N-dimethylcarbamoyloxybenzyl ester,
- (±)-N,N-diethylcarbamic acid 3-(3-diisopropylamino-1-phenylpropyl)-4-N,N-diethylcarbamoyloxybenzyl ester,
- (±)-N-phenylcarbamic acid 3-(3-diisopropylamino-1-phenylpropyl)-4-N-phenylcarbamoyloxybenzyl ester,
- (±)-{4-[2-(3-diisopropylamino-1-phenylpropyl)-4-hydroxymethylphenoxycarbonylamino]-butyl}-carbamic acid 2-(3-diisopropylamino-1-phenylpropyl)-4-hydroxymethylphenyl ester,
- (±)-carbonic acid 2-(3-diisopropylamino-1-phenylpropyl)-4-hydroxymethylphenyl ester ethyl ester,
- (±)-carbonic acid 2-(3-diisopropylamino-1-phenylpropyl)-4-hydroxymethylphenyl ester phenyl ester,
- (±)-carbonic acid 2-(3-diisopropylamino-1-phenylpropyl)-4-ethoxycarbonyloxymethylphenyl ester ethyl ester,
- (±)-carbonic acid 2-(3-diisopropylamino-1-phenylpropyl)-4-phenoxycarbonyloxymethylphenyl ester phenyl ester.

G) 3,3-Diphenylpropylamines selected from
(i) compounds of the formulae IX and IX'

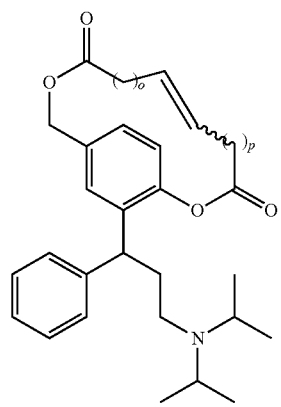

Formula IX

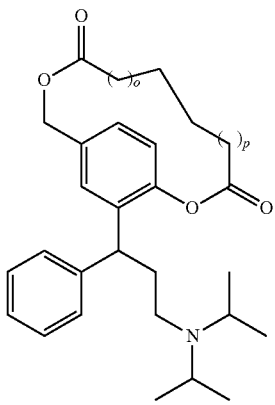

Formula IX' wherein o and p are the same or different and represent the number of methylene units $-(CH_2)-$ and may range from 0 to 6, (ii) (±)-Benzoic acid 2-(3-diisopropylamino-1-phenylpropyl)-4-sulphooxymethyl-phenyl ester (iii) Poly-co-DL-lactides of 2-(3-diisopropylamino-phenylpropyl)-4-hydroxymethyl-phenol (iv) (±)-2-(3-Diisopropylamino-1-phenylpropyl)-4-(1β-D-glucuronosyloxymethyl)-phenol having the formula

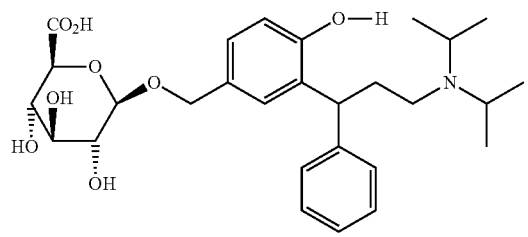

and
their salts with physiologically acceptable acids, their free bases and, when the compounds can be in the form of optical isomers, the racemic mixture and the individual enantiomers.

The present invention, moreover, relates to processes for the preparation of the aforementioned compounds. In particular, according to the present invention, the following processes are provided:

A process for the production of phenolic monoesters represented by the general formula II

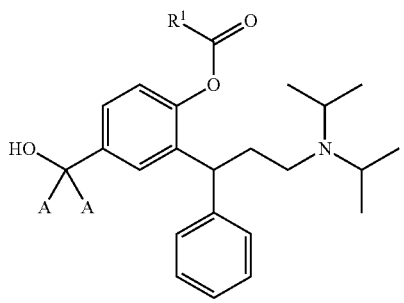

Formula II as defined above, which comprises treatment of a compound of the formula

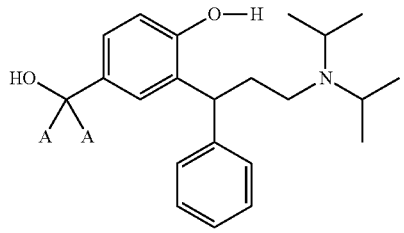

with an equivalent of an acylating agent selected from

wherein LG represents a leaving group selected from halogenide, carboxylate and imidazolide and $R^1$ is as defined above, in an inert solvent in the presence of a condensating agent.

Preferably, the acylating agent is selected from

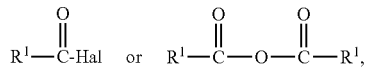

wherein Hal represents a halogen atom, preferably a chlorine atom, and $R^1$ is as defined above.

A process for the production of phenolic monoesters represented by the general formula II'

Formula II'

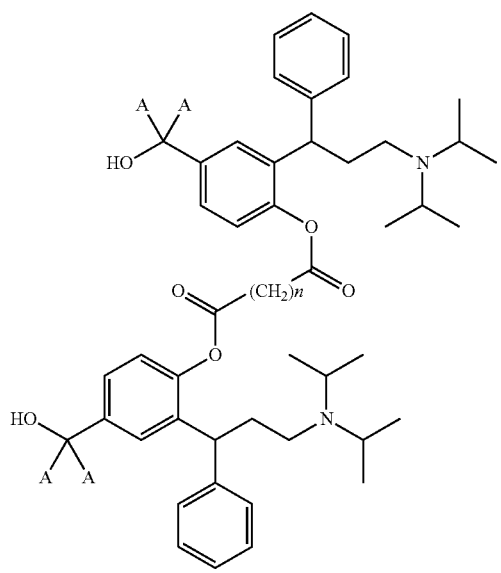

as defined above, which comprises treatment of two equivalents of a compound of the formula

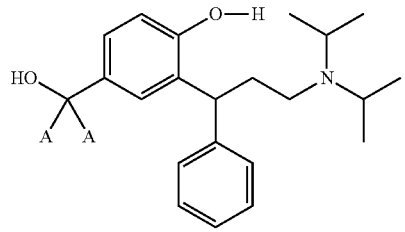

with an acylating agent selected from

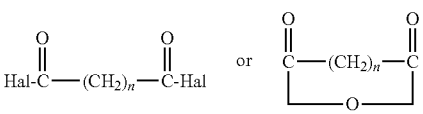

wherein Hal represents a halogen atom, preferably a chlorine atom.

Hence, in these processes, an Intermediate B having the formula

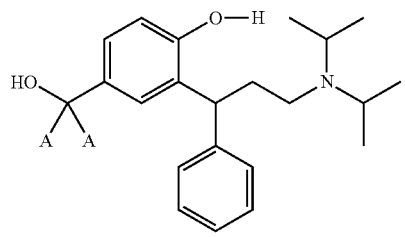

is treated with an equivalent of an acylating agent (e.g. an acyl halogenite or acyl anhydride) in an inert solvent and in the presence of a condensating agent (e.g. amine) to provide phenolic monoesters of formula II or formula II' (wherein n is 0-12), respectively, if polyfunctional acylating agents (e.g. acid halides, preferably acid chlorides of dicarboxylic acids) are used.

The Intermediate B as used in the processes for the production of the 3,3-diphenylpropylamines according to the present invention can be in the form of a racemic mixture or of optically active compounds in accordance with the formulae shown below:

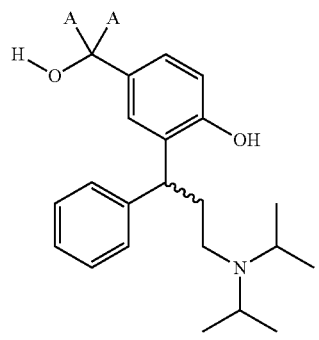

Intermediate RS

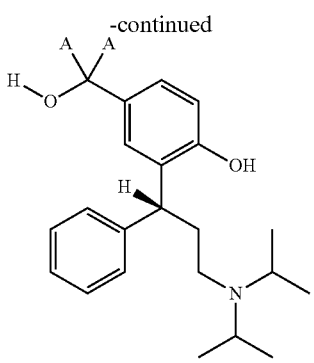

Intermediate R-(+)

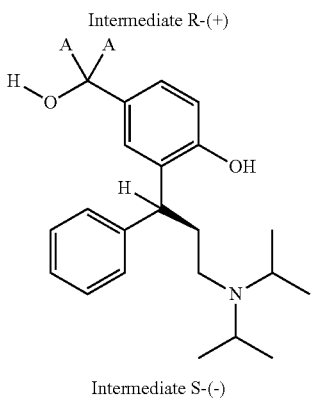

Intermediate S-(-)

Alternatively, structures of formula II or II' may be obtained by regioselective deprotection of a protected benzylic hydroxy group (chemically or enzymatically: T. W. Greene, P. G. M. Wuts, "*Protective Groups in Organic Chemistry*", 2nd Ed., J. Wily & Sons, New York 1991).

The identical diesters represented by the general formula III

Formula III

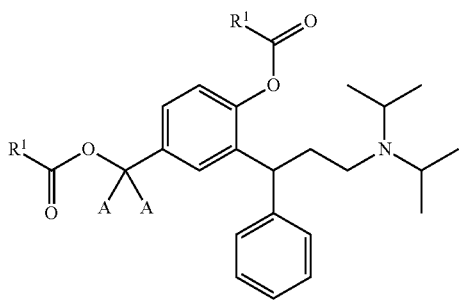

as defined above can be prepared by a process which comprises treatment of a compound of the formula

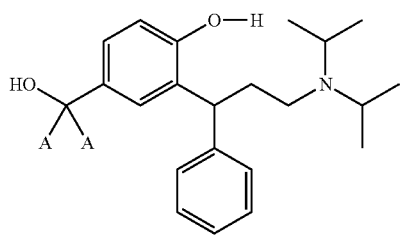

with at least two equivalents of the acylating agent $R^1$—C(=O)-LG as defined above.

Thus, the aforementioned di-acyl compounds are readily accessible if an at least two-molar excess of an acylating agent is used in the above-mentioned conversion of Intermediate B or, more general, on treatment of compounds of formula I with acylating agents in the presence of suitable catalysts. In the above process, the following Intermediate A

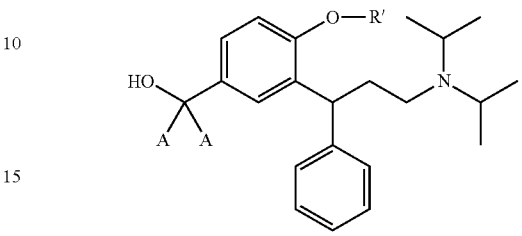

wherein R' denotes a benzyl group can be used instead of Intermediate B. The Intermediate A can be used in the form of a racemic mixture or of optically active compounds (similar to Intermediate B).

Benzylic monoestes represented by the general formula V

Formula V

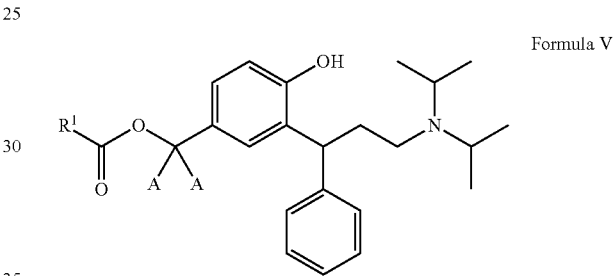

wherein $R^1$ is as defined above can be prepared by a process which comprises treatment of a compound of the formula

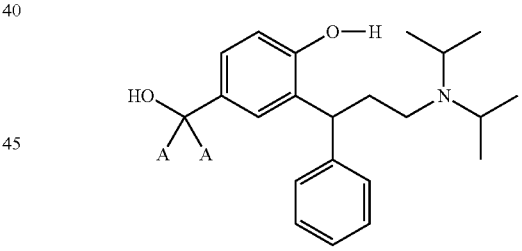

at room temperature and under anhydrous conditions with activated esters in the presence of enzymes selected from lipases or esterases.

Hence, this process relates to the preparation of phenols with para acyloxymethyl substituents (cf. formula V). These compounds can be prepared in several chemical steps from intermediates such as formula I, where R represents hydrogen and R' is hydrogen or any suitable protective group which can be removed by known methods (T. W. Greene, P. G. M. Wuts, "*Protective Groups in Organic Chemistry*", 2nd Ed., J. Wily & Sons, New York 1991) in the presence of the newly introduced substituent $R^1CO$. It was found, however, that the benzylic substituent $R^1CO$ can be introduced more conveniently and in only one step if Intermediate B is treated at room temperature and under anhydrous conditions with activated esters (e.g. vinyl acylates, isopropenyl acylates) in the presence of enzymes such as lipases or esterases.

The mixed diesters represented by the general formula IV

Formula IV

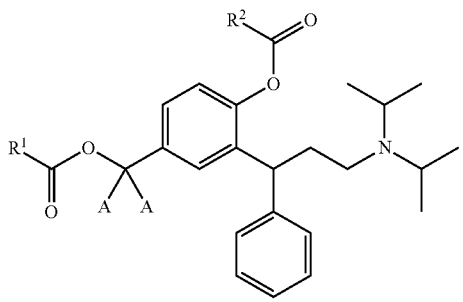

wherein $R^1$ and $R^2$ are as defined above can be prepared by a process which comprises acylation of the above-mentioned benzylic monoester represented by the general formula V Formula V

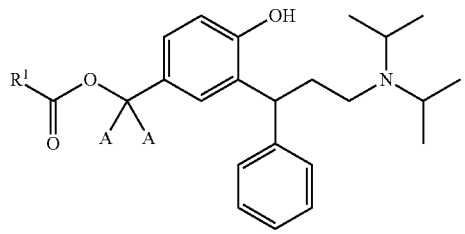

wherein $R^1$ is as defined above or of a phenolic monoester represented by the general formula II Formula II

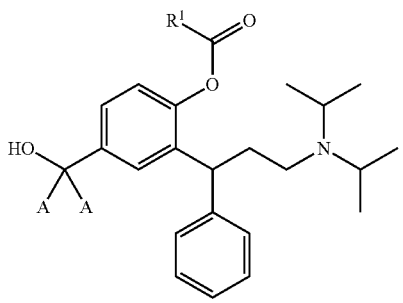

as defined hereinbefore.

In general, mixed diesters of formula IV can be obtained by acylation of compounds of the general formula I wherein R and $R^1$ are different substituents selected from the group consisting of hydrogen, acyl residues or protecting groups that are cleavable under the acylation reaction conditions.

Ethers represented by the general formula VI

Formula VI

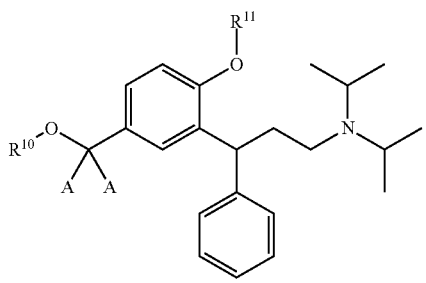

as defined hereinbefore wherein $R^{11}$ is hydrogen can be prepared by a process which comprises reacting a compound of the formula

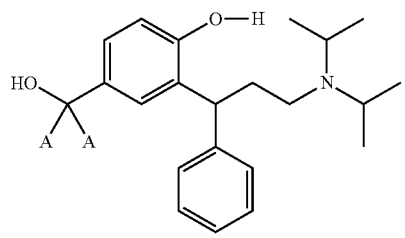

with an alcohol $R^{10}$—OH in the presence of an esterification catalyst.

A further process for the preparation of ethers represented by the general formula VI Formula VI

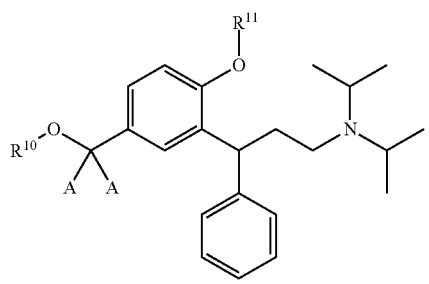

wherein $R^{10}$ and $R^{11}$ are as defined hereinbefore, comprises acid or base treatment of free benzylic alcohols selected from

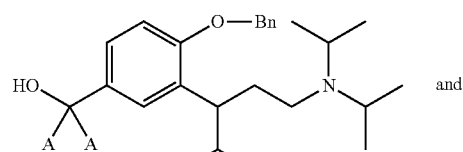

and

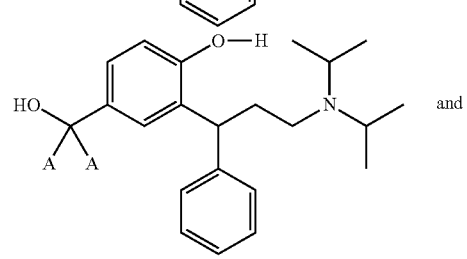

and

Formula II

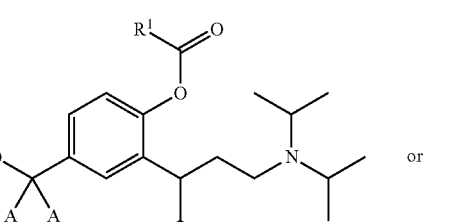

or

Formula VI

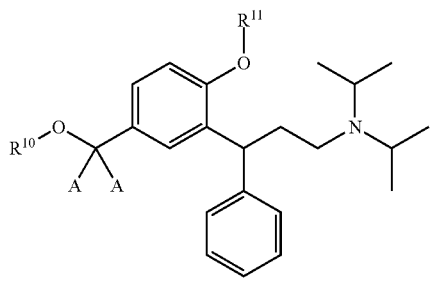

wherein R¹⁰ is hydrogen and R¹¹ is as defined above or

Formula VII

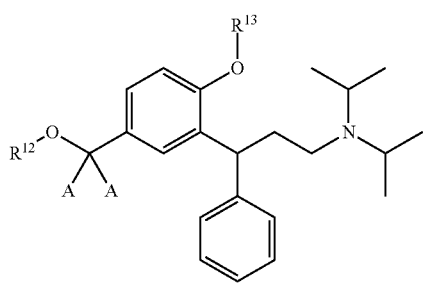

wherein R¹² is hydrogen and R¹³ represents a $C_1$-$C_6$ alkoxycarbonyl group or $$\begin{array}{c} R^4 \\ | \\ N-CO- \\ | \\ R^5 \end{array}$$

wherein R⁴ and R⁵ are as defined above
or of benzylic acylates selected from

Formula III

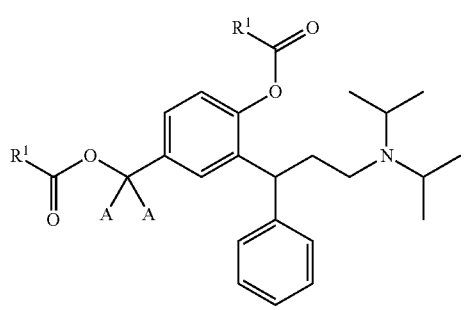

Formula IV

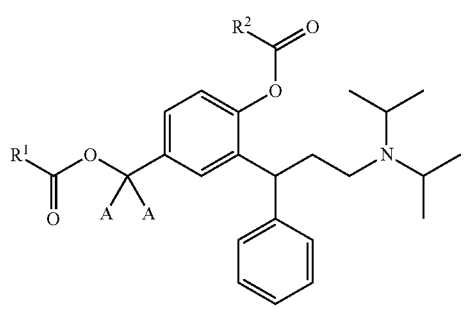

Formula V

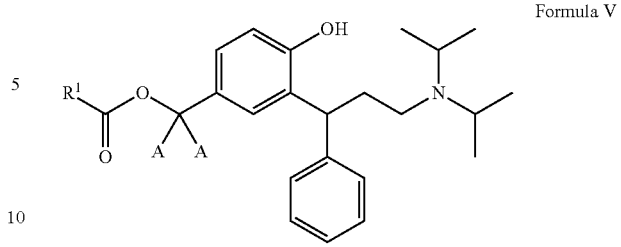

wherein R¹ and R² are as defined hereinbefore in the presence of suitable hydroxy reagents.

Finally, ethers of formula VI can be prepared by a process which comprises treating a compound of the formula

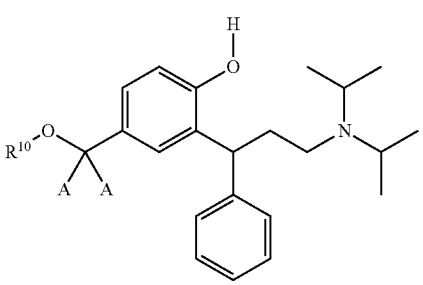

wherein R¹⁰ is as defined above with an alkylating agent selected from alkyl halogenides, alkyl sulphates and alkyl triflates, said alkyl group having 1 to 6 carbon atoms.

In summary, regioselective modification of the benzylic hydroxy groups is achieved either by acid or base treatment of benzylic acylates in the presence of suitable hydroxy reagents (e.g. alcohols) or by catalytic ether formation as described in the literature for other benzylic substrates (J. M. Saa, A. Llobera, A. Garcia-Raso, A. Costa, P. M. Deya; J. Org. Chem. 53: 4263-4273 [1988]). Both free benzylic alcohols such as Intermediates A and B or compounds of formulas II or VI (in which R¹⁰ is hydrogen) or formula VII (in which R¹² is hydrogen) as well as benzylic acylates such as formulae III, IV, V may serve as starting materials for the preparation of benzylic ethers (B. Loubinoux, J. Miazimbakana, P. Gerardin; Tetrahedron Lett. 30: 1939-1942 [1989]).

Likewise the phenolic hydroxy groups are readily transformed into phenyl ethers (R¹¹=alkyl) using alkylating agents such as e.g. alkyl halogenides, alkyl sulphates, alkyl triflates or employing Mitsunobu type reaction conditions (Synthesis 1981, 1-28). Similarly, both phenolic and alcoholic monosilyl ethers are obtained by regioselective silylation or by desilylation of bis-silyl ethers of Intermediate B as described for other compounds in the literature (J. Paladino, C. Guyard, C. Thurieau, J.-L. Fauchere, Helv. Chim. Acta 76: 2465-2472 [1993]; Y. Kawazoe, M. Nomura, Y. Kondo, K. Kohda, Tetrahedron Lett. 26: 4307-4310 [1987]).

Carbonates and carbamates represented by the general formulae VII and VIII

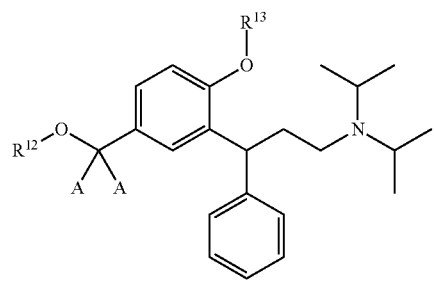
Formula VII

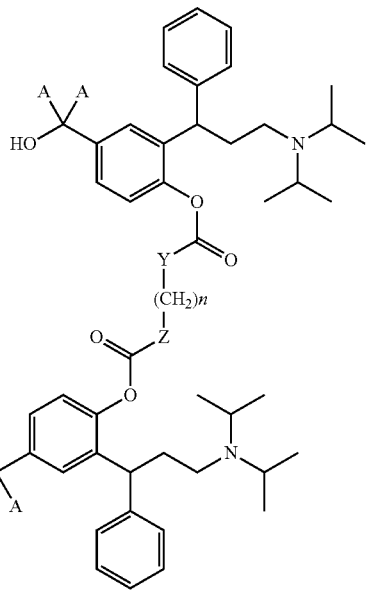
Formula VIII as defined hereinbefore can be prepared by a process which comprises reacting a compound selected from the group consisting of

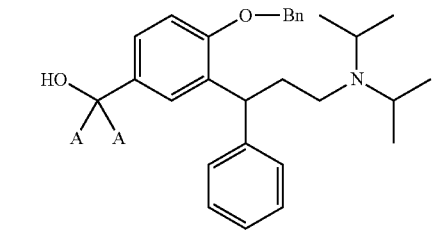

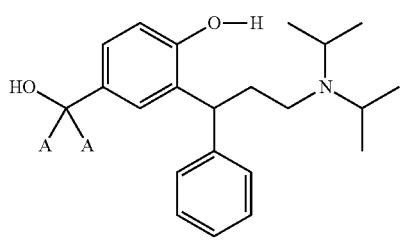

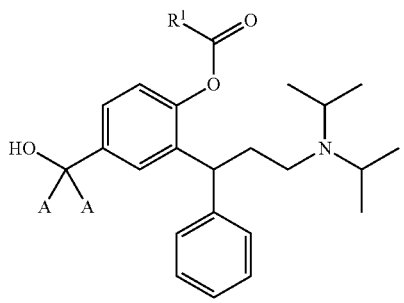
Formula II

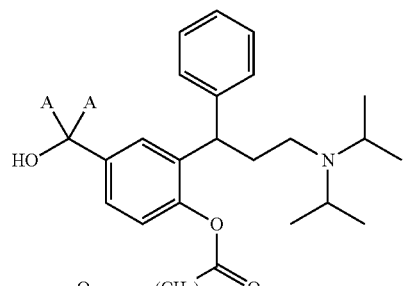
Formula II'

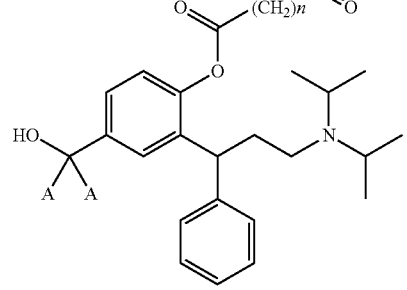

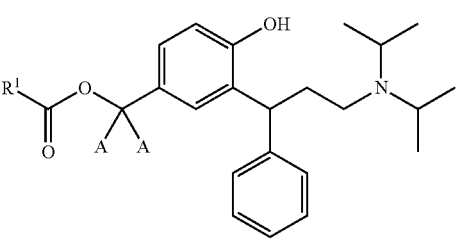
Formula V

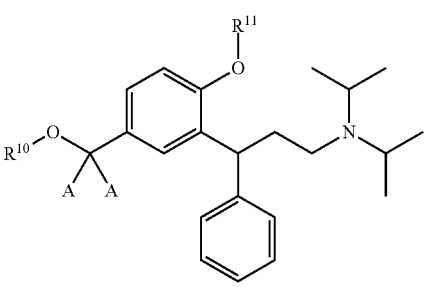
Formula VI wherein $R^1$ is defined as above, n is 0 to 12, Bn is benzyl, one of $R^{10}$ or $R^{11}$ is hydrogen and the other one is as defined above with activated carbonyl compounds or carbonyl precursor reagents selected from haloformates, ketenes, activated esters, mixed anhydrides of organic or inorganic acids, isocyanates and isothiocyanates.

The coupling reactions can be carried out in inert solvents over periods of several hours at temperatures from −10° C. to the refluxing temperature of the solvent or reagent used to provide compounds of the general formula VII where $R^{12}$ represents hydrogen, alkyl, aliphatic or aromatic acyl, or carbamoyl, and $R^{13}$ represents —C(=O)—Y—$R^3$, wherein Y and $R^3$ represent O, S, NH and alkyl or aryl, respectively. Polyfunctional reagents give the corresponding derivatives. For example, diisocyanates or di-carbonylchlorides provide compounds of formula VIII where X, Y have the meaning of O, S, or NH and n is zero to twelve.

The invention, moreover, relates to pharmaceutical compositions comprising one or more of the aforementioned 3,3-di-phenylpropylamines. In other words, the compounds according to the present invention can be used as pharmaceutically active substances, especially as antimuscarinic agents.

They can be used for preparing pharmaceutical formulations containing at least one of said compounds.

The compounds according to the present invention in the form of free bases or salts with physiologically acceptable acids, can be brought into suitable galenic forms, such as compositions for oral use, for injection or for nasal spray administration, in accordance with accepted pharmaceutical procedures. Such pharmaceutical compositions according to the invention comprise an effective amount of the compounds of claims 1 to 15 in association with compatible pharmaceutically acceptable carrier materials, or diluents, as is well known in the art. The carriers may be any inert material, organic or inorganic, suitable for enteral, percutaneous or parenteral administration, such as water, gelatine, gum arabicum, lactose, microcrystalline cellulose starch, sodium starch glycolate, calcium hydrogen phosphate, magnesium stearate, talcum and colloidal silicon dioxide. Such compositions may also contain other pharmaceutically active agents, and conventional additives, such as stabilizers, wetting agents, emulsifiers, flavouring agents and buffers.

The composition according to the invention can e.g. be made up in solid or liquid form for oral administration, such as tablets, capsules, powders, syrups and elixirs in the form of sterile solutions, suspensions or emulsions for parenteral administration.

The compounds according to the invention may be used in a patch formulation. The compounds can be administered transdermally with a reduced incidence of side effects and improved individual compliance.

The compounds and compositions can, as mentioned above, be used for the treatment of urinary incontinence and other spasmogenic conditions that are caused by muscarinic mechanisms. The dosage of the specific compound will vary depending on its potency, the mode of administration, the age and weight of the patient and the severity of the condition to be treated. The daily dosage may, for example, range from about 0.01 mg to about 5 mg, adminstered singly or multiply in doses e.g. from about 0.05 mg to about 50 g each.

The invention will be further illustrated by the following non-limiting examples and pharmacological tests.

I. Experimental

1. General

All compounds were fully characterized by $^1$H and $^{13}$C NMR spectroscopy (Bruker DPX 200). The chemical shifts reported for $^{13}$C NMR spectra (50 MHz, ppm values given) refer to the solvents CDCl$_3$ (77.10 ppm), dideuterio dichloromethane (CD$_2$Cl$_2$, 53.8 ppm), CD$_3$OD (49.00 ppm) or hexadeuterio dimethylsulphoxide (DMSO-d$_6$, 39.70 ppm), respectively. $^1$H NMR data (200 MHz, ppm) refer to internal tetramethylsilane).

Thin-layer chromatography (tlc, $R_f$ values reported) was conducted on precoated 5×10 cm E. Merck silica gel plates (60F254), spots were visualized by fluorescence quenching or spaying with alkaline potassium permanganate solution. Solvent systems: (1), ethyl acetate/n-hexane (30/70, v/v-%); (2), toluene/acetone/methanol/acetic acid (70/5/20/5, v/v-%); (3), n-hexane/acetone/diethylamine (70/20/10, v/v-%); (4), n-hexane/acetone/triethylamine (70/20/10, v/v-%); (5), ethyl acetate/n-hexane/2-propanol/triethylamine (60/40/20/1, v/v-%); (6), ethyl acetate/triethylamine (90/10, v/v-%); (7), cyclohexane/acetone/acetic acid (80/20/0.5, v/v-%). Optical rotations were measured at 589.3 nm and room temperature on a Perkin Elmer Polarimeter Type 241.

Melting points (mp) reported are uncorrected and were determined on a Mettler FP 1 instrument.

IR spectra were taken from a Perkin-Elmer FTIR spectrometer Series 1610, resolution 4 cm$^{-1}$.

Gas chromatography-mass spectrometry (GC-MS): spectra (m/z values and relative abundance (%) reported) were recorded on a Finnigan TSQ 700 triple mass spectrometer in the positive (P-CI) or negative (N-CI) chemical ionization mode using methane or ammonia as reactant gas. Hydroxylic compounds were analyzed as their trimethylsilyl ether derivatives. Combined liquid chromatography-mass spectrometry (LC-MS): Waters Integrety System, Thermabeam Mass Detector (EI, 70 eV), m/z values and relative abundance reported.

2. Synthesis of Intermediates A and B

3-Phenylacrylic acid 4-bromophenyl ester

An ice-cooled solution of 4-bromophenol (69.2 g) and cinnamoyl chloride (66.8 g) in dichloromethane (150 ml) was treated with triethylamine (40.6 g). After stirring for 18 hrs at room temperature the mixture was washed with water (250 ml), 1 M aqueous HCl, and dried over anhydrous sodium sulphate. Evaporation in vacuum left solid 3-phenylacrylic acid 4-bromophenyl ester (121.0 g, 99.8% yield), m.p. 113.3° C., tlc: (1) 0.83. NMR(CDCl$_3$): 116.85, 118.87, 123.49, 128.38, 129.06, 130.90, 132.49, 134.02, 147.07, 149.84, 165.06.

(±)-6-Bromo-4-phenylchroman-2-one

A portion of the ester (60.0 g) was dissolved in a mixture of acetic acid (60 ml) and concentrated sulphuric acid (18 ml) and refluxed for 2 hrs. After cooling, the reaction mixture was poured into ice water and the product was isolated by extraction with ethylacetate. Evaporation of the solvent and recrystallization of the residue from boiling ethanol (150 ml) yielded 26.3 g (43.8% yield) of pure, crystalline (±)-6-bromo-4-phenylchroman-2-one, m.p. 117.8° C., tlc: (1) 0.67. NMR (CDCl$_3$): 36.56, 40.51, 117.29, 118.87, 127.47, 127.89, 128.33, 129.32, 131.07, 131.79, 139.42, 150.76, 166.84.

(±)-3-(2-Benzyloxy-5-bromophenyl)-3-phenylpropionic acid methyl ester

A suspension consisting of (±)-6-bromo-4-phenylchroman-2-one (85.0 g), anhydrous potassium carbonate (46.7 g), sodium iodide (20.5 g) and benzyl chloride (40.6 g) in methanol (350 ml) and acetone (350 ml) was refluxed for 3 hrs. After evaporation of the solvents the residue was extracted with diethyl ether (2×300 ml) and the extract was washed with water (2×200 ml) and aqueous sodium carbonate. Drying (Na$_2$SO$_4$) and rotoevaporation left 121.8 g (102.1% crude yield) of (±)-3-(2-benzyloxy-5-bromophenyl)-3-phenylpropionic acid methyl ester as a light yellow oil, tlc: (1) 0.77; NMR (CDCl$_3$): 39.22, 40.53, 51.63, 70.16, 113.10, 113.77, 126.46, 126.92, 127.88, 128.08, 128.34, 128.45, 130.31, 130.55, 134.41, 136.44, 142.37, 154.94, 172.08.

(±)-3-(2-Benzyloxy-5-bromophenyl)-3-phenylpropionic acid

A solution of (±)-3-(2-benzyloxy-5-bromophenyl)-3-phenyl-propionic acid methyl ester (0.391 g, 0.92 mmol) in ethanol (5 ml) was treated at 50° C. with excess aqueous sodium hydroxide solution until the milky emulsion became clear. The reaction mixture was then acidified (pH 3), evaporated and extracted with dichloromethane. The organic extract was evaporated and the remaining oil was redissolved in a minimum of boiling ethanol. The precipitation formed after 18 hrs at 4° C. was filtered off and dried in vacuo to yield 0.27 g (71.4%) of (±)-3-(2-Benzyloxy-5-bromophenyl)-3-phenyl-propionic acid, colourless crystals, m.p. 124.9° C.; tlc: (1) 0.15 (starting material methyl ester 0.75); NMR (CDCl$_3$): 39.15, 40.26, 70.25, 113.21, 113.90, 126.62, 127.27, 127.98, 128.17, 128.47, 128.54, 130.46, 130.68, 134.34, 136.45, 142.16, 154.95, 177.65. LC-MS: 412/410 (14/11%, M$^+$·), 394/392 (15/13%), 321/319 (17/22%), 304/302 (17/21%), 259 (24%), 194 (22%), 178 (21%), 167 (65%), 152 (49%), 92 (100%). IR (KBr): 3434, 3030, 1708, 1485, 1452, 1403, 1289, 1243, 1126, 1018, 804, 735, 698, 649. Calculated for C$_{22}$H$_{19}$BrO$_3$ (mol-wgt. 411.30): C, 64.25%, H, 4.66%, Br 19.43%, O 11.67%. found: C, 63.72%, H, 4.70%, Br 19.75%, O 11.80%.

Alternatively, the crude reaction mixture from the above described synthesis of (±)-3-(2-benzyloxy-5-bromophenyl)-3-phenylpropionic acid methyl ester was evaporated, redissolved in warm ethanol, and treated with excess aqueous potassium hydroxide solution. Acidification to pH 3 (conc. hydrochloric acid) and cooling to 4° C. resulted in the formation of a solid, which was filtered off after 18 hrs, washed repeatedly with water and dried to yield (±)-3-(2-benzyloxy-5-bromo-phenyl)-3-phenylpropionic acid in 82% yield.

a) Resolution of 3-(2-benzyloxy-5-bromophenyl)-3-phenylpropionic acid

R-(−)-3-(2-Benzyloxy-5-bromophenyl)-3-phenylpropionic acid

Warm solutions of (±)-3-(2-benzyloxy-5-bromophenyl)-3-phenyl-propionic acid (815.6 g, 1.85 mol) and 1S,2R-(+)-ephedrine hemihydrate (232.1 g, 1.85 mol) in 2000 ml and 700 ml, respectively, of absolute ethanol were combined and then allowed to cool to 0° C. The precipitate formed was collected, washed with cold ethanol and dried in vacuum to give 553.2 g of the ephedrinium salt of the title compound (m.p. 153° C., e.e. 65% as determined by NMR and HPLC).

The salt was recrystallized twice from boiling ethanol to give R-(−)-3-(2-benzyloxy-5-bromophenyl)-3-phenylpropionic acid 1S,2R-(+)-ephedrinium salt in 75% yield, colourless crystalls, m.p. 158.6° C., e.e. 97.6% (HPLC). NMR (CDCl$_3$): 9.53, 30.90, 41.54, 42.83, 61.45, 70.15, 70.42, 113.05, 113.68, 125.89, 126.03, 127.33, 127.85, 128.19, 128.28, 128.45, 129.86, 130.70, 135.91, 136.65, 140.40, 144.09, 155.20, 178.94.

1.2 g (2.0 mmol) of the ephedrinium salt were dissolved in a mixture of acetone (5 ml) and ethanol (10 ml). After treatment with water (0.4 ml) and conc. (37%) aqueous hydrochloric acid (0.34 ml), the solution was evaporated in vacuum, and the residue was redissolved in 1M aqueous hydrochloric acid (2 ml) and dichloromethane (10 ml). The organic phase was separated, washed twice with water (2 ml), and evaporated to dryness to give R-(−)-3-(2-Benzyloxy-5-bromophenyl)-3-phenyl-propionic acid as a colourless oil which slowly solidified (0.4 g, 98% yield), m.p. 105.6° C. (from ethyl acetate/n-heptane); tlc: (7) 0.21; [α]$_D^{20}$=21.1 (c=1.0, ethanol), e.e. 99.9% (HPLC). NMR: identical with the racemic acid.

S-(+)-3-(2-Benzyloxy-5-bromophenyl)-3-phenylpropionic acid

The combined mother liquids from the above resolution and recrystallizations were treated under stirring and cooling (18° C.) with excess conc. aqueous hydrochloric acid. The precipitate (ephedrinium hydrochloride) was filtered off, and the filtrate was evaporated to dryness. The residue was redissolved in dichloromethane (1.5 liter) and then washed with several portions of 1 M aqueous hydrochloric acid followed by water. After drying (Na$_2$SO$_4$), filtration, and evaporation 479 g of crude S-(+)-3-(2-benzyloxy-5-bromophenyl)-3-phenyl-propionic acid were obtained as a yellow viscous oil. The pure S-(+)enantiomeric acid was converted into the 1R,2S-(−)-ephedrine salt as described above for the R-(−) acid. Two recrystallizations from boiling ethanol provided colourless crystals of S-(+)-3-(2-benzyloxy-5-bromophenyl)-3-phenyl-propionic acid 1R,2S-(−)-ephedrinium salt in 83% yield, m.p. 158.7° C., e.e. 97.8% (HPLC). NMR (CDCl$_3$): 9.47, 30.85, 41.54, 42.92, 61.48, 70.13, 70.30, 113.04, 113.66, 125.89, 126.01, 127.32, 127.84, 128.18, 128.44, 129.83, 130.68, 135.94, 136.63, 140.44, 144.13, 155.19, 178.94.

S-(+)-3-(2-Benzyloxy-5-bromophenyl)-3-phenylpropionic acid was obtained in quantitative yield from this ephedrinium salt by the method described above for the R-(−)acid, tlc: (7) 0.20, e.e. (NMR)>99%, mp 105.5° C.; [α]$_D^{20}$=+22.6 (c=1.0, ethanol); NMR: identical with the racemic acid.

b) Enantioselective Synthesis of R-(−)- and S-(+)-3-(2-benzyloxy-5-bromophenyl)-3-phenylpropionic acid

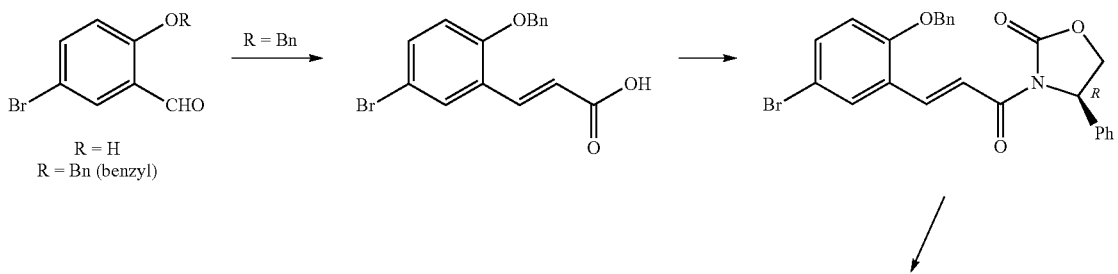

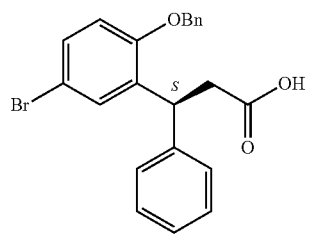 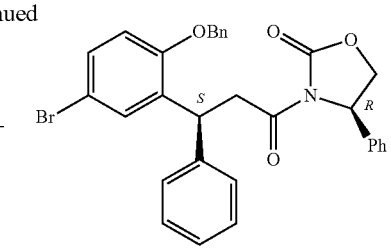

2-Benzyloxy-5-bromobenzaldehyde

To a solution of 0.1 mol of 5-bromo-2-benzaldehyde in THF (150 ml) was added 0.1 mol of $K_2CO_3$ and 0.11 mol of benzyl bromide. The mixture was refluxed for 2 hrs and water (500 ml) was added. After addition of ethyl acetate (400 ml) and stirring the organic layer was washed with water, dried (sodium sulphate) and evaporated to dryness. The resulting slightly yellow solid of pure (tlc) 2-benzyloxy-5-bromo-benzaldehyde was used as such in the next step.

3-(2-Benzyloxy-5-bromophenyl)-acrylic acid

A mixture of 2-benzyloxy-5-bromobenzaldehyde (0.10 mol), malonic acid (15.0 g), and piperidine (2.0 ml) in 150 ml of pyridine was first heated at 90° C. for 90 min and subsequently refluxed for 0.5 hrs. After cooling to room temperature, the reaction was poured on a mixture of ice (1 kg) and concentrated aqueous hydrochloric acid (250 ml). The solid material that precipitated after stirring for 2 hrs. was collected by suction and recrystallized from a minimum of boiling methanol.

3-[3-(2-Benzyloxy-5-bromophenyl)-acryloyl]-(4R)-4-phenyl-oxazolidin-2-one

Pivaloylchloride (7 g) was added dropwise at −30° C. to a stirred solution of 3-(2-benzyloxy-5-bromophenyl)-acrylic acid (50.0 mmol) and triethylamine (15.0 ml) in 200 ml of tetrahydrofuran. After an additional hour the temperature was lowered to −50° C. and (R)-2-phenyloxazolidin-2-one (9.0 g) and lithium chloride (2.5 g) were added in one portion. The cooling bath was then removed and stirring was continued over 18 hrs. The reaction was diluted with water and 3-[3-(2-benzyl-oxy-5-bromophenyl)-acryloyl]-(4R)-4-phenyloxazolidin-2-one was isolated by extraction with ethyl acetate.

3-[3-(2-Benzyloxy-5-bromophenyl)-(3S)-3-phenylpropionyl]-(4R)-4-phenyloxazolidin-2-one To a precooled (−30° C.) mixture of copper-(I) chloride (21.0 g) and dimethylsulfide (45 ml) in dry tetrahydrofuran (150 ml) was added dropwise an ethereal solution of phenylmagnesiumbromide (0.3 mol). The mixture was stirred 20 min at the same temperature and then cooled to −40° C. A solution of 3-[3-(2-Benzyloxy-5-bromophenyl)-acryloyl]-(4R)-4-phenyl-oxazolidin-2-one (50.0 mmol) in dry tetrahydrofuran (150 ml) was added during 10 min. The cooling bath was removed and stirring was continued for 18 hrs. The mixture was quenched with half-saturated aqueous ammonium chloride solution and the product was isolated by extraction with ethyl acetate.

S-(+)-3-(2-Benzyloxy-5-bromophenyl)-3-phenylpropionic acid

A solution of the above described 3-[3-(2-benzyloxy-5-bromo-phenyl)-(3S)-3-phenylpropionyl]-(4R)-4-phenyloxazolidin-2-one in tetrahydrofuran (300 ml) and water (100 ml) was cooled to 0° C. and then treated with 30% aqueous hydrogen peroxide (20 ml) followed by solid lithium hydroxide (4.3 g). Water was added after 2 hrs and the chiral auxiliary was removed by extraction with ethyl acetate. The aqueous phase was acidified with aqueous hydrochloric acid (10%) and crude S-(+)-3-(2-benzyloxy-5-bromophenyl)-3-phenylpropionic acid was extracted with tert.-butyl-methylether.

HPLC analysis (Chiralpak AD, mobile phase hexane/2-propanol/trifluoro acetic acid [92:8:0.1, vol/vol-%]; flow 1.0 ml/min, detection 285 nm) indicated an enantiomeric ratio 93:7 (retention times 14.8 min and 11.5 min, respectively). The e.e. of 86% of the S-(+) enantiomer can be improved to >98.5% by recrystallization of the diastereomeric salts using "nitromix" (Angew. Chem. Int. Ed. Engl. 1998, Vol. 37, p. 2349) or (1R,2S)-(−)-ephedrine hemihydrate as described above. The S-(+)-3-(2-benzyloxy-5-bromophenyl)-3-phenyl-propionic acid was isolated after acidification of aqueous solutions of the diastereomeric salts. It forms colourless crystals which gave an optical rotation of $[\alpha]_D^{22}=+21.6$ (c=0.5, MeOH).

R-(−)-3-(2-Benzyloxy-5-bromophenyl)-3-phenylpropionic acid

Conjugate organocuprate addition of phenylmagnesiumbromide to 3-[3-(2-benzyloxy-5-bromophenyl)-acryloyl]-(4S)-4-phenoyloxazolidin-2-one as described above for the S-(+)enantiomer gave crystalline R-(−)-3-(2-benzyloxy-5-bromophenyl)-3-phenylpropionic acid in an e.e. of 99.6% after two recrystallizations, $[\alpha]_D^{22}=-21.7$ (c=0.5, MeOH).

c) Synthesis of the R- and S-Enantiomers of Intermediate B (i) Phenylpropanol Route

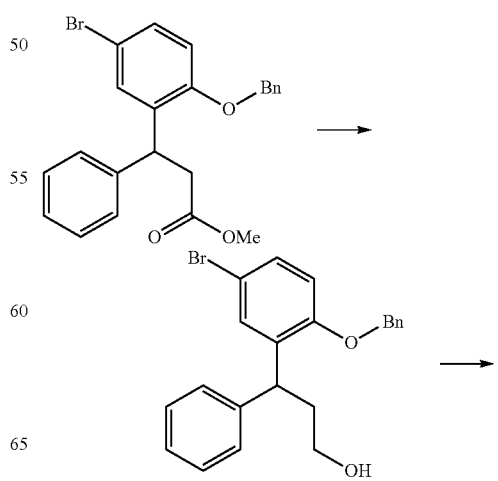

-continued

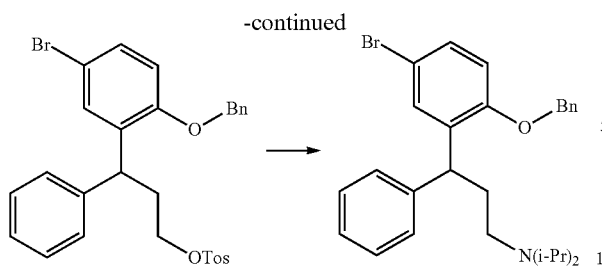

(±)-3-(2-Benzyloxy-5-bromophenyl)-3-phenylpropan-1-ol

A solution of the methyl(±)-propionate (121.0 g) in 350 ml of dry tetrahydrofuran was slowly added under an atmosphere of nitrogen to a suspension of lithium aluminiumhydride (7.9 g) in tetrahydrofuran (350 ml). After stirring at room temperature for 18 hrs, 20% aqueous HCl was added dropwise and the product was isolated by repeated extraction with diethyl ether. The combined extracts were gradually washed with hydrochloric acid, sodium hydroxide solution, distilled water, and then dried ($Na_2SO_4$) to give a light yellow viscous oil (108.8 g, 96.3% yield) after evaporation which gradually crystallized, m.p. 73.8° C., tlc: (1) 0.47, (±)-3-(2-benzyloxy-5-bromophenyl)-3-phenylpropan-1-ol. NMR ($CDCl_3$): 37.52, 39.52, 60.84, 70.54, 113.54, 113.83, 126.29, 127.30, 127.51, 129.99, 128.24, 128.38, 129.99, 130.88, 135.69, 136.40, 143.53, 155.12.

The same product was obtained after reduction of (±)-3-(2-benzyloxy-5-bromophenyl)-3-phenylpropionic acid with lithium aluminium hydride in tetrahydrofuran (30 min, 25° C.), 31% yield.

(±)-Toluene-4-sulphonic acid 3-(2-benzyloxy-5-bromophenyl)-3-phenylpropyl ester

A cooled (5° C.) solution of (±)-3-(2-benzyloxy-5-bromophenyl)-3-phenylpropan-1-ol (108.0 g) in dichloromethane (300 ml) was treated with pyridine (79.4 ml) and then p-toluenesulphonyl chloride (60.6 g) in dichloromethane (200 ml). After 18 hrs. at room temperature the solvent was removed in vacuum and the residue was extracted with diethyl ether. The extract was washed with hydrochloric acid, water, and dried over anhydrous sodium sulphate to give (±)-toluene-4-sulphonic acid 3-(2-benzyloxy-5-bromophenyl)-3-phenylpropyl ester as a light yellow oil after concentration under reduced pressure (140.3 g, 93.6% yield), tlc: (1) 0.66. NMR ($CDCl_3$): 21.67, 33.67, 39.69, 68.58, 70.28, 113.21, 113.76, 126.47, 127.84, 128.10, 128.25, 128.41, 128.51, 129.81, 130.26, 130.42, 132.91, 134.39, 136.41, 142.16, 155.07.

(±)-[3-(2-Benzyloxy-5-bromophenyl)-3-phenylpropyl]-diiso-propylamine

A solution of the (±)-toluenesulphonate((±)-toluene-4-sulphonic acid 3-(2-benzyloxy-5-bromophenyl)-3-phenylpropyl ester, 139.3 g) in acetonitrile (230 ml) and N,N-diisopropylamine (256 g) was refluxed for 97 hrs. The reaction mixture was then evaporated to dryness and the residue thus formed was partitioned between diethyl ether (500 ml) and aqueous sodium hydroxide (2 M, 240 ml). The organic phase was washed twice with water (250 ml) and then extracted with 1 M sulphuric acid. The aqueous phase was adjusted to about pH 12-13 and reextracted with ether (500 ml). The organic phase was washed with water, dried ($Na_2SO_4$) and evaporated to provide (±)-[3-(2-benzyloxy-5-bromophenyl)-3-phenylpropyl]-diisopropylamine as a brown and viscous syrup (94.5 g, 77.9% yield), tlc: (2) 0.49. NMR ($CDCl_3$): 20.65, 20.70, 36.70, 41.58, 43.78, 48.77, 70.24, 113.52, 126.02, 127.96, 128.20, 128.36, 129.82, 130.69, 136.34, 136.76, 144.20, 155.15.

(ii) Phenylpropionamide Route

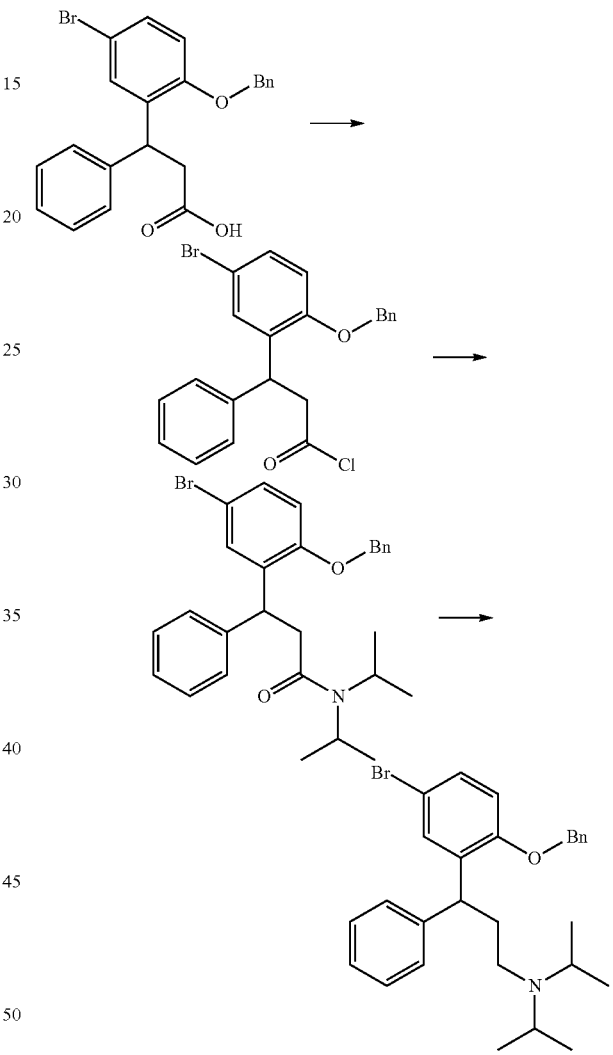

S-(+)-3-(2-Benzyloxy-5-bromophenyl)-3-phenylpropionyl chloride

Thionylchloride (4.5 g, 2.8 ml, 37.8 mmol) and some drops of dimethylformamide were added to a solution of S-(+)-3-(2-benzyloxy-5-bromophenyl)-3-phenylpropionic acid (10.3 g, 25 mmol) in ethyl acetate (60 ml). The mixture was refluxed until tlc control indicated complete consumption of the starting material (2 hrs). Evaporation in vacuum gave the acid chloride as a light yellow liquid in almost quantitative yield (10.7 g). Conversion of an aliquot to the methyl ester showed a single spot in tlc ($R_f$ 0.54, solvent system (7)).

S-(+)-N,N-Diisopropyl-3-(2-benzyloxy-5-bromophenyl)-3-phenylpropionamide

A solution of S-(+)-3-(2-benzyloxy-5-bromophenyl)-3-phenylpropionyl chloride (9.6 g, 22.3 mmol) in ethyl acetate (40 ml) was added dropwise to a stirred and cooled (3° C.) solution of diisopropylamine (6.4 g, 49.0 mmol) in 60 ml of ethyl acetate. The reaction was stirred for 18 hrs at room temperature and then washed with water, aqueous hydrochloric acid (1 M) and half saturated brine. The organic phase was dried (sodium sulphate) and evaporated to dryness. The colourless oily residue (10.7 g, 97% yield) of S-(+)-N,N-diisopropyl-3-(2-benzyloxy-5-bromophenyl)-3-phenylpropionamide showed a single spot on tlc: ($R_f$ 0.70 (4)). NMR (CDCl$_3$): 18.42, 20.46, 20.63, 20.98, 39.51, 41.44, 45.76, 48.63, 70.00, 112.84, 113.64, 126.10, 126.45, 127.34, 127.78, 128.20, 128.36. 129.93, 130.59, 135.18, 136.52, 143.52, 155.17, 169.61.

(±)-N,N-Diisopropyl-3-(2-benzyloxy-5-bromophenyl)-3-phenylpropionamide

The amide was prepared from diisopropylamine and the racemic acid chloride as described above for the S-(+)enantiomer. The viscous colourless oil was dissolved in ethanol and the solution stored at −30° C. From this solution colourless crystals were obtained, m.p. 101.8° C.

(±)-[3-(2-Benzyloxy-5-bromophenyl)-3-phenylpropyl]-diiso-propylamine

To a stirred solution of (±)-N,N-diisopropyl-3-(2-benzyloxy-5-bromophenyl)-3-phenylpropionamide (11.8 g) in 40 ml of dry tetrahydrofuran was added 1 M lithium aluminium hydride/tetrahydrofuran (36 ml). The reaction was refluxed for 4 hrs and then quenched with the dropwise addition of water. After removal of the precipitate the solvent was evaporated and the oily residue dissolved in diluted sulphuric acid. The aqueous phase was washed several times with diethyl ether, adjusted to pH 10-12 (aqueous NaOH), and extracted with diethyl ether. The extract was dried (sodium sulphate), filtered and evaporated to dryness in vacuum to leave 8.1 g (76.7%) of the title compound as a viscous colourless oil, tlc: (4) 0.86. The NMR spectrum corresponds to the product, obtained from the tosylate precursor (see above).

S-(+)-[3-(2-Benzyloxy-5-bromophenyl)-3-phenylpropyl]-diiso-propylamine

Repetition of the reaction sequence by using S-(+)-3-(2-benzyloxy-5-bromophenyl)-3-phenylpropionic acid as the starting material gave S-(+)-[3-(2-Benzyloxy-5-bromophenyl)-3-phenylpropyl]-diisopropylamine as a viscous colourless oil, $[\alpha]_D^{22}$=+18.5 (c=10.0, ethanol), e.e. of a representative batch 99.4%

R-(−)-[3-(2-Benzyloxy-5-bromophenyl)-3-phenylpropyl]-diiso-propylamine

Repetition of the reaction sequence by using R-(−)-3-(2-benzyloxy-5-bromophenyl)-3-phenylpropionic acid as the starting material gave R-(−)-[3-(2-Benzyloxy-5-bromophenyl)-3-phenylpropyl]-diisopropylamine as a viscous colourless oil, $[\alpha]_D^{22}$=−17.3 (c=10.0, ethanol), e.e. of a representative batch 98.3%.

The optical purities were determined by chiral HPLC using Chiralpak OD columns.

(±)-4-Benzyloxy-3-(3-diisopropylamino-1-phenylpropyl)-benzoic acid hydrochloride An ethereal Grignard solution, prepared from the above (±)-amine (22.8 g), ethyl bromide (17.4 g) and magnesium (6.1 g) under an atmosphere of nitrogen was diluted with dry tetrahydrofuran (200 ml) and then cooled to −60° C. Powdered solid carbon dioxide (ca. 50 g) was then added in small portions and the green reaction mixture was warmed to room temperature. After the addition of an aqueous solution of ammonium chloride (200 ml, 10%) and adjustment of the aqueous phase to pH 0.95, a white solid was recovered by filtration to provide (±)-4-benzyloxy-3-(3-diisopropylamino-1-phenylpropyl)-benzoic acid hydrochloride (14.7 g, 64.3% yield), m.p. 140° C. (dec.), tlc: (2) 0.33. NMR (CD$_3$OD): 17.07, 18.77, 33.55, 43.27, 56.50, 71.50, 112.89, 124.10, 127.94, 129.07, 129.25, 129.34, 129.59, 129.66, 130.18, 131.60, 132.78, 137.60, 143.30, 161.11, 169.70.

(±)-[4-Benzyloxy-3-(3-diisopropylamino-1-phenylpropyl)-phenyl]-methanol

Intermediate A (n=1)

The (±)-hydrochloride was converted into its methyl ester (MeOH, trace sulphuric acid, 6h reflux) and the free oily base thus obtained (28 g; tlc (2): $R_f$ 0.46) was dissolved in dry diethyl ether (230 ml). This solution was slowly (2 h) dropped under a nitrogen atmosphere to a suspension of lithium aluminium hydride (1.8 g) in ether (140 ml). After stirring for 18 hrs, the reaction was quenched by the addition of water (4.7 ml). The organic phase was dried over anhydrous sodium sulphate, filtered and evaporated to dryness to provide (±)-[4-benzyloxy-3-(3-diisopropylamino-1-phenylpropyl)-phenyl]-methanol (26 g, 98.9% yield), as an oil which gradually crystallized, m.p. 86.4° C., tlc: (2) 0.32. NMR (CDCl$_3$): 20.53, 20.61, 36.87, 41.65, 44.14, 48.82, 65.12, 70.09, 111.80, 125.77, 125.97, 126.94, 127.55, 128.08, 128.37, 128.44, 133.27, 134.05, 134.27, 137.21, 144.84.

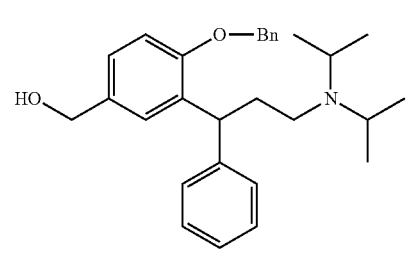

Intermediate A

(±)-[4-Benzyloxy-3-(3-diisopropylamino-1-phenylpropyl)-phenyl]-[C$^2$H]methanol Intermediate d$_2$-A (n=2)

Repetition of the above described reduction of the methylester of (±)-4-benzyloxy-3-(3-diisopropylamino-1-phenylpropyl)-benzoic acid by the use of lithium aluminium deuteride gave (±)-[4-benzyloxy-3-(3-diisopropylamino-1-phenylpropyl)-phenyl]-[C$^2$H]methanol, colourless amorphous solid in 77% yield; tlc: (2) 0.33. NMR (CDCl$_3$): 20.46, 20.55, 36.77, 41.62, 44.09, 48.77, multiplett centred at 64.96, 70.05, 111.76, 125.72, 127.34, 128.03, 128.32, 128.38, 133.15, 133.99, 137.17, 144.80, 155.52.

(±)-2-(3-Diisopropylamino-1-phenylpropyl)-4-hydroxymethyl-phenol

Intermediate B (n=1)

A solution of Intermediate A (9.1 g) in methanol (100 ml) was hydrogenated over Raneynickel (4.5 g) under ambient conditions. After 5 hrs thin layer chromatography indicated complete hydrogenolysis. The catalyst was filtered off and the solution evaporated to dryness to leave an oil (6.95 g, 96.5% yield) which gradually solidified, (±)-2-(3-diisopropylamino-1-phenylpropyl)-4-hydroxymethylphenol, m.p. 50° C., tlc: (2) 0.15. NMR (CDCl$_3$): 19.42, 19.83, 33.22, 39.62, 42.27, 48.27, 65.19, 118.32, 126.23, 126.55, 127.47, 128.33, 132.50, 144.47, 155.38.

Hydrochloride: colourless crystals, m.p. 187-190° C. (with decomposition)

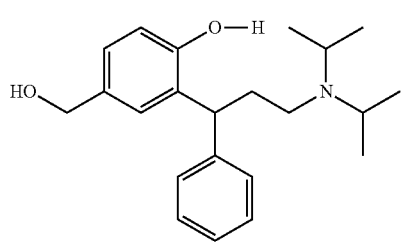

Intermediate B

S-(−)-2-(3-Diisopropylamino-1-phenylpropyl)-4-hydroxymethyl-phenol

Hydrogenolysis of S-(−)-[4-benzyloxy-3-(3-diisopropylamino-1-phenylpropyl)-phenyl]-methanol (prepared from S-(+)-3-(2-benzyloxy-5-bromophenyl)-3-phenylpropionic acid as described for the racemic series) gave the title compound in 85% yield, colourless solid; m.p.≧50° C., $[\alpha]_D^{22}$=−19.8 (c=1.0, ethanol); NMR (CDCl$_3$): 19.58, 19.96, 33.30, 39.52, 42.10, 48.00, 65.40, 118.58, 126.31, 126.57, 127.16, 127.54, 128.57, 132.63, 132.83, 144.55, 155.52.

S-(+)hydrochloride: colourless, non-hygroscopic solid, m.p. 186.4° C. (dec.); $[\alpha]_D^{22}$=+6.6 (c=0.5, water). NMR (DMSO-d$_6$): 16.58, 18.17, 31.62, 41.37, 45.90, 54.02, 63.07, 115.18, 126.05, 126.37, 128.03, 128.45, 129.04, 133.12, 143.88, 153.77.

R-(+)-2-(3-Diisopropylamino-1-phenylpropyl)-4-hydroxymethyl-phenol

Hydrogenolysis of R-(+)-[4-benzyloxy-3-(3-diisopropylamino-1-phenylpropyl)-phenyl]-methanol (prepared from R-(−)-3-(2-benzyloxy-5-bromophenyl)-3-phenylpropionic acid as described for the racemic series) gave the title compound in 87% yield, colourless solid; m.p.≧50° C., $[\alpha]_D^{22}$=+21.3 (c=1.0, ethanol).

R-(−)hydrochloride: colourless, non-hygroscopic solid, m.p. 179.8° C. (dec.); $[\alpha]_D^{22}$=−7.2 (c=0.5, water); NMR (DMSO-d$_6$) 16.59, 18.19, 31.64, 41.38, 45.92, 54.07, 63.08, 115.19, 126.07, 126.39, 128.04, 128.46, 129.05, 133.13, 143.89, 153.79.

S-(+)-mandelate: m.p. 139.7° C., $[\alpha]_D^{21}$=+38.3 (c=1.0, ethanol)

(±)-2-(3-Diisopropylamino-1-phenylpropyl)-4-hydroxy-[$^2$H$_2$]methyl-phenol Intermediate d$_2$–B (n=2)

A stirred suspension of lithium aluminium deuteride (0.1 g, 2.38 mmol) in 5 ml of dry diethyl ether was treated during 30 min at room temperature under an atmosphere of dry nitrogen with a solution of (±)-4-benzyloxy-3-(3-diisopropylamino-1-phenylpropyl)-benzoic acid methyl ester (1.0 g, 2.17 mmol) in dry diethyl ether (5 ml). After an additional stirring at room temperature for 18 hrs the reaction was quenched by the dropwise addition of 0.17 ml of $^2$H$_2$O. The resultant precipitation was filtered off, washed with small portions of ether, and the combined organic phases were evaporated to dryness in vacuum to leave

(±)-[4-benzyloxy-3-(3-diisopropylamino-1-phenylpropyl)-phenyl]-[$^2$H$_2$]methanol as slightly yellow, viscous oil which gradually crystallized, m.p. 84.1° C.; tlc: (2) 0.33 (starting material 0.46), 0.725 g, 77.2% yield. NMR (CDCl$_3$): 20.46, 20.55, 36.77, 41.62, 44.09, 48.77, multiplett centred at 64.30, 70.05, 111.76, 125.72, 125.94, 126.92, 127.34, 127.71, 128.03, 128.32, 128.38, 133.15, 133.99, 137.17, 144.80, 155.52.

A solution of the above (±)-[4-benzyloxy-3-(3-diisopropylamino-1-phenylpropyl)-phenyl]-[$^2$H$_2$]methanol (0.129 g, 0.29 mmol) in a suspension of methanol (5 ml) and wet Raney-Nickel (0.1-0.2 g) was stirred at room temperature under an atmosphere of deuterium gas ($^2$H$_2$). After 1 hr tlc indicated complete disappearance of the starting material. The mixture was filtered, evaporated and the residue was redissolved in diethyl ether (5 ml). The solution was washed with water (2×5 ml), dried over sodium sulphate, filtered and evaporated to dryness to leave a pale yellow oil, 76.3 mg, in 74.6% yield, which gradually solidified to give a colourless solid of a m.p. range of 46-49° C. Tlc: (4) 0.57 (starting material 0.77). NMR (CDCl$_3$): 19.57, 19.94, 33.33, 39.56, 42.18, 48.07, 48.43, multiplett centred at 64.61, 118.47, 126.29, 126.58, 127.55, 127.94, 128.38, 132.53, 144.53, 155.37. GC-MS (P-CI, ammonia, TMS derivative): 488.43 (100%), 489.56 (70%), 490.56 (31%), 491.57 (8%).

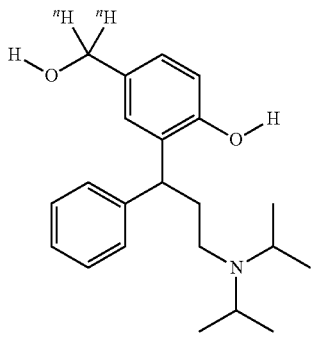

Intermediate d$_2$-B n=2, deuterium (±)-2-(3-Diisopropylamino-1-phenylpropyl)-4-hydroxy-[$^2$H$_2$]methylphenol Intermediate d$_2$-B
(iii) Heck-Cuprate-Route to Intermediate B

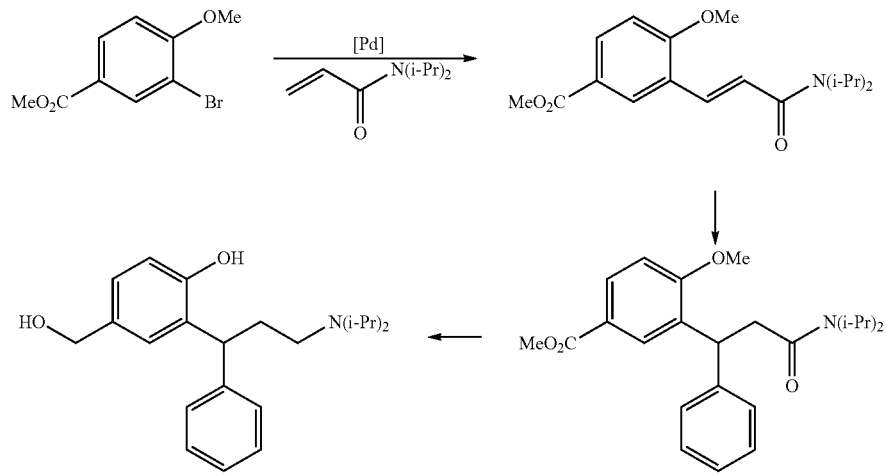

Intermediate B

N,N-Diisopropyl-acrylamide

A solution of acroyl chloride (42.2 g, 40.6 ml, 0.467 mol) in 125 ml of dichloromethane was slowly added to a cooled (0-5° C.) solution of N,N-diisopropylamine in dichloromethane (500 ml). After 2 hrs the precipitated ammonium salt was filtered off and the filtrate was washed with 1M hydrochloric acid (3×100 ml), dried (sodium sulphate), and evaporated to dryness. N,N-diisopropyl-acrylamide was obtained as a slight yellow liquid in 48% yield and ca. 99% purity. NMR (CDCl$_3$): 20.54, 21.25, 45.66, 48.10, 125.62, 130.70, 166.17.

(E)-N,N-Diisopropyl-3-(2-methoxy-5-methoxycarbonylphenyl)-acrylamide

((E)-3-(2-Diisopropylcarbamoyl-vinyl)-4-methoxy-benzoic acid methyl ester)

The reaction was carried out under an atmosphere of dry and oxygen-free nitrogen gas. All solvents and reagents were dried before use.

A stirred suspension consisting of N,N-dimethylglycine (6.0 mmol), anhydrous sodium acetate (40 mmol), methyl 3-bromo-4-methoxybenzoate (20 mmol, 4.90 g), N,N-diisopropylacrylamide (24 mmol, 3.72 g), bis-(benzonitrile)-palladium-II chloride (1.5 mol %), and 20 ml of N-methyl-2-pyrrolidinone was heated at 130° C. until no starting material could be detected by tlc (starting material methyl 3-bromo-4-methoxybenzoate: R$_f$ 0.73; N,N-diisopropylacrylamide: R$_f$ 0.46; solvent system (1)). After cooling to room temperature 50 ml of an aqueous 2N HCl solution was added. The reaction was diluted with dichloro-methane (50 ml) and the precipitated grey palladium metal was filtered off. The organic phase was washed with five portions (50 ml each) of 2N aqueous hydrochloric acid, dried (MgSO$_4$) and evaporated to dryness. The remaining off-white solid was recrystallized from ethyl acetate/n-hexane to give 4.40 g (E)-N,N-diisopropyl-3-(2-methoxy-5-methoxycarbonylphenyl)-acrylamide in 69% yield, m.p. 139-140° C., tlc: (1) R$_f$ 0.40. NMR (CD$_2$Cl$_2$): 21.22, 22.10, 46.39, 48.87, 52.59, 56.61, 111.42, 123.39, 123.78, 125.54, 130.32, 132.53, 135.07. MS (EI, DI, 105° C.): 319 (M$^{+\cdot}$, 22), 304 (6%), 276 (8%), 219 (100%), 187 (18%), 160 (7%).

(±)-N,N-Diisopropyl-3-(2-methoxy-5-methoxycarbonylphenyl)-3-phenylpropionamide

((±)-3-(2-Diisopropylcarbamoyl-1-phenylethyl)-4-methoxy-benzoic acid methyl ester)

The reaction was carried out under an atmosphere of dry and oxygen-free nitrogen gas. All solvents and reagents were dried before use.

A dark green solution of lithium diphenylcuprate was prepared by addition of phenyllithium solution (12 ml, 24 mmol, cyclohexane/diethyl ether) to a cooled (0° C.) and stirred suspension of copper-I bromide dimethylsulphide adduct (2.71 g, 13 mmol) in diethyl ether (40 ml). This solution was cooled to −78° C. and then subsequently solutions were added of trimethylchlorosilane (1.5 ml, 12 mmol) in diethyl ether (5 ml) followed by the above cinnamide (3.19 g, 10.0 mmol, (E)-N,N-diisopropyl-3-(2-methoxy-5-methoxycarbonylphenyl)-acrylamide) in 10 ml of tetrahydrofuran. The reaction was stirred for one hour at −78° C., warmed to room temperature and then quenched by the addition of 150 ml of a saturated aqueous solution of ammonium chloride. After 90 min the organic phase was washed with two portions (100 ml) of half saturated aqueous sodium chloride, dried (MgSO$_4$) and evaporated to dryness. The yellow oily residue was dissolved in a minimum of ethyl acetate and purified by column chromatography on silica gel (mobile phase (1)). Evaporation of the combined fractions of the title compound gave

(±)-N,N-diisopropyl-3-(2-methoxy-5-methoxycarbonylphenyl)-3-phenylpropionamide as a viscous slightly yellow syrup (1.8 g, 44% yield). NMR (CD$_2$Cl$_2$): 19.45, 19.56, 19.74, 38.86, 44.87, 47.92, 50.80, 54.76, 109.41, 121.32, 125.53, 128.10, 128.43, 128.78, 132.03, 143.20, 159.95, 165.95, 168.87. MS (EI, DI, 105° C.)

397 (M+·, 41%), 366 (5%), 322 (2%), 269 (3%), 255 (14%), 237 (7%), 165 (5%), 128 (12%), 91 (43%), 58 (100%).

(±)-2-(3-Diisopropylamino-1-phenylpropyl)-4-hydroxymethylphenol

A solution of (±)-N,N-diisopropyl-3-(2-methoxy-5-methoxy-carbonylphenyl)-3-phenylpropionamide (0.79 g, 2.0 mmol) in 20 ml of tetrahydrofuran was cooled to 5° C. and then treated with 2.5 ml of 1M LiAlH$_4$/THF. After stirring at room temperature for 18 hrs. finely powdered aluminium chloride (0.3 g) was added and stirring was continued for additional 4 hrs. The reaction was quenched at 5° C. by the dropwise addition of water followed by aqueous sodium hydroxide solution. The mixture was diluted with diethyl ether (150 ml) and the organic phase was washed with half saturated brine, dried (sodium sulphate), and evaporated to dryness to give the title compound as a solid off-white foam. Tlc (2) 0.16, m.p. 48-51° C. A portion of the material was converted into the hydrochloride (ethereal hydrochloric acid), m.p. 186-189° C. (dec.).

Hydrogenolytic Deoxygenation of S-(−)-2-(3-Diisopropylamino-1-phenylpropyl)-4-hydroxymethylphenol A mixture of S-(−)-2-(3-Diisopropylamino-1-phenylpropyl)-4-hydroxymethylphenol (683 mg, 2.0 mmol, [α]$_D^{22}$=−19.8 (c=1.0, ethanol)), platinum-on-carbon catalyst (120 mg) and acetic acid (1.0 ml) was diluted with ethyl acetate (50 ml) and then hydrogenated at room temperature under a pressure of 4 bar hydrogen gas for 5 hrs. The catalyst was filtered off and the filtrate was evaporated to leave an oil. The residue was redissolved in dichloromethane (25 ml) and the solution was washed with aqueous sodium hydrogencarbonate solution. The organic phase was concentrated to dryness and the oily residue taken up in ethanol (7 ml). Addition of D-(−)-tartaric acid (300 mg) and storage of the clear solution at −25° C. gave colourless crystals (310 mg) of S-(−)-2-(3-diisopropylamino-1-phenylpropyl)-4-methylphenol D-(−)hydrogentartrate in 33% yield, tlc: (4): 0.66 (starting material 0.31), [α]$_D^{22}$=−26.7 (c=1.0, methanol). NMR (CD$_3$OD): 17.98, 18.37, 20.69, 33.68, 43.12, 56.33, 74.17, 116.31, 127.51, 129.11, 129.50, 129.70, 129.89, 130.41, 144.57, 153.67, 176.88. A portion of the tartrate was treated with aqueous sodium hydrogencarbonate solution and the free base was isolated in quantitative yield as a colourless oil by extraction with ethyl acetate and evaporation of the extract. [α]$_D^{22}$=−26.3 (c=1.0, methanol).

Preferred intermediates in the processes for the preparation of the 3,3-diphenylpropylamines according to the present invention are:
(±)-3-(2-Benzyloxy-5-bromophenyl)-3-phenylpropanoic acid and its salts,
R-(−)-(2-Benzyloxy-5-bromophenyl)-3-phenylpropanoic acid and its salts,
S-(+)-(2-Benzyloxy-5-bromophenyl)-3-phenylpropanoic acid and its salts,
(±)-2-(3-Diisopropylamino-1-phenylpropyl)-4-hydroxy-[C$^2$H$_2$]methyl-phenol,
S-(−)-2-(3-diisopropylamino-1-phenylpropyl)-4-hydroxy-[C$^2$H$_2$]methyl-phenol,
R-(+)-2-(3-diisopropylamino-1-phenylpropyl)-4-hydroxy-[C$^2$H$_2$]methyl-phenol and their salts.

3. Examples a) Phenolic Monoesters aa) General Procedure
Esters of Carboxylic Acids
A stirred solution of (±)-2-(3-diisopropylamino-1-phenylpropyl)-4-hydroxymethylphenol (Intermediate B, 1.71 g, 5.01 mmol) and acid chloride (5.00 mmol carboxylic acid monochloride for compounds of formula II, 2.50 mmol for compounds of formula II') in 60 ml of dichloromethane was cooled to 0° C. and then triethylamine (0.502 g, 4.96 mmol for compounds of formula II, 1.05 g, 9.92 mmol for compounds of formula II'), dissolved in 10 ml of dichloromethane, was added dropwise during 5-10 min. Stirring was continued for 18 hrs at room temperature, and then the mixture was washed successively with water (25 ml), aqueous sodium hydrogen carbonate (5%, 25 ml), and water (25 ml). The organic phase was then dried (sodium sulphate) and evaporated under reduced pressure and at low temperature. The oily residues thus formed were finally exposed to high vacuum (2-4 hrs.) to remove traces of residual solvents.

The esters of formula II or II' were obtained as colourless to light yellow solids or viscous syrups in purities between 90% and 99% (tlc, HPLC, NMR).

Esters of N-Acylamino Acids
Phenolic Monoesters
To a solution of the respective amino acid (2.0 mmol) in 0.7 ml to 5 ml of N,N-dimethylformamide and 0.5 ml of triethylamine was added at 5° C. in one portion methyl chloroformate (2.0 mmol, 288 mg). After stirring for 2 hrs. at the same temperature the cooling bath was removed and a solution of Intermediate B (2.0 mmol, 682 mg) in 5 ml of dichloromethane and triethylamine (0.5 ml) was added. The reaction was allowed to stir for 2-8 hrs and then diluted with diethyl ether (70 ml). Solid precipitates were filtered off and the mixture was washed with aqueous sodium hydrogen sulphate solution (5%) and water. After drying (sodium sulphate), filtration and evaporation in vacuum the residue was purified by flash chromatography on silica gel (eluent: solvent system (4)). N-acylamino acid esters were obtained as viscous oils or waxy solids in yields between 24% and 73%.

bb) Salt Formation (Example Hydrochloride)
A cooled (0° C.) solution of 4.94 mmol amino base in 30 ml of dry diethyl ether was treated under an atmosphere of nitrogen with 4.70 mmol (monoamines of formula II) or 9.4 mmol (diamines of formula II') ethereal (1 M) hydrochloric acid. The oily precipitation was washed repeatedly with dry ether and then evaporated in high vacuum. The residual product solidificated in most cases as an amorphous foam. The highly hygroscopic solids show a wide melting range above 100° C. (with decomposition).

The following compounds were prepared according to the method described above and their analytical data are listed below:
(±)-Acetic acid 2-(3-diisopropylamino-1-phenylpropyl)-4-hydroxymethylphenyl ester, tlc: R$_f$ 0.47 (4), NMR (CDCl$_3$): 20.36, 20.68, 20.97, 36.59, 42.35, 43.83, 48.76, 64.58, 122.69, 125.61, 126.22, 126.71, 127.96, 128.34, 136.82, 138.97, 143.73, 147.77, 169.24; GC-MS/P-CI (ammonia, trimethylsilyl derivative): 456.8 (100%), 398.4 (4%)
(±)-Propionic acid 2-(3-diisopropylamino-1-phenylpropyl)-4-hydroxymethylphenyl ester, tlc: R$_f$ 0.52 (4); NMR (CDCl$_3$): 20.44, 20.64, 27.67, 36.67, 42.21, 43.87, 48.78, 64.70, 122.71, 125.62, 126.52, 126.78, 127.97, 128.53, 136.86, 138.82, 143.82, 147.86, 172.68; GC-MS/P-CI (ammonia, trimethylsilyl derivative): 470.38 (100%), 398.4 (4%)

(±)-n-Butyric acid 2-(3-diisopropylamino-1-phenylpropyl)-4-hydroxymethylphenyl ester, tlc: $R_f$ 0.43 (4); NMR (CDCl$_3$): 13.77, 18.40, 20.43, 20.51, 20.59, 36.15, 36.82, 42.16, 43.90, 48.83, 49.20, 64.58, 122.66, 125.98, 126.17, 126.74, 127.33, 127.94, 128.33, 136.79, 138.91, 143.82, 171.88; GC-MS/N-CI (methane, trimethylsilyl derivative): 482.3 (20%), 412.3 (100%), 340.1 (33%), 298.1 (89%), 234.7 (15%); GC-MS/P-CI (methane, trimethylsilyl derivative): 484.5 (100%), 468.4 (62%), 394.3 (22%); GC-MS/P-CI (ammonia, trimethylsilyl derivative): 484.4 (100%), 398.4 (3%)

(±)-Isobutyric acid 2-(3-diisopropylamino-1-phenylpropyl)-4-hydroxymethylphenyl ester, tlc: $R_f$ 0.43 (4); NMR (CDCl$_3$): 18.99, 19.11, 20.54, 34.21, 36.88, 41.84, 43.91, 48.78, 64.61, 122.54, 125.57, 126.14, 126.81, 127.94, 128.34, 136.84, 138.84, 143.89, 147.85, 175.36

R-(±)-Isobutyric acid 2-(3-diisopropylamino-1-phenylpropyl)-4-hydroxymethylphenyl ester Tlc: $R_f$ 0.38 (4), starting material: 0.26; colourless oil (yield 95%); NMR (CDCl$_3$): 19.02, 19.14, 19.96, 20.61, 34.26, 36.92, 41.87, 43.90, 48.80, 64.84, 122.63, 122.63, 125.64, 126.19, 126.92, 127.98, 128.39, 136.96, 138.76, 143.93, 147.97, 175.39.

Hydrochloride: colourless hygroscopic solid; $[\alpha]_D^{20}$=+5.5 (c=1.0, chloroform); NMR (CDCl$_3$): 17.03, 17.53, 18.30, 18.52, 18.95, 19.12, 31.23, 34.10, 41.69, 45.40, 54.22, 54.47, 64.00, 122.32, 126.62, 126.81, 127.40, 128.06, 128.70, 133.88, 140.64, 142.25, 147.81, 175.89.

(±)-2,2-Dimethylpropionic acid 2-(3-diisopropylamino-1-phenylpropyl)-4-hydroxymethylphenyl ester, tlc: $R_f$ 0.49 (1); NMR (CDCl$_3$): 20.46, 20.66, 26.53, 27.34, 37.12, 39.21, 41.46, 43.98, 48.81, 64.65, 122.42, 125.58, 126.16, 126.92, 128.37, 134.27, 136.92, 138.82, 143.97, 148.02, 176.97; GC-MS/P-CI (ammonia, trimethylsilyl derivative): 498.8 (100%), 482.5 (10%), 398.4 (4%)

(±)-2-Acetamidoacetic acid 2-(3-diisopropylamino-1-phenyl-propyl)-4-hydroxymethylphenyl ester

((±)-2-[Diisopropylamino)-1-phenylpropyl]-4-(hydroxymethyl)phenyl 2-(acetylamino)acetate)

NMR (CD$_3$OD): 20.33, 20.61, 22.17, 30.54, 42.39, 48.62, 51.04, 64.88, 117.99, 124.73, 125.51, 127.01, 127.75, 129.31, 131.63, 137.33, 146.67, 147.43, 171.47, 173.82

(±)-Cyclopentanecarboxylic acid 2-(3-diisopropylamino-1-phenylpropyl)-4-hydroxymethylphenyl ester Tlc: $R_f$ 0.66 (4), starting material Intermediate B (0.50), colourless oil, yield: 82%. NMR (CDCl$_3$): 20.42, 25.87, 30.25, 36.57, 41.89, 43.97, 47.15, 49.02, 64.63, 122.56, 125.60, 126.16, 126.81, 127.60, 127.94, 128.35, 128.77, 136.74, 138.88, 143.85, 147.92, 175.05.

(±)-Cyclohexanecarboxylic acid 2-(3-diisopropylamino-1-phenylpropyl)-4-hydroxymethylphenyl ester Tlc: $R_f$ 0.67 (4), starting material Intermediate B (0.50), colourless oil, yield: 93%. NMR (CDCl$_3$): 20.27, 25.40, 25.74, 29.03, 29.16, 36.29, 41.82, 43.31, 44.08, 49.36, 64.62, 122.56, 125.68, 126.22, 126.92, 127.92, 128.38, 136.65, 139.00, 143.72, 147.86, 174.40.

(±)-Benzoic acid 2-(3-diisopropylamino-1-phenylpropyl)-4-hydroxymethylphenyl ester Tlc: $R_f$ 0.31 (4); colourless syrup (99% yield, purity>95%); gradually crystallized upon refrigeration; NMR (CDCl$_3$): 20.41, 20.51, 36.65, 42.42, 43.85, 48.79, 64.70, 122.79, 125.74, 126.17, 126.83, 128.13, 128.28, 128.58, 129.48, 130.25, 133.62, 137.21, 139.10, 143.67, 148.00, 154.99.

R-(+)-Benzoic acid 2-(3-diisopropylamino-1-phenylpropyl)-4-hydroxymethylphenyl ester tlc $R_f$ 0.30 (4); colourless syrup
Hydrochloride: colourless amorphous solid; $[\alpha]_D^{20}$=+14.9 (c=1.0, chloroform);
NMR (CDCl$_3$): 17.06, 17.53, 18.25, 18.61, 31.23, 42.19, 45.49, 54.26, 54.53, 64.09, 122.55, 126.77, 127.13, 127.58, 128.10, 128.50, 128.72, 128.78, 129.02, 130.17, 133.96, 134.27, 140.81, 142.13, 147.91, 165.40.

(±)-4-Methylbenzoic acid 2-(3-diisopropylamino-1-phenylpropyl)-4-hydroxymethylphenyl ester Tlc: $R_f$ 0.30 (4), starting material Intermediate B: 0.24; yield: quantitative, viscous light yellow oil; NMR (CDCl$_3$): 20.32, 20.50, 21.78, 36.13, 42.35, 43.98, 49.29, 64.66, 122.79, 125.81, 126.19, 126.70, 127.04, 128.30, 129.32, 129.76, 130.29, 136.94, 139.20, 143.61, 144.46, 148.04, 165.07.

LC-MS: 459 (M$^{+\cdot}$, 3.5%), 444 (17%), 223 (2.5%), 195 (2%), 119 (48%), 114 (100%).

(±)-2-Methylbenzoic acid 2-(3-diisopropylamino-1-phenylpropyl)-4-hydroxymethylphenyd ester viscous colourless oil, tlc: (4) 0.64 (starting material $R_f$ 0.51), yield 84%. NMR (CDCl$_3$): 20.44, 20.53, 21.86, 22.01, 36.74, 42.36, 43.87, 48.81, 64.76, 122.93, 123.11, 125.71, 126.12, 126.88, 128.10, 128.48, 130.76, 131.26, 131.70, 132.03, 132.79, 137.28, 139.00, 141.73, 143.72, 148.04, 165.25. LC-MS: 459 (M$^{+\cdot}$, 21%), 444 (100%), 326 (1%), 223 (10%), 213 (6%), 195 (9%), 165 (14%), 115 (94%), 91 (99%).

(±)-2-Acetoxybenzoic acid 2-(3-diisopropylamino-1-phenylpropyl)-4-hydroxymethylphenyl ester colourless syrup, tlc: (4) 0.47 (starting material $R_f$ 0.51), yield 82%. NMR (CDCl$_3$): 20.39, 20.57, 20.96, 36.92, 42.29, 43.88, 48.87, 64.64, 122.39, 122.64, 124.05, 125.80, 126.11, 126.75, 128.09, 128.32, 132.23, 134.66, 137.27, 139.32, 143.64, 147.63, 151.37, 162.72, 169.73. LC-MS: 503 (M$^{+\cdot}$, 7%), 488 (59%), 446 (6%), 326 (22%), 223 (9%), 213 (9%), 195 (9%), 163 (14%), 121 (100%), 114 (88%).

(±)-1-Naphthoic acid 2-(3-diisopropylamino-1-phenylpicpyl)-4-hydroxymethylphenyl ester colourless viscous oil, tlc: (4) 0.57 (starting material $R_f$ 0.51), yield 82%. NMR (CDCl$_3$): 20.46, 20.58, 36.82, 42.46, 43.89, 48.76, 64.81, 122.98, 124.51, 125.64, 125.79, 125.98, 126.15, 126.44, 126.94, 128.12, 128.36, 128.65, 131.37, 131.82, 133.98, 134.45, 137.44, 139.08, 143.73, 148.13, 165.49. LC-MS: 495 (M⁺·, 8%), 480 (100%), 213 (7%), 165 (8%), 155 (95%), 127 (100%), 114 (90%).

(±)-2-Naphthoic acid 2-(3-diisopropylamino-1-phenylpropyl)-4-hydroxymethylphenyl ester colourless slightly yellow viscous oil, tlc: (4) 0.57 (starting material $R_f$ 0.51), yield 71%. NMR (CDCl$_3$): 20.47, 20.59, 36.71, 42.59, 43.85, 48.81, 64.82, 122.89, 126.89, 127.89, 128.19, 128.41, 128.68, 129.50, 132.03, 132.55, 135.87, 137.22, 139.08, 143.83, 148.20, 165.14. LC-MS: 495 (M⁺·, 7%), 480 (98%), 223 (8%), 213 (6%), 195 (6%), 165 (8%), 155 (96%), 127 (100%), 114 (81%).

(±)-4-Chlorobenzoic acid 2-(3-diisopropylamino-1-phenylpropyl)-4-hydroxymethylphenyl ester Tlc: $R_f$ 0.54 (4), starting material Intermediate B: 0.44; yield: quantitative, viscous light yellow oil; NMR (CDCl$_3$): 20.34, 20.50, 36.41, 42.51, 43.84, 48.93, 64.66, 122.72, 125.82, 126.88, 127.27, 128.06, 128.56, 128.96, 131.60, 133.80, 136.95, 139.30, 140.16, 143.60, 147.87, 164.10. LC-MS: 479 (M⁺·, 1.5%), 464 (10%), 223 (2%), 195 (2%), 165 (1.5%), 139 (25%), 114 (100%).

(±)-4-Methoxybenzoic acid 2-(3-diisopropylamino-1-phenylpropyl)-4-hydroxymethylphenyl ester Tlc: $R_f$ 0.47 (4), starting material Intermediate B: 0.42; yield: 89%, viscous light yellow oil; NMR (CDCl$_3$): 20.31, 20.47, 36.43, 42.39, 43.90, 48.97, 55.53, 64.71, 121.79, 122.86, 125.72, 126.14, 126.79, 128.11, 128.27, 131.27, 131.77, 132.36, 132.84, 137.15, 139.01, 143.74, 148.08, 163.92, 164.71. LC-MS: 475 (M⁺·, 3.5%), 460 (20%), 223 (2%), 195 (2%), 135 (48%), 114 (100%).

(±)-2-Methoxybenzoic acid 2-(3-diisopropylamino-1-phenylpropyl)-4-hydroxymethydphenyl ester Tlc: $R_f$ 0.40 (4), starting material Intermediate B: 0.42; yield: 98%, viscous light yellow oil; NMR (CDCl$_3$): 20.29, 20.42, 36.50, 41.92, 44.02, 49.09, 55.95, 64.72, 119.10, 120.20, 122.86, 125.64, 126.10, 126.82, 128.06, 128.30, 132.38, 134.32, 137.11, 139.01, 143.87, 148.00, 159.82, 164.40. LC-MS: 475 (M⁺·, 3.5%), 460 (18%), 223 (1%), 195 (1%), 135 (49%), 114 (100%).

(±)-4-Nitrobenzoic acid 2-(3-diisopropylamino-1-phenylpropyl)-4-hydroxymethylphenyl ester Tlc: $R_f$ 0.44 (4), starting material Intermediate B: 0.42; yield: 78%, viscous yellow oil which slowly solidified; m.p. 123.6° C.; NMR (CDCl$_3$): 20.47, 20.62, 36.52, 42.66, 43.70, 48.75, 64.69, 122.61, 123.72, 125.91, 126.33, 127.04, 128.02, 128.37, 131.32, 134.86, 136.83, 139.55, 143.56, 147.75, 150.93, 163.04. LC-MS: 490 (M⁺·, 1.5%), 475 (15%), 327 (0.8%), 223 (3%), 195 (3%), 150 (15%), 114 (100%).

(±)-2-Ditrabenzoic acid 2-(3-diisopropylamino-1-phenylpropyl)-4-hydroxymethylphenyl ester Tlc: $R_f$ 0.32 (4), starting material Intermediate B: 0.42; yield: 92%, viscous yellow oil which slowly solidified; NMR (CDCl$_3$): 20.39, 20.50, 36.74, 42.14, 43.89, 48.71, 48.92, 64.59, 122.15, 123.95, 124.18, 125.89, 126.25, 127.23, 127.99, 128.39, 129.95, 132.95, 133.08, 136.72, 139.62, 143.64, 147.63, 148.15, 163.90. LC-MS: 490 (M⁺·, 1%), 475 (11%), 327 (2.5%), 223 (2.5%), 195 (3%), 165 (3%), 150 (7%), 114 (100%).

(±)-N-Acetylglycine 2-(3-diisopropylamino-1-phenylpropyl)-4-hydroxymethylphenyl ester/(±)-2-Acetamidoacetic acid 2-(3-diisopropylamino-1-phenylpropyl)-4-hydroxymethylphenyl ester

((±)-2-[Diisopropylamino-1-phenylpropyl]-4-(hydroxymethyl)-phenyl 2-(acetylamino)acetate)

NMR (CD$_3$OD): 20.33, 20.61, 22.17, 30.54, 42.39, 48.62, 51.04, 64.88, 117.99, 124.73, 125.51, 127.01, 127.75, 129.31, 131.63, 137.33, 146.67, 147.43, 171.47, 173.82.

(±)-Malonic acid bis-[2-(3-diisopropylamino-1-phenylpropyl)-4-hydroxymethylphenyl]ester, tlc: $R_f$ 0.38 (4); NMR (CDCl$_3$): 20.52, 20.62, 20.69, 36.95, 41.84, 42.82, 43.89, 48.23, 64.83, 123.37, 127.36, 127.97, 128.42, 128.38, 129.06, 131.55, 137.50, 138.90, 148.23, 148.32, 160.54

(±)-Succinic acid bis-(2-(3-diisopropylamino-1-phenylpropyl)-4-hydroxymethylphenyl]ester, tlc: $R_f$ 0.40 (4); NMR (CDCl$_3$): 20.54, 20.63, 20.73, 30.69, 36.91, 41.80, 43.92, 48.20, 64.81, 122.60, 127.41, 127.93, 128.39, 129.31, 131.80, 136.73, 138.92, 143.82, 148.17, 168.01

(±)-Pentanedioic acid bis-[2-(3-diisopropylamino-1-phenylpropyl)-4-hydroxymethylphenyl]ester, tlc: $R_f$ 0.43; NMR (CDCl$_3$): 20.47, 20.60, 32.87, 36.93, 41.82, 43.90, 48.22, 64.81, 64.83, 122.85, 127.39, 127.99, 128.35, 129.31, 131.84, 136.98, 138.94, 143.80, 147.40, 169.05

(±)-Hexanedioic acid bis-[2-(3-diisopropyl amino-1-phenylpropyl)-4-hydroxymethylphenyl]ester, tlc: $R_f$ 0.43; NMR (CDCl$_3$): 20.64, 23.40, 34.37, 36.95, 41.84, 43.88, 48.25, 64.87, 122.88, 127.34, 127.97, 128.39, 129.33, 131.80, 136.99, 138.94, 143.82, 147.65, 168.72 b) Identical Diesters (±)-Identical diesters (formula III) were prepared and worked up as described above with the exception that 2.4 mmol of both triethylamine and acyl chloride (R¹—COCl) were used. The physical properties were similar to the bases and salts described above.

Diesters of N-acylaminoacids were prepared as described for phenolic monoesters with the exception that an additional molar equivalent of acylating agent (mixed acid anhydride) was used.

In particular, the following compounds were prepared and their analytical data are given below:

(±)-Formic acid 2-(3-diisopropylamino-1-phenylpropyl)-4-formyloxymethylphenyl ester, tlc: $R_f$ 0.65 (4). This diester was prepared from mixed formic acetic anhydride and Intermediate B as described for other substrates previously (F. Reber, A. Lardon, T. Reichstein, *Helv. Chim. Acta* 37: 45-58 [1954])

(±)-Acetic acid 4-acetoxy-3-(3-diisopropylamino-1-phenyl-propyl)-benzyl ester, tlc: $R_f$ 0.76 (4); GC-MS/P-CI (ammonia): 426.3 (100%), 368.3 (22%); GC-MS/P-CI (methane, trimethyl-silyl derivative): 426.4 (64%), 410.3 (16%), 366.3 (100%); hydrochloride, NMR (DMSOd$_6$)-16.50, 16.76, 18.05, 20.94, 21.04, 27.02, 31.39, 41.28, 45.26, 53.80, 65.21, 123.39, 126.84, 127.61, 127.85, 128.70, 134.41, 135.49, 142.68, 148.20, 169.32, 170.42

(±)-Propionic acid 2-(3-diisopropylamino-1-phenylpropyl)-4-propionyloxymethylphenyl ester, tlc: $R_f$ 0.82 (4); NMR (CDCl$_3$): 20.53, 20.73, 21.14, 27.66, 36.73, 42.10, 43.68, 48.65, 65.75, 122.65, 126.10, 127.01, 127.70, 128.34, 128.78, 133.73, 136.81, 143.76, 148.45, 172.45, 174.21; GC-MS/P-CI (ammonia): 454.8 (100%), 438.5 (9%), 382.4 (27%)

(±)-n-Butyric acid 4-n-butyryloxymethyl-2-(3-diisopropyl-amino-1-phenylpropyl)-phenyl ester, tlc: $R_f$ 0.86 (4); NMR (CDCl$_3$): 13.70, 13.76, 18.44, 20.53, 20.69, 21.13, 36.14, 36.76, 37.09, 42.08, 43.73, 48.71, 65.64, 122.81, 125.97, 126.97, 127.92, 128.35, 128.77, 133.78, 136.99, 143.76, 148.41, 171.68, 173.40; GC-MS/P-CI (ammonia): 482.8 (100%), 396.4 (67%)

(±)-Isobutyric acid 2-(3-diisopropylamino-1-phenylpropyl)-4-isobutyryloxymethylphenyl ester, tlc: $R_f$ 0.83 (4); NMR (CDCl$_3$): 18.97, 19.10, 20.64, 20.67, 34.01, 34.23, 36.98, 41.72, 43.70, 48.65, 65.61, 122.50, 126.18, 126.73, 127.92, 128.13, 128.36, 133.90, 137.01, 143.85, 148.41, 175.17, 176.81; GC-MS/N-CI (methane): 480.3 (15%); GC-MS/P-CI (methane): 482.5 (63%), 466.4 (18%), 394.3 (100%)

(±)-2,2-Dimethylpropionic acid 3-(3-diisopropylamino-1-phenylpropyl)-4-(2,2-dimethylpropionyloxy)-benzyl ester, Tlc: $R_f$ 0.96 (4); NMR (CDCl$_3$): 20.44, 20.75, 27.09, 27.24, 37.18, 38.68, 39.15, 41.25, 43.66, 48.20, 65.50, 122.36, 126.32, 127.22, 127.48, 127.83, 128.29, 133.99, 136.98, 143.87, 148.37, 176.70, 178.10; GC-MS/P-CI (methane): 510.5 (76%), 494.5 (21%), 408.4 (100%)

(±)-Benzoic acid 4-benzoyloxymethyl-2-(3-diisopropylamino-1-phenylpropyl)-phenyl ester, tlc: $R_f$ 0.80 (4); NMR (CDCl$_3$): 20.62, 36.95, 41.72, 43.89, 48.23, 66.76, 122.22, 125.33, 127.36, 127.62, 127.89, 127.89, 127.97, 128.38, 129.49, 130.52, 130.64, 131.15, 131.22, 131.98, 136.38, 137.66, 143.82, 148.95, 164.77, 166.60

(+)-Benzoic acid 4-benzoyloxymethyl-2-(3-diisopropylamino-1-phenylpropyl)-phenyl ester Hydrochloride: colourless solid; tlc: (4) 0.70, $[\alpha]_D^{20}$=+24.2 (c=1.0, chloroform). NMR (DMSO-d$_6$): 16.52, 17.99, 18.06, 26.99, 31.32, 53.94, 65.98, 123.58, 127.65, 127.98, 128.62, 128.90, 129.02, 129.45, 129.71, 130.10, 133.64, 134.32, 134.55, 135.60, 142.52, 148.37, 164.53, 165.76.

c) Mixed Diesters

Mixed diesters (formula IV) were prepared by acylation of the respective benzylic or phenolic monoesters. Working up and physical properties corresponded to the bases and salts described above.

In particular, the following compounds were prepared and their analytical data are given below:

(±)-Acetic acid 2-(3-diisopropylamino-1-phenylpropyl)-4-formyloxymethylphenyl ester, tlc: $R_f$ 0.76 (4); NMR (CDCl$_3$): 20.62, 20.91, 33.25, 42.20, 42.28, 48.23, 70.70, 122.96, 127.36, 127.97, 128.38, 128.73, 132.02, 135.41, 137.11, 143.81, 149.35, 161.34, 168.95

(±)-Benzoic acid 2-(3-diisopropylamino-1-phenylpropyl)-4-formyloxymethylphenyl ester, tlc: $R_f$ 0.74 (4); NMR (CDCl$_3$): 20.60, 36.93, 41.72, 43.89, 48.23, 70.71, 122.50, 125.33, 127.30, 127.89, 127.97, 128.36, 129.57, 130.65, 131.13, 132.05, 135.41, 136.66, 143.80, 149.15, 161.35, 164.78

(±)-Benzoic acid 2-(3-diisopropylamino-1-phenylpropyl)-4-acetoxymethylphenyl ester Viscous colourless oil, tlc: $R_f$ 0.70 (4); NMR (CDCl$_3$): identical with R-(±) enantiomer, see below.

R-(+)-Benzoic acid 2-(3-diisopropylamino-1-phenylpropyl)-4-acetoxymethylphenyl ester tlc: $R_f$ 0.70 (4)

Hydrochloride: colourless non-hygroscopic solid $[\alpha]_D^{20}$=+27.1 (c=1.0, chloroform). NMR (CDCl$_3$): 17.14, 18.53, 21.04, 31.51, 42.25, 46.27, 54.74, 65.58, 123.18, 127.07, 127.55, 127.61, 127.99, 128.80, 130.22, 134.14, 134.81, 135.27, 141.44, 148.54, 165.19, 170.81.

(±)-Isobutyric acid 4-acetoxymethyl-2-(3-diisopropylamino-1-phenylpropyl)-phenyl ester, tlc: $R_f$ 0.77 (4); NMR (CDCl$_3$): 18.99, 19.12, 20.65, 21.05, 34.24, 37.02, 41.79, 43.79, 48.72, 65.98, 122.75, 126.76, 127.14, 127.94, 128.39, 128.84, 133.55, 137.04, 143.84, 148.56, 170.84, 175.18

(+)-Isobutyric acid 4-acetoxymethyl-2-(3-diisopropylamino-1-phenylpropyl)-phenyl ester colourless oil Hydrochloride: colourless hygroscopic solid; $[\alpha]_D^{20}$=+14.6 (c=1.0, chloroform); NMR (CDCl$_3$): 16.89, 17.04, 18.31, 18.54, 18.92, 19.06, 20.95, 31.49, 34.07, 41.64, 46.17, 54.55, 65.49, 122.91, 126.93, 127.48, 127.83, 128.74, 134.50, 134.88, 141.61, 148.44, 170.67, 175.63.

(±)-2,2-Dimethylpropionic acid 4-acetoxy-3-(3-diisopropyl-amino-1-phenylpropyl)-benzyl ester, tlc: $R_f$ 0.80 (4); NMR (CDCl$_3$): 20.63, 20.93, 27.19, 33.25, 37.49, 42.21, 42.25, 48.22, 67.37, 123.18, 127.36, 127.84, 128.39, 131.16, 137.34, 143.84, 148.29, 168.93, 178.40

(±)-2,2-Dimethylpropionic acid 4-acetoxymethyl-2-(3-diisopropylamino-1-phenylpropyl)-phenyl ester, tlc: $R_f$ 0.81 (4); NMR (CDCl$_3$): 20.60, 20.79, 27.09, 36.93, 37.35, 41.85, 42.29, 48.25, 65.91, 122.36, 127.37, 127.99, 128.39, 129.38, 132.69, 136.00, 136.85, 143.80, 170.45, 176.60 d) Benzylic Monoesters

A mixture consisting of Intermediate B (80 mg, 0.23 mmol), vinyl ester (0.4 ml), tert.-butyl methylether (18 ml), and lipase enzyme (1.0 g) was gently shaken at room temperature. Benzylic formate, acetate, and n-butyrate were prepared from the corresponding vinyl ester donors using SAM I lipase (Amano Pharmaceutical Co.). Benzoylation was achieved with vinyl benzoate in the presence of Lipozym IM 20 (Novo Nordisk), whereas pivalates and isobutyrates were obtained from the corresponding vinyl esters under catalysis of Novozym SP 435 (Novo Nordisk). Tlc analysis indicated after 2-24 hrs complete disappearence of the starting material ($R_f$=0.45 (3)). The mixture was filtered and then evaporated under high vacuum (<40° C.) to give the carboxylic acid ($R^1$—CO$_2$R) salts of the respective benzylic monoesters as colourless to light yellow oils.

In particular, the following compounds were prepared and their analytical data are given below:

(±)-Formic acid 3-(3-diisopropylamino-1-phenylpropyl)-4-hydroxybenzyl ester, tlc: $R_f$ 0.25 (2); NMR (CDCl$_3$): 19.43, 33.24, 39.61, 42.25, 48.21, 68.44, 118.09, 127.34, 127.66, 128.31, 128.39, 133.97, 144.47, 156.63, 161.32

(±)-Acetic acid 3-(3-diisopropylamino-1-phenylpropyl)-4-hydroxybenzyl ester, tlc: $R_f$ 0.26 (2); NMR (CDCl$_3$): 19.45, 20.96, 33.26, 39.63, 42.27, 48.23, 63.59, 118.00, 127.36, 128.33, 128.48, 128.53, 129.13, 131.59, 133.88, 144.49, 155.74, 170.44

(±)-Propionic acid 3-(3-diisopropylamino-1-phenylpropyl)-4-hydroxybenzyl ester, tlc: $R_f$ 0.45 (2); NMR (CDCl$_3$): 19.02, 19.43, 27.58, 33.20, 39.61, 42.25, 48.21, 64.08, 118.30, 125.30, 127.03, 127.39, 128.31, 130.12, 134.22, 144.51, 155.64, 173.22

(±)-Butyric acid 3-(3-diisopropylamino-1-phenylpropyl)-4-hydroxybenzyl ester, tlc: $R_f$ 0.54 (2); NMR (CDCl$_3$): 13.58, 18.40, 19.45, 33.29, 35.88, 39.65, 42.23, 48.25, 63.96, 118.32, 124.55, 126.20, 127.35, 128.32, 129.91, 134.22, 144.50, 155.60, 169.05

(±)-Isobutyric acid 3-(3-diisopropylamino-1-phenylpropyl)-4-hydroxybenzyl ester, tlc: $R_f$ 0.56 (4); NMR (CDCl$_3$): 19.09, 19.45, 33.28, 33.59, 39.65, 42.29, 48.25, 64.63, 118.35, 125.35, 127.03, 127.38, 128.35, 128.49, 129.79, 134.22, 144.52, 155.65, 175.48

(±)-2,2-Dimethylpropionic acid 3-(3-diisopropylamino-1-phenylpropyl)-4-hydroxybenzyl ester, tlc: $R_f$ 0.61 (4); NMR (CDCl$_3$): 19.41, 27.15, 33.24, 37.46, 39.61, 42.25, 48.21, 65.10, 118.30, 125.32, 127.00, 127.34, 128.31, 129.42, 134.18, 144.47, 155.61, 178.39

(±)-Benzoic acid 3-(3-diisopropylamino-1-phenylpropyl)-4-hydroxybenzyl ester, tlc: $R_f$ 0.77 (4); NMR (CDCl$_3$): 18.01, 19.40, 33.24, 39.60, 42.40, 48.20, 66.93, 117.13, 127.18, 127.81, 128.33, 129.98, 130.17, 132.96, 133.58, 142.33, 156.95, 166.60 e) Ethers and Silyl Ethers

A mixture of Intermediate B (3.4 g, 10 mmol), methanesulphonic acid (2 ml, 31 mmol), and alcohol $R^{10}$—OH (50-150 ml) was stirred at room temperature until no starting material was detectable (2-24 hrs). After evaporation to dryness (<35° C.) the residue was redissolved in aqueous sodium hydrogen carbonate solution (100-200 ml, 5%, w/v) and the solution was extracted with ethyl acetate (75 ml). The organic phase was separated, dried (Na$_2$SO$_4$), filtered and evaporated to give bases of formula VI ($R^{11}$=H) as colourless to light yellow oils.

Mixed ester ether derivatives, e.g. of Intermediate A, were prepared by benzylic acylation of phenolic ethers, such as Intermediate A, according to the procedure described for examples of the structure of formula IV.

Hydrochlorides:

Molar equivalents of bases of formula VI ($R^{11}$=H), dissolved in tert.-butyl methylether, and ethereal hydrochloric acid were combined at room temperature. Oily precipitates were separated and dried in vacuum, crystalline hydrochlorides were isolated and recrystallized from acetonitrile or acetone to give colourless crystalline material.

In particular, the following compounds were prepared and their analytical data are given below:

(±)-2-(3-Diisopropylamino-1-phenylpropyl)-4-methoxymethyl-phenol, tlc: $R_f$ 0.61 (4); GC-MS/P-CI (methane, trimethylsilyl derivative): 428.4 (100%), 412.3 (49%), 396.3 (52%); hydrochloride: amorphous hygroscopic colourless solid; m.p. 161° C.; NMR (CD$_3$OD): 17.39/18.75 (broad signals), 33.79, 43.13, 56.47, 58.00, 75.59, 116.19, 120.79, 127.62, 129.04, 129.14, 129.42, 129.55, 130.43, 144.32, 155.85

(±)-2-(3-Diisopropylamino-1-phenylpropyl)-4-ethoxymethyl-phenol, tlc: $R_f$ 0.72 (4); GC-MS/P-CI (ammonia, trimethylsilyl derivative): 444.8 (100%), 398.4 (6%); hydrochloride: colourless non-hygroscopic crystals, m.p. 158-161° C., NMR (CD$_3$OD): 15.43, 17.12, 18.82, 33.80, 56.49, 66.49, 73.62, 116.19, 127.63, 128.99, 129.13, 129.36, 129.55, 130.58, 130.75, 144.32, 155.77

(±)-2-(3-Diisopropylamino-1-phenylpropyl)-4-propoxymethyl-phenol, NMR (CDCl$_3$): 18.62, 19.44, 23.10, 33.24, 39.61, 42.26, 48.22, 71.87, 73.94, 117.78, 124.95, 127.35, 127.57, 128.32, 128.47, 133.66, 134.23, 144.48, 155.25

(±)-2-(3-Diisopropylamino-1-phenylpropyl)-4-isopropoxymethyl-phenol, NMR (CDCl$_3$): 19.44, 22.32, 33.27, 39.65, 42.29, 48.25, 69.28, 72.10, 117.90, 127.38, 128.03, 128.41, 131.10, 133.76, 134.37, 144.51, 154.65.

Hydrochloride: colourless crystals, m.p. 140.4° C., tlc (4) 0.61. LC-MS: 383 (6%, [M-HCl]$^+$), 368 (11%), 324 (1%), 223 (6%), 195 (3%), 165 (2%), 155 (5%), 114 (100%). NMR (DMSO-d$_6$): 16.57, 18.09, 18.19, 22.29, 31.58, 41.25, 45.87, 53.97, 69.26, 69.92, 115.28, 126.34, 127.08, 127.25, 127.96, 128.45, 129.07, 129.70, 132.31, 143.88, 154.22.

(±)-2-(3-Diisopropylamino-1-phenylpropyl)-4-butoxymethylphenol, NMR (CDCl$_3$): 13.75, 19.44, 19.75, 32.24, 33.28, 39.60, 42.20, 48.20, 72.45, 117.87, 125.50, 127.29, 128.39, 133.70, 134.30, 144.47, 155.36

(±)-Acetic acid 2-(3-Diisopropylamino-1-phenylpropyl)-4-methoxymethylphenyl ester, NMR (CDCl$_3$): 19.99, 20.62, 20.90, 33.33, 42.30, 48.21, 58.41, 75.94, 122.92, 127.37, 127.95, 128.35 131.85, 136.99, 138.81, 143.88, 147.88, 168.95

(±)-Acetic acid 2-(3-Diisopropylamino-1-phenylpropyl)-4-ethoxymethylphenyl ester, NMR (CDCl$_3$): 15.49, 19.94, 20.95, 33.23, 42.25, 48.25, 65.70, 73.73, 122.63, 127.46, 127.95, 128.36, 131.65, 136.79, 139.71, 143.80, 147.66, 168.99

(±)-2-(3-Diisopropylamino-1-phenylpropyl)-4-trimethylsilanyloxymethylphenol, NMR (CDCl$_3$): 0.10, 19.40, 19.43, 33.25, 39.65, 42.25, 48.20, 64.93, 117.90, 124.90, 126.60, 127.35, 128.35, 128.48, 133.80, 137.15, 144.49, 155.28

(±)-Diisopropyl-[3-phenyl-3-(2-trimethylsilanyloxy-5-trimethylsilanyloxymethylphenyl)-propyl]amine, NMR (CDCl$_3$): 0.10, 0.29, 19.40, 19.53, 33.28, 41.19, 42.27, 48.25, 66.40, 121.37, 127.36, 128.25, 128.50, 136.42, 144.10, 154.98

(±)-[3-(3-Diisopropylamino-1-phenylpropyl)-4-trimethylsilanyloxyphenyl]methanol, NMR (CDCl$_3$): 0.29, 0.33, 19.40, 19.53, 33.27, 41.16, 42.27, 48.23, 65.22, 118.04, 124.99, 126.52, 127.30, 128.25, 134.16, 136.80, 144.14, 155.06

(±)-Diisopropyl-[3-(5-methoxymethyl-2-trimethylsilanyloxyphenyl)-3-phenylpropyl]amine, NMR (CDCl$_3$): 0.28, 0.32, 19.39, 19.43, 33.28, 41.22, 42.33, 48.19, 58.40, 75.95, 117.68, 124.92, 126.60, 127.35, 128.25, 128.55, 134.00, 136.47, 144.16, 155.09

(±)-Diisopropyl-[3-(5-ethoxymethyl-2-trimethylsilanyloxyphenyl)-3-phenylpropyl]amine, NMR (CDCl$_3$): 0.28, 0.31, 15.50, 19.42, 19.58, 33.29, 41.17, 42.25, 48.20, 65.70, 72.48, 117.50, 124.75, 126.39, 127.39, 128.25, 128.50, 134.99, 136.28, 144.19, 154.28

(±)-[4-(tert.-Butyl-dimethylsilanyloxy)-3-(3-diisopropylamino-1-phenylpropyl)-phenyl]methanol, $R_f$ 0.65 (3)

(±)-Acetic acid 4-(tert.-butyl-dimethylsilanyloxy)-3-(3-diisopropylamino-1-phenylpropyl)-benzyl ester, NMR (CDCl$_3$): −4.92, −5.00, 19.40, 19.49, 20.40, 20.83, 23.49, 33.25, 41.22, 42.25, 48.25, 72.55, 81.55, 121.24, 124.88, 127.40, 128.26, 128.44, 128.48, 133.37, 135.74, 144.11, 155.20

(±)-4-(tert.-Butyl-dimethylsilanyloxymethyl)-2-(3-diisopropylamino-1-phenylpropyl)-phenol, tlc: $R_f$ 0.70 (3); GC-MS/N-CI (methane, trimethylsilyl derivative): 526.5 (59%), 454.3 (100%), 412.2 (14%), 340.1 (42%); GC-MS/P-CI (methane, trimethylsilyl derivative): 528.6 (100%), 512.5 (85%), 470.43 (10%), 396.3 (31%)

(±)-Acetic acid 4-(tert.-butyl-dimethylsilanyloxy)-2-(3-diisopropylamino-1-pbenylpropyl)-phenyl ester, NMR (CDCl$_3$): −4.77, −4.88, 19.15, 20.65, 20.93, 24.77, 33.25, 42.20, 48.20, 67.90, 122.79, 125.15, 127.44, 127.90, 128.41, 136.99, 140.55, 143.85, 147.86, 168.95

(±)-{3-[2-(tert.-Butyl-dimethylsilanyloxy)-5-(tert.-butyl-dimethylsilanyloxymethyl)-phenyl]-3-phenylpropyl}-diisopropylamine, tlc: R$_f$ 0.94 (3); GC-MS/N-CI (methane): 568.6 (62%), 454.3 (100%), 438.2 (10%), 340.2 (58%), 324.8 (16%), 234.7 (78%); GC-MS/P-CI (methane): 570.6 (70%), 554.5 (52%), 512.5 (18%), 438.4 (24%)

(±)-Acetic acid 4-benzyloxy-3-(3-diisopropylamino-1-phenylpropyl)-benzyl ester, tlc: R$_f$ 0.56 (5); GC-MS/P-CI (ammonia): 474.4 (100%), 416.4 (54%); NMR (CDCl$_3$): 20.44, 20.56, 21.07, 36.73, 41.53, 44.01, 48.79, 66.43, 70.00, 111.61, 125.75, 127.34, 127.55, 127.76, 127.90, 128.03, 128.27, 128.39, 133.98, 136.98, 144.63, 156.05, 170.94

(±)-Benzoic acid 4-benzyloxy-3-(3-diisopropylamino-1-phenyl-propyl)-benzyl ester, tlc: R$_f$ 0.87 (4); NMR (CDCl$_3$): 20.54, 20.60, 36.80, 41.51, 43.95, 48.67, 66.83, 70.04, 111.66, 125.76, 127.35, 127.45, 127.78, 128.06, 128.27, 128.30, 128.42, 128.85, 129.66, 130.55, 132.86, 134.05, 137.03, 144.75, 156.08, 166.46; GC-MS/P-CI (ammonia): 536.5 (100%), 416.4 (42%)

(±)-Isobutyric acid 4-benzyloxy-3-(3-diisopropylamino-1-phenylpropyl)-benzyl ester, tlc: R$_f$ 0.77 (4); NMR (CDCl$_3$): 19.01, 20.62, 20.65, 34.04, 36.85, 41.54, 43.97, 48.71, 66.15, 70.06, 111.62, 125.79, 125.96, 126.97, 127.24, 127.55, 127.81, 128.08, 128.34, 128.45, 134.05, 137.10, 144.79, 156.00, 177.01; GC-MS/P-CI (ammonia): 502.4 (100%), 416.4 (49%)

f) Carbamates and Carbonates

Mono N-Substituted Carbamates

A solution of 4.0 mmol of Intermediate B, benzylic ether (formula VI, R$^{11}$=H) or monoester of formula II in dichloromethane (20 ml) was treated at room temperature for 16 hrs with isocyanate (4.8 mmol) or diisocyanate (2.2 mmol). After washing with 10 ml aqueous sodium hydrogen carbonate (5%, w/v), drying (Na$_2$SO$_4$) and evaporation oily residues or colourless solids of the free bases were obtained.

N-Disubstituted Carbamates

N,N-dialkyl-carbamoylchloride (4.4 mmol) was dissolved in dichloromethane and dropped into a cooled (0° C.) and stirred mixture consisting of Intermediate B (4.0 mmol), dichloromethane (30 ml) and triethylamine (7.0 mmol, 0.71 mg, 1 ml). Stirring was continued for 6 hrs. The mixture was then washed with 5 portions (10 ml) of aqueous sodium hydrogen carbonate, dried (sodium sulphate), filtered and evaporated to give the carbamates as colourless oils or solids.

Bis-carbamates were prepared in like manner using Intermediate B and excess isocyanate (4.8 mmol) and toluene as solvent at 65° C. over 18 hrs.

Carbonates were prepared and worked-up according to the methods described for the preparation of compounds of formulae II to IV. Alkyl chloroformates were used as acylation re-agents.

Hydrochlorides:

The oils or solids were redissolved in tetrahydrofuran (10 ml). Addition of ethereal hydrochloric acid and evaporation to dryness in high vacuum gave crystalline or amorphous carbamate hydrochlorides.

In particular, the following compounds were prepared and their analytical data are given below:

(±)-N-Ethylcarbamic acid 2-(3-diisopropylamino-1-phenylpropyl)-4-hydroxymethylphenyl ester, tlc: R$_f$ 0.38 (4); GC-MS/P-CI (ammonia, trimethylsilyl derivative): 486.8 (100%), 413.4 (5%), 398.4 (6%); hydrochloride: m.p. 64° C. (with decomposition); NMR (DMSO-d$_6$): 15.16, 16.68, 18.05, 18.13, 25.33, 31.26, 35.46, 53.94, 62.65, 67.22, 123.04, 125.70, 126.72, 127.86, 128.67, 135.42, 136.02, 140.07, 142.98, 147.53, 154.52

(±)-N,N-Dimethylcarbamic acid 2-(3-diisopropylamino-1-phenylpropyl)-4-hydroxymethylphenyl ester NMR (CDCl$_3$): 20.34, 20.66, 30.51, 36.33, 36.77, 42.00, 48.28, 50.21, 65.65, 119.83, 123.44, 125.19, 126.60, 127.38, 127.54, 129.31, 136.62, 143.33, 150.99, 155.67.

(±)-N,N-Diethylcarbamic acid 2-(3-diisopropylamino-1-phenylpropyl)-4-hydroxymethylphenyl ester NMR (CDCl$_3$): 20.54, 20.66, 30.49, 35.61, 42.42, 48.31, 50.20, 65.56, 119.43, 123.40, 125.33, 126.66, 126.99, 127.05, 136.30, 143.27, 149.13, 154.97

(±)-N-Phenylcarbamic acid 2-(3-diisopropylamino-1-phenylpropyl)-4-hydroxymethylphenyl ester; NMR (CDCl$_3$): 20.52, 20.61, 36.91, 39.44, 42.25, 48.22, 62.66, 118.36, 119.46, 123.50, 125.32, 127.11, 127.99, 130.15, 132.63, 139.65, 141.33, 145.16, 152.21, 156.00

(±)-[2-(3-Diisopropylamino-1-phenylpropyl)-4-hydroxymethyl-phenoxycarbonylamino]acetic acid ethyl ester hydrochloride Tlc: R$_f$ 0.14 (4); m.p. colourless crystals (from acetone, 21% yield); NMR (CDCl$_3$): 16.76, 16.86, 18.45, 20.96, 31.37, 42.20, 46.13, 54.56, 65.50, 123.10, 126.98, 127.66, 128.72, 130.14, 134.05, 134.72, 135.22, 141.37, 148.47, 165.12, 170.71

(±)-N-Ethylcarbamic acid 3-(3-diisopropylamino-1-phenylpropyl)-4-N-ethylcarbamoyloxybenzyl ester, tlc: R$_f$ 0.36 (3); NMR (CDCl$_3$): 15.00, 19.23, 19.40, 33.26, 36.00, 39.62, 42.35, 48.12, 65.95, 118.30, 125.45, 127.08, 128.33, 130.37, 134.24, 144.44, 155.44, 157.74

(±)-N,N-Dimethylcarbamic acid 3-(3-diisopropylamino-1-phenylpropyl)-4-N,N-dimethylcarbamoyloxybenzyl ester NMR (CDCl$_3$): 20.59, 20.66, 30.59, 35.96, 36.40, 36.74, 35.98, 42.03, 48.26, 50.09, 67.09, 119.04, 123.23, 123.49, 125.01, 126.67, 127.72, 129.33, 133.65, 143.43, 150.99, 155.63.

(±)-N,N-Diethylcarbamic acid 3-(3-diisopropylamino-1-phenylpropyl)-4-N,N-diethylcarbamoyloxybenzyl ester NMR (CDCl$_3$): 13.31, 13.64, 13.89, 20.33, 20.71, 31.57, 37.97, 41.55, 42.37, 48.46, 51.00, 67.23, 120.00, 123.39, 124.82, 126.31, 126.95, 127.33, 150.36, 157.18, 158.97.

(±)-{4-[2-(3-Diisopropylamino-1-phenylpropyl)-4-hydroxymethyl-phenoxycarbonylamino]-butyl}-carbamic acid 2-(3-diisopropylamino-1-phenylpropyl)-4-hydroxymethylphenyl ester (formula VII', X=Y=NH, n=4) tlc: R$_f$ 0.60 (6); dihydrochloride m.p. 142.5-145.6° C.

(±)-Carbonic acid 2-(3-diisopropylamino-1-phenylpropyl)-4-hydroxymethylphenyl ester ethyl ester, R$_f$ 0.67 (4)

(±)-Carbonic acid 2-(3-diisopropylamino-1-phenylpropyl)-4-ethoxycarbonyloxymethylphenyl ester ethyl ester, R$_f$ 0.87 (4)

g) Intramolecular Cyclic Diesters via Ring Closing Metathesis (RCM)

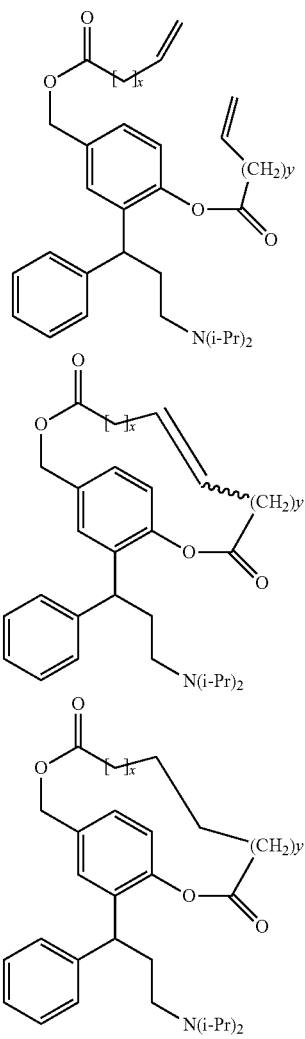

Example (±)-Pent-4-enoic acid 2-(3-diisopropylamino-1-phenylpropyl)-4-(pent-4-enoyloxymethyl)-phenyl ester (x=y=2)

A cooled (4° C.) mixture of pent-4-enoic acid, isobutyl chloroformate, and triethylamine (each 5.84 mmol) in 10 ml of dichloromethane was stirred 5 hrs under an atmosphere of dry nitrogen gas. The cooling bath was then removed and both triethylamine (1.46 mmol) and 2-(3-diisopropylamino-1-phenylpropyl)-4-hydroxymethylphenol (1.46 mmol) were added in one portion. After 18 hrs the mixture was diluted with dichloromethane (30 ml), washed several times with water and finally aqueous 5% sodium hydrogen carbonate solution. After drying (sodium sulphate), filtration and evaporation the oily residue was re-dissolved in a small volume of a solvent mixture consisting of ethyl acetate/heptane/triethylamine (65/30/5, vol.-%) and applied on a silica gel flash chromatography column. Elution of the column with the same solvent mixture, collection of the appropriate fractions, and evaporation of the combined fractions gave (±)-pent-4-enoic acid 2-(3-diisopropylamino-1-phenylpropyl)-4-(pent-4-enoyloxymethyl)-phenyl ester as a pale yellow syrupy oil (50% yield), tlc: (4) 0.75. NMR (CDCl$_3$): 18.95, 20.77, 27.75, 28.87, 33.58, 36.83, 42.13, 43.72, 48.71, 65.85, 70.55, 115.47, 115.99, 122.45, 126.26, 127.08, 127.96, 128.11, 128.83, 133.73, 136.38, 136.79, 137.04, 143.77, 148.46, 171.11, 172.78.

Intramolecular Cyclic Diesters of 1,ω-Dioic Acids and Intermediate B

Example

Intramolecular cyclic diester of octane-1,8-dioic acid and 2-(3-diisopropylamino-1-phenylpropyl)-4-hydroxymethyl-phenol Grubbs catalyst (benzylidene-bis-(tricyclohexylphosphine)-dichlororuthenium, 16 mg, 0.002 mmol, 2 mol-%) was added to a solution of (±)-pent-4-enoic acid 2-(3-diisopropylamino-1-phenylpropyl)-4-(pent-4-enoyloxymethyl)-phenyl ester (483 mg, 0.96 mmol) in dichloromethane (150 ml) and the mixture was refluxed for 96 hrs. under an atmosphere of nitrogen gas, after which all of the starting material was consumed as indicated by tlc. The mixture was filtered through a short pad of basic alumina, and the solvent was removed in vacuum. Flash chromatography (solvent system (4)) afforded the intermediate intramolecular cyclic diester of oct-4-ene-1,8-dioic acid and 2-(3-diisopropylamino)-1-(phenylpropyl)-4-hydroxymethyl-phenol (324 mg) as a colourless syrup (tlc: (4) R$_f$ 0.68) in 71% yield, mixture of two geometrical isomers.

NMR (CDCl$_3$, major isomer): 19.24, 20.61, 23.11, 25.62, 30.55, 33.53, 35.02, 42.41, 48.29, 50.20, 65.30, 114.46, 124.33, 125.58, 127.15, 128.70, 129.29, 131.10, 132.46, 139.54, 146.76, 147.98, 173.76, 174.39.

A portion of this material (140 mg) was dissolved in ethyl acetate (10 ml) and hydrogenated at room temperature in the presence of palladium-on carbon catalyst to afford the intramolecular cyclic diester of octane-1,8-dioic acid and 2-(3-diisopropylamino-1-phenylpropyl)-4-hydroxymethyl-phenol in essentially quantitative yield, 139 mg, colourless oil, tlc: (4) 0.71.

NMR (CDCl$_3$): 19.36, 20.73, 24.84, 25.28, 28.90, 29.70, 30.57, 33.72, 34.37, 42.39, 48.26, 50.20, 65.26, 114.45, 124.37, 127.11, 128.67, 129.29, 131.18, 132.45, 139.52, 146.77, 147.69, 173.90, 174.15.

Poly-Co-DL-Lactides of Intermediate B

All reagents were dried over P$_2$O$_5$ in vacuum (<1 mbar) and at room temperature. The reactions were carried out at room temperature in an atmosphere of dry, oxygen-free nitrogen.

Low Molecular Weight Copolymer

A 15% solution of n-butyllithium (0.36 ml) was injected through a rubber septum into a stirred solution of 2-(3-diisopropylamino-phenylpropyl)-4-hydroxymethyl-phenol (100 mg, Intermediate B) and DL-dilactide (1.5 g) in 1.5 ml of dry toluene. The polymerization was allowed to proceed for 4 days at room temperature. Distilled water (10 ml) was then added in order to terminate the polymerization. The organic phase was separated and slowly dropped into 200 ml of methanol. The precipitated colourless oil was treated with water (100 ml) and then dried in high vacuum for 48 hrs.

The copolymer was obtained in 72.7% yield. NMR analysis (see below) indicated an average molecular weight range of M$_n$, 2000-4000 and a weight content of Intermediate B of about 8.4% (NMR). Tlc analysis showed the absence of monomeric Intermediate B. Gel permeation chromatography (GPC) analysis showed a Mw of 1108 and a Mn of 702.

High Molecular Weight Copolymer

The high molecular weight copolymer was prepared as described above with the exception that 3.0 g of DL-dilactide was used. Precipitation by methanol gave a fluffy white solid which was carefully washed with water and then dried as described to give the copolymer in 81% yield. NMR analysis (see below) indicated an average molecular weight range of $M_n$ 4000-8000 and a weight content of Intermediate B of about 2.0%. Tlc analysis showed the absence of monomeric Intermediate B. Gel permeation chromatography (GPC) showed a Mw of 9347 and a Mn of 6981. Differential scanning calorimetry (DSC) provided a Tg of 42.5° C.

NMR Analysis

The $^1$H NMR resonance signals of the poly-lactyl chain were clearly separated from the copolymeric part of Intermediate B (solvent $CDCl_3$):

$CH_3$ resonances of the poly-lactyl chain: 1.30-1.60 ppm CH resonances of the poly-lactyl chain: 5.10-5.30 ppm CH resonances of the connecting lactyl units with the two hydroxy groups of Intermediate B: 4.8-5.0 ppm and 5.5-5.7 ppm.

Polymer bound Intermediate B: 1.06-1.11 ($CH_3$), 2.20-2.30 ($CH_2CH_2$), 2.40-2.80 ($NCH_2$), 3.30-3.50 (NCH), 4.45-4.55 ($CH\underline{CH_2}$), 4.70-4.80 ($\underline{CH_2}$—OCO-lactyl), 6.70-7.30 (aryl $\underline{CH}$)

h) Inorganic Ester

Example (±)-Benzoic acid 2-(3-diisopropylamino-1-phenyl-propyl)-4-sulphooxymethyl-phenyl ester Hydrochloride To a stirred solution of chlorosulphonic acid (116 mg, 1.0 mmol) in 5 ml of dry diethyl ether was slowly added at 0° C. a solution of (±)-benzoic acid 2-(3-diisopropylamino-1-phenyl-propyl)-4-hydroxymethylphenyl ester (445.6 mg, 1.0 mmol) in 3 ml of dry diethyl ether. The gel formed immediately during the addition was stirred at room temperature until it became a crystalline consistency (ca. 1 hr). The precipitate was washed several times with diethyl ether and then dried in vacuum to give 0.52 g (46% yield) colourless crystals, m.p. 63-65° C. NMR ($CDCl_3$): 16.85, 17.03, 18.32, 18.49, 32.01, 42.29, 46.23, 55.23, 55.50, 69.24, 122.52, 126.94, 127.15, 129.04, 129.76, 130.25, 133.89, 134.93, 136.85, 141.87, 147.80, 165.19.

i) Benzylic 1-O-β-D-glucuronide of 2-(3-diisopropylamino-1-phenylpropyl)-4-hydroxymethylphenol ((±)-2-(3-Diisopropylamino-1-phenylpropyl)-4-(1β-D-glucuronosyloxymethyl)-phenol)

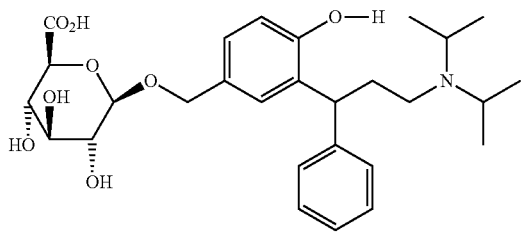

A solution of methyl 2,3,4-triacetyl-1-α-D-glucuronosyl-bromide (2.07 g, 4.64 mmol) in 24 ml of dry toluene was cooled to −25° C. under an atmosphere of nitrogen and then treated with a solution of (±)-benzoic acid 2-(3-diisopropylamino-1-phenylpropyl)-4-hydroxymethylphenyl ester in 7 ml of toluene. To this mixture was added dropwise with stirring and under protection from light a solution of silver triflate in 14 ml of toluene (immediate formation of a white precipitate). The cooling bath was removed after 15 min and pyridine (0.38 ml) was added. The mixture was diluted with ethyl acetate (200 ml), filtered and the clear yellow filtrate was washed sequentially with aqueous solutions of sodium thiosulphate (5%), sodium hydrogen carbonate (5%), and sodium chloride (20%). The solution was dried with solid sodium sulphate, treated with charcoal, filtered and evaporated to dryness. The waxy residue was re-dissolved in a small volume of a solvent mixture consisting of ethyl acetate/heptane/triethylamine (65/30/5, vol.-%) and applied on a silica gel flash chromatography column. Elution of the column with the same solvent mixture, collection of the appropriate fractions, and evaporation of the combined fractions gave (±)-benzoic acid 2-(3-diisopropylamino-1-phenylpropyl)-4-(2,3,4-triacetyl-1β-D-glucuronosyloxymethyl)-phenyl ester, colourless syrup, tlc (4) 0.70 (starting amine: 0.31, bromo glycoside: 0.23), yield 14%.

NMR ($CDCl_3$, mixture of diastereomers): 20.41, 20.50, 20.60, 20.65, 20.84, 36.49, 42.44, 43.65, 48.73, 52.91, 69.46, 70.43, 71.12, 72.11, 72.60, 73.99, 99.19, 122.91, 126.23, 126.38, 126.54, 127.60, 127.92, 128.06, 128.09, 128.31, 128.59, 129.38, 130.22, 133.67, 134.31, 137.41, 143.52, 148.46, 164.82, 167.26, 169.21, 169.39, 170.07.

A portion (350 mg) of the above described material was dissolved and hydrolyzed in a solvent mixture consisting of tetrahydrofuran/methanol/aqueous potassium hydroxide (excess, 12 hrs, 22° C.). The mixture was evaporated, re-dissolved in 5 ml of water and the pH was adjusted to 8.3. This solution was applied to a chromatography column charged with prewashed XAD 2 resin (50 g). The column was washed with water (ca. 250 ml) and then eluted with methanol. Collection of the appropriate methanol fractions, and evaporation of the combined fractions in vacuum gave 111 mg of (±)-2-(3-diisopropylamino-1-phenylpropyl)-4-(1β-D-glucuronosyloxymethyl)-phenol, sodium salt, amorphous colourless solid, m.p. 110-124° C. (dec.), tlc (4) 0.12. NMR ($CD_3OD$, major isomer): 19.43, 19.67, 33.26, 39.63, 42.27, 48.23, 69.76, 73.55, 74.70, 75.95, 78.03, 107.64, 117.95, 125.51, 127.36, 128.33, 133.83, 134.77, 144.49, 155.36, 176.76.

II. Incubations of Different Compounds of the Invention with Human Liver S 9-Fraction a) Incubation of Unlabelled Substrates A pooled human liver S 9-preparation was used to show the in-vitro metabolism of different compounds of the invention and to prove the generation of the active metabolite by enzymatic process.

The pooled human liver S 9-preparation was delivered by Gentest, Woburn, Mass., USA.

In a routine assay, 25 µL of pooled human liver S9 (20 mg protein/mL, H961, Gentest, Woburn, Mass., USA) was incubated for 2 hrs at 37° C. with 40 µM substrate in a 0.01 M potassium phosphate buffer in the presence of NADPH (1 mM). The reaction was quenched by the addition of concentrated perchloric acid and precipitating protein was removed by centrifugation. The supernatant was adjusted to pH 3 with concentrated potassium phosphate solution, centrifuged, and injected into the HPLC for analysis of the respective products.

The analysis of the non-deuterated compounds was performed by a routine High Pressure Liquid Chromatography (HPLC) method with UV-detection.

The incubation results expressed in (%) of theoretical turnover are presented in FIG. 1.

They ranged from 96 to 63.2%. The formation of the active metabolite is dependent on the substituents both at the benzylic and phenolic side of the respective compounds.

Explanation:

The prodrugs introduced in the assay show the following chemical structure:

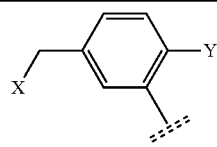

| chemical structure | X—/—Y | |
|---|---|---|
| AcO—/—OAc | means acetate | |
| HO—/—OBut | means hydroxy and n-butyrate | |
| HO—/—OiBut | means hydroxy and iso-butyrate | |
| iButO—/—OiBut | means iso-butyrate | |
| ButO—/—OBut | means n-butyrate | |
| PropO—/—OProp | means proprionate | |
| HO—/—OProp | means hydroxy and proprionate | |
| HO—/—OAc | means hydroxy and acetate | |
| BzO—/—OBz | means benzoate and benzoate | |
| AcO—/—OiBut | means acetate and isobutyrate | |
| AcO—/—OBz | means acetate and benzoate | | b) Incubation of Labelled Substrates

The metabolic degradation of the unlabelled hydroxy metabolite (i.e. Intermediate B) and the deuteriated hydroxymetabolite (Intermediate $d_2$B) were compared in vitro. Used were the respective enantiomers and the racemates.

The hydroxy metabolite and the deuteriated hydroxy-metabolite expressed significant differences in the rate to produce the corresponding carboxylic acid.

The measurement was performed with an incubation time of 3 hrs at 37.0° C. in a concentration of 40 µM. The formation of the carboxylic acid from the deuteriated hydroxy-metabolite showed a significantly decreased velocity of 10%.

These in-vitro experiments indicate a reduced metabolic turnover of the deuteriated compound in vitro, which may result in higher plasma levels.

c) Receptor Binding Study

WO 94/11337 discloses that the active metabolite has high affinity to muscarinic receptors in the guinea-pig bladder. Different compounds of the present invention were tested in a well established standardized assay, measuring the binding of [$^3$H]-methylscopolamine to recombinant human M3 receptors. BSR-M3H cells transfected with a plasmid encoding the human muscarinic M3 receptor were used to prepare membranes in modified Tris-HCl pH 7.4 buffer using standard techniques. An aliquot of the membrane preparation was incubated with [$^3$H]-methylscopolamine in the presence or absence of different concentrations of several compounds of the invention for 60 minutes at 25° C. Nonspecific binding was estimated in the presence of 1 µM atropine. Membranes were filtered and washed three times and the filters were counted to determine the amount of [$^3$H]-methylscopolamine specifically bound. The following table shows the $IC_{50}$ values of several compounds of the invention in the M3 receptor binding assay.

Interaction with human M3 receptors in vitro

| Prodrug | $IC_{50}$ [nM] |
|---|---|
| (+)HO—/—OH | 8.7 |
| (−)HO—/—OH | 1300 |
| (+)HO—/—OiBut | 159 |
| (+)HO—/—OBz | 172 |
| BzO—/—OBz | 2400 |
| AcO—/—OiBut | 3600 |
| AcO—/—OBz | 5400 |

These data clearly showed that derivatization at the phenolic hydroxyl moiety results in an about 20 times less potent binding. If both functionalities are derivatized, the binding is even more dramatically reduced. Furthermore, it is demonstrated that the enantiomers of the active metabolite exhibit a marked difference in the binding characteristics to human M3 receptors.

The compounds were tested for their anticholinergic activity in a standard tissue assay, the guinea-pig ileum. A segment of ileum was obtained from Duncan Hartley guinea-pigs which were sacrificed by cervical dislocation. The tissue was placed under 1 g tension in a 10 ml bath containing Krebs' solution (pH 7.4, 32° C.) and the concentration-dependent ability of different compounds to reduce the methacholine-induced (0.6 µM) contractile response was recorded. The $IC_{50}$ values for the different substances were calculated and examples are presented in the following table.

Anticholinergic activity in guinea-pig ileum in vitro

| Prodrug | $IC_{50}$ [nM] |
|---|---|
| (+)HO—/—OH | 20 |
| (−)HO—/—OH | 680 |
| (+)HO—/—OiBut | 57 |
| (+)HO—/—OBz | 180 |
| (+)BzO—/—OBz | 220 |
| (+)AcO—/—OiBut | 240 |

These data confirm the results obtained in the receptor binding assays and demonstrate that the anticholinergic activity of the compounds decreases with increased derivatization.

d) Biological Membranes

Different compounds of the invention were tested for their ability to penetrate the human skin (200 µm thick) in the "Flow through cell" at 32° C. according to Tiemessen et al. (Acta Pharm. Technol. 1998; 34:99-101). Phosphate buffer (pH 6.2) was used as the acceptor medium. Samples were drawn at different time points and analysed by RP-HPLC with UV detection (220 nm). Permeation profiles were plotted and mean flux rates of different substances were calculated by linear regression analysis. The data obtained for different compounds of the invention are summarized in the following table.

Penetration Through Human Skin

| Prodrug | Flux rate [μg/cm$^2$/24 hrs] |
|---|---|
| HO—/—OH | 3 |
| HO—/—OiBut | 150 |
| iButO—/—OiBut | 60 |
| PropO—/—OProp | 70 |

Disubstitution of the hydroxy group of HO—/—OH leads to a ≧20-fold increase in skin permeation in relation to the parent H—/—OH. Suprisingly monosubstitution of the penolic hydroxy group resulted in even higher 50-fold penetration rate through human skin.

Taken together, these biological data clearly demonstrate that the compounds of the invention have a reduced affinity to bind to human muscarinic M3 receptors. They exhibit an increased penetration through biological membranes, e.g. the human skin, and they are rapidly transformed to the active metabolite, once they have entered the systemic circulation as shown by the in vitro metabolism by the human liver S9 preparation.

Thus, the antimuscarinic prodrugs according to this invention showed a profile that defines excellent prodrugs.

The invention claimed is:

1. 3,3-Diphenylpropylamines of the formula

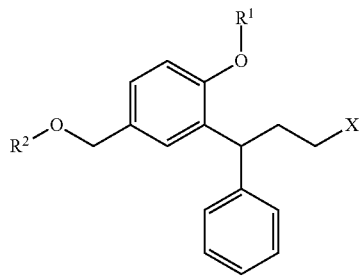

where:
R$^1$ is hydrogen and R$^2$ is C$_1$-C$_6$ alkylcarbonyl; or
R$^1$ is C$_1$-C$_6$ alkylcarbonyl and R$^2$ is hydrogen; and
X is a tertiary amino group of formula

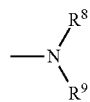

where R$^8$ and R$^9$ are each independently C$_1$-C$_8$ alkyl and together comprise at least three carbon atoms;
their salts with physiologically acceptable acids, their free bases and, when the 3,3-Diphenylpropylamines are in the form of optical isomers, the racemic mixture and the individual enantiomers.

2. The 3,3-Diphenylpropylamines of claim 1 where R$^8$ and R$^9$ are each independently C$_1$-C$_6$ alkyl.

3. The 3,3-Diphenylpropylamines of claim 1 where X is selected from the group consisting of:

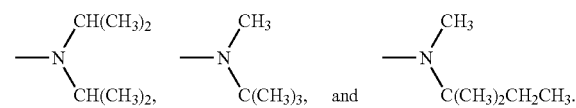

4. The 3,3-Diphenylpropylamines of claim 1 where R$^1$ is hydrogen and R$^2$ is C$_1$-C$_6$ alkylcarbonyl.

5. The 3,3-Diphenylpropylamines of claim 1 where R$^1$ is C$_1$-C$_6$ alkylcarbonyl and R$^2$ is hydrogen.

6. A method of treating urinary incontinence in a patient in need thereof, the method comprising administering to the patient an effective amount of a 3,3-Diphenylpropylamine of the formula

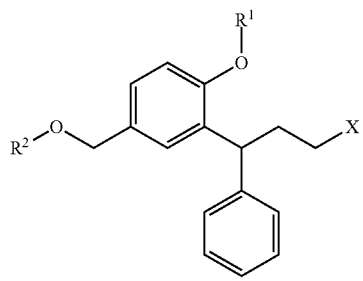

where:
R$^1$ is hydrogen and R$^2$ is C$_1$-C$_6$ alkylcarbonyl; or
R$^1$ is C$_1$-C$_6$ alkylcarbonyl and R$^2$ is hydrogen; and
X is a tertiary amino group of formula

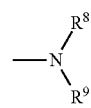

where R$^8$ and R$^9$ are each independently C$_1$-C$_8$ alkyl and together comprise at least three carbon atoms;
or its salt with a physiologically acceptable acid, its free base or, when the 3,3-Diphenylpropylamine is in the form of optical isomers, the racemic mixture and the individual enantiomers.

7. The method of claim 6 where R$^8$ and R$^9$ are each independently C$_1$-C$_6$ alkyl.

8. The method of claim 6 where X is selected from the group consisting of:

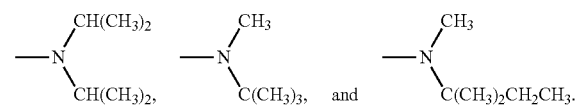

9. The method of claim 6 where R$^1$ is hydrogen and R$^2$ is C$_1$-C$_6$ alkylcarbonyl.

10. The method of claim 6 where R$^1$ is C$_1$-C$_6$ alkylcarbonyl and R$^2$ is hydrogen.

11. The method of claim 6, where the 3,3-Diphenylpropylamine is administered to the patient in the form of a pharmaceutical composition comprising a pharmaceutically acceptable carrier.

12. A pharmaceutical composition comprising an effective amount of a 3,3-Diphenylpropylamine according to any one of claims 1-5 and a pharmaceutically acceptable carrier.

* * * * *